US010283217B2

(12) United States Patent
Lui et al.

(10) Patent No.: US 10,283,217 B2
(45) Date of Patent: *May 7, 2019

(54) SYSTEMS AND METHODS FOR DETECTING INFECTIOUS DISEASES

(71) Applicant: Theranos IP Company, LLC, Newark, CA (US)

(72) Inventors: Clarissa Lui, Menlo Park, CA (US); Elizabeth A. Holmes, Palo Alto, CA (US); Pranav Patel, Palo Alto, CA (US); Scott Tabakman, Palo Alto, CA (US); Kamila Belhocine, Palo Alto, CA (US); Aaron Richardson, Palo Alto, CA (US); Josephine Lee, Hayward, CA (US)

(73) Assignee: Theranos IP Company, LLC, New York, NY (US)

(*) Notice: Subject to any disclaimer, the term of this patent is extended or adjusted under 35 U.S.C. 154(b) by 97 days.

This patent is subject to a terminal disclaimer.

(21) Appl. No.: 14/789,904

(22) Filed: Jul. 1, 2015

(65) Prior Publication Data

US 2016/0070884 A1 Mar. 10, 2016

Related U.S. Application Data

(63) Continuation of application No. 14/479,241, filed on Sep. 5, 2014, now Pat. No. 9,529,976.

(60) Provisional application No. 62/010,382, filed on Jun. 10, 2014, provisional application No. 62/001,053, filed on May 21, 2014, provisional application No. 62/001,039, filed on May 20, 2014, provisional application No. 61/885,462, filed on Oct. 1, 2013, (Continued)

(51) Int. Cl.
| | | |
|---|---|---|
| C12Q 1/68 | (2018.01) |
| C12Q 1/70 | (2006.01) |
| G06F 19/00 | (2018.01) |
| G01N 33/569 | (2006.01) |
| G16H 10/40 | (2018.01) |
| C12Q 1/689 | (2018.01) |
| C12Q 1/6893 | (2018.01) |
| C12Q 1/6895 | (2018.01) |
| G01N 35/10 | (2006.01) |
| C12Q 1/6844 | (2018.01) |
| C12Q 1/6806 | (2018.01) |
| G16H 50/20 | (2018.01) |
| G16H 20/10 | (2018.01) |
| G01N 35/00 | (2006.01) |

(52) U.S. Cl.
CPC .............. *G16H 10/40* (2018.01); *C12Q 1/689* (2013.01); *C12Q 1/6893* (2013.01); *C12Q 1/6895* (2013.01); *C12Q 1/70* (2013.01); *C12Q 1/701* (2013.01); *C12Q 1/703* (2013.01); *C12Q 1/705* (2013.01); *C12Q 1/706* (2013.01); *C12Q 1/707* (2013.01); *G01N 33/56911* (2013.01); *G01N 33/56916* (2013.01); *G01N 33/56938* (2013.01); *G01N 33/56944* (2013.01); *G01N 33/56983* (2013.01); *G01N 33/56988* (2013.01); *G01N 33/56994* (2013.01); *G01N 35/10* (2013.01); *G06F 19/00* (2013.01); *C12Q 1/68* (2013.01); *C12Q 1/6806* (2013.01); *C12Q 1/6844* (2013.01); *C12Q 2521/501* (2013.01); *C12Q 2600/158* (2013.01); *C12Q 2600/16* (2013.01); *G01N 2035/00237* (2013.01); *G01N 2333/11* (2013.01); *G01N 2469/10* (2013.01); *G01N 2469/20* (2013.01); *G06F 19/3456* (2013.01); *G16H 20/10* (2018.01); *G16H 50/20* (2018.01); *Y02A 50/58* (2018.01); *Y02A 90/24* (2018.01); *Y02A 90/26* (2018.01); *Y10T 436/11* (2015.01)

(58) Field of Classification Search
None
See application file for complete search history.

(56) References Cited

U.S. PATENT DOCUMENTS

| | | | |
|---|---|---|---|
| 4,683,195 A | 7/1987 | Mullis et al. |
| 4,756,884 A | 7/1988 | Hillman et al. |

(Continued)

FOREIGN PATENT DOCUMENTS

| | | | |
|---|---|---|---|
| CA | 1340121 E | 11/1998 |
| CN | 101906488 A | 12/2010 |

(Continued)

OTHER PUBLICATIONS

Preliminary Amendment dated Apr. 29, 2016 for U.S. Appl. No. 15/041,421.

(Continued)

*Primary Examiner* — David C Thomas

(57) ABSTRACT

Systems, methods, and devices for detecting infections in a clinical sample are provided. Small-volume clinical samples obtained at a point-of-service (POS) location and may be tested at the POS location for multiple markers for multiple diseases, including upper and lower respiratory diseases. Samples may be tested for cytokines, or for inflammation indicators. Dilution of samples, or levels of detection, may be determined by the condition or past history of a subject. Test results may be obtained within a short amount of time after sample placement in a testing device, or within a short amount of time after being obtained from the subject. A prescription for treatment of a detected disorder may be provided, and may be filled, at the POS location. A bill may be automatically generated for the testing, or for the prescription, may be automatically sent to an insurance provider, and payment may be automatically obtained.

20 Claims, 38 Drawing Sheets

Related U.S. Application Data provisional application No. 61/874,976, filed on Sep. 6, 2013.

(56) References Cited

U.S. PATENT DOCUMENTS

| | | | |
|---|---|---|---|
| 5,834,252 A | 11/1998 | Stemmer et al. | |
| 5,874,260 A | 2/1999 | Cleuziat et al. | |
| 6,033,881 A | 3/2000 | Himmler et al. | |
| 6,090,552 A | 7/2000 | Nazarenko et al. | |
| 6,194,179 B1 | 2/2001 | Werner et al. | |
| 6,235,502 B1 | 5/2001 | Weissman et al. | |
| 6,379,929 B1 | 4/2002 | Burns et al. | |
| 6,468,474 B2 | 10/2002 | Bachand et al. | |
| 6,620,597 B1 | 9/2003 | Chen et al. | |
| 6,743,605 B1 | 6/2004 | Rabbani et al. | |
| 6,764,821 B1 | 7/2004 | Rabbani et al. | |
| 6,916,634 B2 | 7/2005 | Kopreski | |
| 6,949,377 B2 | 9/2005 | Ho | |
| 6,977,148 B2 | 12/2005 | Dean et al. | |
| 7,264,930 B2 | 9/2007 | Rabbani et al. | |
| 7,297,485 B2 | 11/2007 | Bomarth et al. | |
| 7,468,245 B2 | 12/2008 | Rabbani et al. | |
| 7,485,417 B2 | 2/2009 | Rabbani et al. | |
| 7,494,791 B2 | 2/2009 | Goel | |
| 7,713,691 B2 | 5/2010 | Rabbani et al. | |
| 7,803,579 B2 | 9/2010 | Mitani et al. | |
| 7,955,795 B2 | 6/2011 | Kumar | |
| 7,993,839 B2 | 8/2011 | Nelson et al. | |
| 8,088,593 B2 | 1/2012 | Burd et al. | |
| 8,133,989 B2 | 3/2012 | Rabbani et al. | |
| 8,158,430 B1 | 4/2012 | Roy et al. | |
| 8,206,902 B2 | 6/2012 | Mitani et al. | |
| 8,236,499 B2 | 8/2012 | Patel et al. | |
| 8,288,092 B2 | 10/2012 | Rabbani et al. | |
| 8,380,541 B1 | 2/2013 | Holmes | |
| 8,420,323 B2 | 4/2013 | Miyoshi et al. | |
| 8,435,738 B2 | 5/2013 | Holmes | |
| 8,435,741 B2 | 5/2013 | Miyoshi et al. | |
| 8,445,664 B2 | 5/2013 | Rabbani et al. | |
| 8,486,633 B2 | 7/2013 | Rabbani et al. | |
| 9,131,884 B2 | 9/2015 | Holmes et al. | |
| 9,529,976 B2 * | 12/2016 | Lui | C12Q 1/689 |
| 2001/0049125 A1 | 12/2001 | Stemmer et al. | |
| 2004/0209272 A1 | 10/2004 | Ben-Asouli et al. | |
| 2005/0084894 A1 | 4/2005 | Brow et al. | |
| 2005/0100937 A1 | 5/2005 | Holmes | |
| 2005/0112631 A1 | 5/2005 | Piepenburg et al. | |
| 2005/0220668 A1 | 10/2005 | Coville | |
| 2005/0277146 A1 | 12/2005 | Shigemori et al. | |
| 2006/0019274 A1 | 1/2006 | Goel | |
| 2006/0040300 A1 | 2/2006 | Dapprich et al. | |
| 2006/0074063 A1 | 4/2006 | Fernandez-Pol | |
| 2006/0188893 A1 | 8/2006 | Kumar et al. | |
| 2006/0194214 A1 | 8/2006 | Church et al. | |
| 2006/0264780 A1 | 11/2006 | Holmes et al. | |
| 2006/0264782 A1 | 11/2006 | Holmes et al. | |
| 2007/0054301 A1 | 3/2007 | Becker et al. | |
| 2007/0141048 A1 | 6/2007 | Oleksiewicz et al. | |
| 2007/0154922 A1 | 7/2007 | Collier et al. | |
| 2007/0224084 A1 | 9/2007 | Holmes et al. | |
| 2007/0264629 A1 | 11/2007 | Holmes et al. | |
| 2008/0153096 A1 | 6/2008 | Witty et al. | |
| 2008/0227160 A1 | 9/2008 | Kool | |
| 2008/0305535 A1 | 12/2008 | Auerbach | |
| 2009/0081648 A1 | 3/2009 | Wangh | |
| 2009/0088336 A1 | 4/2009 | Burd et al. | |
| 2009/0098566 A1 | 4/2009 | Notomi et al. | |
| 2009/0098612 A1 | 4/2009 | Rhee et al. | |
| 2009/0143235 A1 | 6/2009 | Drmanac et al. | |
| 2009/0155856 A1 | 6/2009 | Miyoshi et al. | |
| 2009/0170096 A1 | 7/2009 | Miyoshi et al. | |
| 2009/0203085 A1 | 8/2009 | Kurn et al. | |
| 2009/0233277 A1 | 9/2009 | Murakami | |
| 2010/0015634 A1 | 1/2010 | VanDine et al. | |
| 2010/0029505 A1 | 2/2010 | Payan et al. | |
| 2010/0075384 A1 | 3/2010 | Kong et al. | |
| 2010/0111773 A1 | 5/2010 | Pantelidis | |
| 2010/0151471 A1 | 6/2010 | Faham et al. | |
| 2010/0180980 A1 | 7/2010 | Lee et al. | |
| 2010/0184154 A1 | 7/2010 | Miyoshi et al. | |
| 2011/0093249 A1 | 4/2011 | Holmes et al. | |
| 2011/0123991 A1 | 5/2011 | Hoser | |
| 2011/0207617 A1 | 8/2011 | Faham et al. | |
| 2012/0070831 A1 | 3/2012 | Johnson | |
| 2012/0156642 A1 | 6/2012 | Papanek et al. | |
| 2012/0157326 A1 | 6/2012 | Tisi et al. | |
| 2012/0309636 A1 | 12/2012 | Gibbons et al. | |
| 2013/0074614 A1 | 3/2013 | Holmes et al. | |
| 2013/0078149 A1 | 3/2013 | Holmes et al. | |
| 2013/0078624 A1 | 3/2013 | Holmes et al. | |
| 2013/0078625 A1 | 3/2013 | Holmes et al. | |
| 2013/0078733 A1 | 3/2013 | Holmes et al. | |
| 2013/0079599 A1 | 3/2013 | Holmes et al. | |
| 2013/0080071 A1 | 3/2013 | Holmes | |
| 2013/0243794 A1 | 9/2013 | Hauser | |
| 2013/0296535 A1 | 11/2013 | Church et al. | |
| 2014/0045170 A1 | 2/2014 | Patel et al. | |
| 2014/0057255 A1 | 2/2014 | Holmes | |
| 2014/0057770 A1 | 2/2014 | Holmes et al. | |
| 2014/0073043 A1 | 3/2014 | Holmes | |
| 2014/0081665 A1 | 3/2014 | Holmes | |
| 2014/0113839 A1 | 4/2014 | Wu et al. | |
| 2014/0170678 A1 * | 6/2014 | Kasdan | B01L 3/502 |
| | | | 435/7.24 |
| 2014/0170688 A1 | 6/2014 | Matje et al. | |
| 2014/0170735 A1 | 6/2014 | Holmes | |
| 2014/0229955 A1 | 8/2014 | Holmes et al. | |
| 2014/0234949 A1 | 8/2014 | Wasson et al. | |
| 2014/0272938 A1 | 9/2014 | Loo et al. | |
| 2014/0287955 A1 | 9/2014 | Wende et al. | |
| 2014/0295439 A1 | 10/2014 | Patel | |
| 2014/0295440 A1 | 10/2014 | Belhocine et al. | |
| 2014/0295447 A1 | 10/2014 | Hayashizaki et al. | |
| 2014/0295498 A1 | 10/2014 | Turner et al. | |
| 2014/0296089 A1 | 10/2014 | Holmes et al. | |
| 2014/0302504 A1 | 10/2014 | Belhocine et al. | |
| 2014/0308661 A1 | 10/2014 | Holmes et al. | |
| 2014/0335505 A1 | 11/2014 | Holmes | |
| 2014/0342371 A1 | 11/2014 | Holmes | |
| 2014/0364764 A1 | 12/2014 | Jung et al. | |
| 2015/0072338 A1 | 3/2015 | Holmes | |
| 2015/0072362 A1 | 3/2015 | Lui et al. | |
| 2015/0072889 A1 | 3/2015 | Lui et al. | |
| 2015/0140567 A1 | 5/2015 | Belhocine et al. | |
| 2015/0299777 A1 | 10/2015 | Patel et al. | |
| 2016/0060673 A1 | 3/2016 | Belhocine et al. | |
| 2016/0060674 A1 | 3/2016 | Patel | |
| 2016/0068895 A1 | 3/2016 | Belhocine et al. | |
| 2016/0076069 A1 | 3/2016 | Belhocine et al. | |
| 2016/0245810 A1 | 8/2016 | Patel et al. | |
| 2016/0281155 A1 | 9/2016 | Patel | |
| 2017/0168051 A1 | 6/2017 | Lui et al. | |

FOREIGN PATENT DOCUMENTS

| | | |
|---|---|---|
| EP | 0833942 B1 | 8/2000 |
| EP | 2048248 A1 | 4/2009 |
| EP | 0971039 B1 | 3/2011 |
| EP | 2692870 A1 | 2/2014 |
| GB | 2332516 A | 6/1999 |
| JP | 04131099 | 5/1992 |
| JP | 07016094 | 1/1995 |
| JP | 07067646 A2 | 3/1995 |
| RU | 2147123 C1 | 3/2000 |
| WO | 1992001813 A1 | 2/1992 |
| WO | 1994003624 A1 | 2/1994 |
| WO | 1996001327 A1 | 1/1996 |
| WO | 1997004131 A1 | 2/1997 |
| WO | 1999004043 A1 | 1/1999 |
| WO | 2000079009 A2 | 12/2000 |
| WO | 02068683 A2 | 9/2002 |
| WO | 2004055198 A2 | 7/2004 |
| WO | 2004061119 A2 | 7/2004 |
| WO | 2004061418 A2 | 7/2004 |

(56) References Cited

FOREIGN PATENT DOCUMENTS

| | | | |
|---|---|---|---|
| WO | 2004070053 | A2 | 8/2004 |
| WO | 2005030983 | A2 | 4/2005 |
| WO | 2005059178 | A1 | 6/2005 |
| WO | 2006095169 | A1 | 9/2006 |
| WO | 2006119066 | A2 | 11/2006 |
| WO | 2008012529 | A1 | 1/2008 |
| WO | 2008032058 | A2 | 3/2008 |
| WO | 2008050254 | A1 | 5/2008 |
| WO | 2008115632 | A2 | 9/2008 |
| WO | 2009120374 | A2 | 10/2009 |
| WO | 2012017210 | A1 | 2/2012 |
| WO | 2010090857 | | 6/2012 |
| WO | 2013003585 | A2 | 1/2013 |
| WO | 2013006312 | A2 | 3/2013 |
| WO | 2013035875 | A1 | 3/2013 |
| WO | 2013052318 | A1 | 4/2013 |
| WO | 2014025337 | A1 | 2/2014 |
| WO | 2015035256 | A2 | 3/2015 |
| WO | 2015035260 | A1 | 3/2015 |

OTHER PUBLICATIONS

Notice of Allowance dated Jun. 6, 2016 for U.S. Appl. No. 14/479,245.
Office Action dated Apr. 18, 2016 for U.S. Appl. No. 14/479,241.
Advisory Action dated 9/25/15 for U.S. Appl. No. 14/479,241.
Anders et al., Am Journal Med Hyg 87(1), 2012, pp. 165-170.
AppliedBiosystems StepOne Real-Time PCR System Manual, Rev. 2010.
B. Rodriguez-Sanchez et al. Improved Diagnosis for Nine Viral Diseases Considered as Notifiable by the World Organization for Animal Health. Transbound Emerg Dis. Aug. 2008; 55(5-6): 215-25.
Chantreuil J. et al. "Artial chaotic tachycardia during a respiratory tract infection due to NL63 coronavirus". Arch Pediatr, Mar. 2013; 20(3):pp. 278-281, abstract.
Dapat I.C. et al. Genetic characterization of human influenza viruses in the pandemic (2009-2010) and post-pandemic (2010-2011) periods in Japan. PLoS One, 2012; 7(6):e36455.
Diamandis. Theranos phenomenon: promises and fallacies. Clin Chem Lab Med. Jun. 2015;53(7):989-93.
Gill, et al. Nucleic acid isothermal amplification technologies: a review. Nucleosides, Nucleotides and Nucleic Acids. Mar. 2008; 27(3):224-43.
Hung et al. Effect of clinical and virological parameters on the level of neutralizing antibody against pandemic influenza a virus H1N1 2009. Clin Infect Dis. Aug. 1, 2010;51(3):274-9.
Kautner et al., Journal of Pediatrics, 1997, 131, pp. 516-524.
Kimura Y et al. Tail variation of the folding primer effects the SmartAmp2 process differently. Biochem Biophys Res Commun. Jun. 12, 2009;383(4):455-9.
Li, Peng. (2012) Microfluidics for IVD: In Pursuit of the Holy Grail. J Bioengineer & Biomedical Sci S8:e001.
Lounsbury et al., Lab Chip, 2013, 13, pp. 1384-1393.
Luk F.O. et al. A case of dengue maculopathy with spontaneous recovery. Case Rep Ophthalmol, Jun. 8, 2013;4(2):pp. 28-33.
Obryadina A.P. et al, "Avidnost antitel v diagnostike infektsionnykh zabolevaniy" Laboratornaya diagnostika infektsionnykh zabolevaniy, 2007, No. 4, p. 3-7.
Office Action dated Jan. 19, 2015 for U.S. Appl. No. 14/479,241.
Office Action dated Nov. 12, 2014 for U.S. Appl. No. 14/479,245.
Office Action dated Nov. 19, 2015 for U.S. Appl. No. 14/604,194.
Office Action dated Feb. 12, 2015 for U.S. Appl. No. 14/479,190.
Office Action dated Apr. 3, 2015 for U.S. Appl. No. 14/479,245.
Office Action dated Jul. 8, 2015 for U.S. Appl. No. 14/479,241.
Office Action dated Sep. 24, 2015 for U.S. Appl. No. 14/479,245.
Plebani. Evaluating and using innovative technologies: a lesson from Theranos? Clin Chem Lab Med. Jun. 2015;53 (7):961-2.
Roskos et al. Simple System for Isothermal DNA Amplification Coupled to Lateral Flow Detection. PLOS One. Jul. 26, 2013;8(7):e69335. Print 2013.
Sahni et al. Reverse transcription loop-mediated isothermal amplification (RT-LAMP) for diagnosis of dengue. Med J Armed Forces India. Jul. 2013; 69(3):246-53. doi: 10.1016/j.mjafi.2012.07.017. Epub Dec. 1, 2012.
Voudoukis et al., 2011, Med Sci Monit, 17(4), pp. 185-188.
Wang Y. et al. "Methicillin resistant *Staphyloccus aureus* infection: a case report and literature review". Zhonghua Jie He Hu Xi Za Zhi, Sep. 2009; 32(9):pp. 665-659, abstract.
World Health Organization (WHO) Guide to Field Operations, Oct. 2006, pp. 1-80.
Written Opinion and International Search Report dated Dec. 18, 2014 for PCT/US2014/054424.
Zimmerman O et al. C-reactive protein serum levels as an early predictor of outcome in patients with pandemic H1N1 influenza A virus infection. BMC Infect Dis. Oct. 4, 2010;10:288.
510(k) Substantial Equivalence Determination Decision Summary dated Jul. 16, 2015 for "Theranos Herpes Simplex Virus-1 (HSV-1) IgG Assay".
510(k) Substantial Equivalence Determination issued for "Theranos Herpes Simplex Virus-1 IgG Assay" by the FDA on Jul. 7, 2015.
Chin et al. Low-Cost Microdevices for Point-of-Care Testing. Biological and Medical Physics, Biomedical Engineering pp. 3-21. Oct. 12, 2012.
Fuller K. Centers for Medicare and Medicaid Services (CMS). Condition Level Deficiencies Notice—Immediate Jeopardy. Notice to Theranos, Inc. director Dr. Sunil Dhawan. 1/25/2016. https://cdn2.vox-cdn.com/uploads/chorus_asset/file/5969923fTheranos_Inc_Cover_Letter_01-25-2016.0.pdf.
Havlickova M et al. Influenza virus detection in clinical specimens. Abstract. Acta Viral. Sep. 1990;34(5):449-56.
Jannetto et al. Real-Time Detection of Influenza A, Influenza B, and Respiratory Syncytial Virus A and B in Respiratory Specimens by Use of Nanoparticle Probes. J Clin Microbiol. Nov. 2010;48(11):3997-4002. Epub Sep. 8, 2010.
Loria K. More skeptical than ever: Experts respond to the government's warning letter to Theranos. Jan. 28, 2016. Tech Insider. http://www.techinsider/io/how-bad-the-cms-letter-to-theranos-really-is-2016-1.
Mahony et al. Molecular diagnosis of respiratory virus infections. Crit Rev Clin Lab Sci. Sep.-Dec. 2011;48(5-6):217-49.
Metzgar D. et al. Single assay for simultaneous detection and differential identification of human and avian influenza virus types, subtypes, and emergent variants. PLoS One. Feb. 3, 2010;5(2):e8995.
Office Action dated Feb. 24, 2016 for U.S. Appl. No. 14/479,245.
Office Action dated Mar. 8, 2016 for U.S. Appl. No. 14/604,194.
Ramsey L. Theranos has a week to respond to the searing report about its business. Business Insider. Feb. 5, 2016. http://www.businessinsider.com/theranos-response-to-cms-2016-2.
Rappleye E. Theranos gets extension to fix issues following CMS investigation. Becker's Hospital Review. Feb 8, 2016. http://www.beckershospitalreview.com/hospital-management-adminstration/theranos-gets-extension-to-fix-issues-following-cms-investigation.html.
Advisory Action dated Jan. 29, 2016 for U.S. Appl. No. 14/546,998.
Advisory Action dated Dec. 24, 2015 for U.S. Appl. No. 14/546,998.
Ashford. PATH using TwistDx's Amplification Tech in Minimally Instrumented HIV Test for Infants, GenomeWeb, Aug. 25, 2011.
Craw et al. Isothermal nucleic acid amplification technologies for point-of-care diagnostics: a critical review, Lab on a Chip, vol. 12, No. 14, Jul. 1, 2012.
Dean et al. Rapid Amplification of Plasmid and Phase DNA Using Phi29 DNA Polymerase and Multiply-Primed Rolling Circle Amplification, Genome Research, Gold Spring Harbor Laboratory Press, US, vol. 11, No. 6, Jun. 1, 2001.
Euler et al. Recombinase polymerase amplification assay for rapid detection of Rift Valley fever virus. J Clin Virol. Aug. 2012;54(4):308-12. Epub Jun. 9, 2012.
Fire et al. Rolling replication of short DNA circles, Proceedings of the National Academy of Sciences, National Academy of Sciences, US, vol. 92, No. 10, May 1995.
G.J Hafner, et al. Isothermal Amplification and Multimerization of DNA by Bst DNA Polymerase. BioTechniques 30:852-867; Apr. 2001.

(56) References Cited

OTHER PUBLICATIONS

Horton et al. Engineering hybrid genes without the use of restriction enzymes: gene splicing byoverlap extension. Gene, Elsevier, Amsterdam, NL, vol. 77, No. 1, Apr. 15, 1989, pp. 61-68.
International Search Report and Written Opinion dated Aug. 14, 2014 for Application No. PCT/US2014/030028.
International Search Report and Written Opinion dated Aug. 14, 2014 for Application No. PCT/US2014/030036.
International Search Report and Written Opinion dated Sep. 18, 2014 for PCT/US2014/030034.
Lee et al. Versatile PCR-mediated insertion or deletion mutagenesis.
Liu et al. Rolling Circle DNA Synthesis: Small Circular Oligonucleotides as Efficient Templates for DNA Polymerases, Journal of the American Chemical Society, American Chemical Society, US, vol. 118, No. 7, 1996.
Lizardi et al. Mutation detection and single-molecule counting using isothermal rolling-circle amplification, Nature Genetics, Nature Publishing Group, New York, US, vol. 19, No. 3, Jul. 1998.
Marciniak et al. Coupled rolling circle amplification loop-mediated amplification for rapid detection of short DNA sequences, Biotechniques, 2008, 45:275-280.
Merriam-Webster, definition of "analogous", available at http://www.merriam-webster.com/dictionary/analogous, accessed May 18, 2015.
Merriam-Webster, definition of "partner", available at http://www.merriam-webster.com/dictionary/partner, accessed May 18, 2015.
Merriam-Webster, definition of "portion", available at http://www.merriam-webster.com/dictionary/portion, accessed May 18, 2015.
Merriam-Webster, definition of "represent", available at http://www.merriam-webster.com/dictionary/represent, accessed May 18, 2015.
Notice of Allowance dated Mar. 4, 2016 for U.S. Appl. No. 14/214,848.
Notice of Allowance dated Aug. 22, 2016 for U.S. Appl. No. 14/479,241.
Notice of Allowance dated Sep. 7, 2016 for U.S. Appl. No. 14/546,998.
Notomi et al. Loop-mediated isothermal amplification of DNA, Nucleic Acids Res. Jun. 15, 2000;28(12):E63.
Office Action dated Oct. 26, 2015 for U.S. Appl. No. 14/546,998.
Office Action dated Oct. 30, 2015 for U.S. Appl. No. 14/214,848.
Office Action dated Nov. 25, 2016 for U.S. Appl. No. 14/214,854.
Office Action dated Nov. 8, 2016 for U.S. Appl. No. 14/604,194.
Office Action dated Dec. 29, 2016 for U.S. Appl. No. 15/041,421.
Office Action dated Apr. 3, 2017 for U.S. Appl. No. 14/604,194.
Office Action dated May 11, 2016 for U.S. Appl. No. 14/546,998.
Office Action dated Jun. 8, 2015 for U.S. Appl. No. 14/546,998.
Office Action dated Jul. 6, 2016 for U.S. Appl. No. 14/546,998.
Office Action dated Sep. 1, 2017 for U.S. Appl. No. 15/041,421.
Office Action dated Sep. 27, 2016 for U.S. Appl. No. 14/214,850.
Ohshima K and Wells RD. Hairpin formation during DNA synthesis primer realignment in vitro in triplet repeat sequences from human hereditary disease genes. Journal of Biological Chemistry 272:16798-16806; Jul. 1997.
Patel R et al. Formation of chimeric DNA primer extension products by template switching onto an annealed downstream oligonucleotide. PNAS 93:2969-2974; Apr. 1996.
Rohrman et al. A Paper and Plastic Device for Performing Recombinase Polymerase Amplification of HIV DNA. Lab Chip, Sep. 7, 2012;12(17):3082-8. Epub Jun. 26, 2012.
Sharbati-Tehrani et al. Concatameric cloning of porcine microRNA molecules after assembly PCR. Biochemical and Biophysical Research Communications, Elsevier, Amsterdam, NL, vol. 375, No. 3, Oct. 24, 2008, pp. 484-489.
Wang et al. Rolling circle amplification-mediated hairpin RNA (RMHR) library construction in plants.
White et al. Concatemer Chain Reaction: a Taq DNA Polymerase-Mediated Mechanism for Generating Long Tandemly Repetitive DNA Sequences. Analytical Biochemistry, Academic Press Inc, New York, vol. 199, No. 2, Dec. 1, 1991, pp. 184-190.
Wilton SD et al. Snapback SSCP analysis: Engineered conformation changes for the rapid typing of known mutations. Human Mutation 11:252-258; Mar. 1998.
Written Opinion and International Search Report dated Dec. 25, 2014 for PCT/US2014/056151.
Notice of Allowance dated Oct. 26, 2017 for U.S. Appl. No. 14/604,194.
Office Action dated May 21, 2018 for U.S. Appl. No. 15/356,972.
Office Action dated Nov. 14, 2018 for U.S. Appl. No. 15/356,972.

\* cited by examiner

| Nosocomial Panel (HAI) | Respiratory Panel | | STD Panel (swab) |
|---|---|---|---|
| *Acinetobacter baumannii* | Adenovirus B | Influenza H7N9 - HA gene | *Candida albicans* |
| blaROB resistance gene | Adenovirus C | Influenza H7N9 - NA gene | *Chlamydia trachomatis* |
| blaTEM resistance gene | Adenovirus E | *Klebsiella pneumoniae* | HPV 16 |
| *Bordetella holmesii* | blaROB resistance gene | KPC resistance gene | HPV 18 |
| *Burkholderia cepacia* | blaTEM resistance gene | *Legionella pneumophila* | HSV-1/2 |
| *Candida albicans* | Bocavirus 1 + 3 | Measles virus | *Mycoplasma genitalium* |
| *Clostridium difficile* | Bocavirus 2 + 4 | mecA resistance gene | *Neisseria gonorrhoeae* |
| *Clostridium sordellii* | *Bordetella holmesii* | mecC resistance gene | *Streptococcus agalactiae* (Strep B) |
| *Enterobacter aerogenes* | *Bordetella parapertussis* | Mumps virus | *Treponema pallidum* (syphilis) |
| *Enterobacter cloacae* | *Bordetella pertussis* | *Mycobacterium tuberculosis* | *Trichomonas vaginalis* |
| *Enterococcus faecalis* | *Chlamydia pneumoniae* | *Mycoplasma pneumoniae* | Varicella-zoster virus |
| *Enterococcus faecium* | *Clostridium sordellii* | Parainfluenza 1 | |
| *Escherichia coli* | Coronavirus 229E | Parainfluenza 2 | STD Panel (blood) |
| *Klebsiella pneumoniae* | Coronavirus HKU1 | Parainfluenza 3 | Epstein-Barr Virus |
| KPC resistance gene | Coronavirus MERS | Parainfluenza 4a | Hepatitis A |
| *Legionella pneumophila* | Coronavirus NL63 | Parainfluenza 4b | Hepatitis B assay |
| mecA resistance gene | Coronavirus OC43 | Respiratory syncytial virus A (RSV A) | Hepatitis C |
| mecC resistance gene | *Haemophilus influenzae* | Respiratory syncytial virus B (RSV B) | HepDelta assay |
| *Moraxella catarrhalis* | *Haemophilus parainfluenzae* | Rhinovirus A | HIV-1 group M assay 1 |
| *Mycobacterium abscessus* | Human metapneumovirus A | Rhinovirus B | HIV-1 group M assay 2 |
| *Pseudomonas aeruginosa* | Human metapneumovirus B | Rhinovirus C | HIV-1 group O1 |
| *Serratia marcescens* | Influenza A - MP | Rubella virus | HIV-1 group O3 |
| Spike-in control | Influenza B - MP | *Staphylococcus aureus* | HIV-2 Group A |
| *Staphylococcus aureus* | Influenza H1N1 - novel (2009) | *Staphylococcus aureus* (Vancomycin-resistant) VRSA | HIV-2 Group B |
| *Staphylococcus aureus* (Vancomycin-resistant) VRSA | Influenza H1N1 - Seasonal | *Streptococcus pneumoniae* | |
| *Streptococcus agalactiae* (Strep B) | Influenza H3N2 | *Streptococcus pneumoniae* (penicillin-sensitive) | Urinary Tract Infection Panel |
| *Streptococcus pneumoniae* | Influenza H5N1 | *Streptococcus pyogenes* | *Enterococcus faecalis* |
| *Streptococcus pneumoniae* (penicillin-sensitive) | | | *Enterococcus faecium* |
| *Streptococcus pyogenes* | Infectious Disease Panel | | *Escherichia coli* |
| vanA resistance gene | Dengue Virus 1 | | *Klebsiella pneumonia* |
| vanB resistance gene | Dengue Virus 2 | | KPC resistance gene |
| Controls | Dengue Virus 3 | Gastrointestinal Panel | *Mycoplasma hominis* |
| Human RnaseP | Dengue Virus 4 | *Clostridium difficile* | *Proteus mirabilis* |
| Spike-in control | *Plasmodium* | *Escherichia coli* | *Proteus penneri* |
| Additional Assays | *Tryponosoma cruzi* (chagas) | Hepatitis A | *Proteus vulgaris* |
| *Bacillus anthracis* | West Nile Virus 1 | *Listeria monocytogenes* | *S. saprophyticus* |
| *Yersinia pestis* | West Nile Virus 2 | Norovirus lineage I | Spike-in control |
| | | Norovirus lineage II | *Ureaplasma urealyticum* |
| | | | vanA resistance gene |
| | | | vanB resistance gene |

Fig. 22

| Influenza Panel | Organism | LOD |
|---|---|---|
| | Influenza A | < 100 c/uL |
| | Influenza A H3N2 | < 10 c/uL |
| | Influenza A H5N1 | < 100 c/uL |
| | Influenza A H7N9 - HA gene | < 10 c/uL |
| | Influenza A H7N9 - NA gene | < 10 c/uL |
| | Influenza B | < 10 c/uL |
| | Influenza H1N1 novel (pdm09) | < 10 c/uL |
| | Influenza H1N1 seasonal | < 10 c/uL |

| Organism | LOD |
|---|---|
| | |
| Acinetobacter baumanii | < 10 c/uL |
| Adenovirus B | < 10 c/uL |
| Adenovirus C | < 10 c/uL |
| Adenovirus E | < 10 c/uL |
| blaROB, Haemophilus influenzae | < 10 c/uL |
| blaTEM, Haemophilus influenzae | < 10 c/uL |
| Bocavirus type 1, 3 | < 100 c/uL |
| Bocavirus type 2, 4 | < 10 c/uL |
| Bordetella holmesii | < 10 c/uL |
| Bordetella parapertussis | < 10 c/uL |
| Bordetella pertussis | < 4 c/uL |
| Burkholderia cepacia | < 10 c/uL |
| Chlamydophila pneumoniae | < 10 c/uL |
| Coronavirus 229E | < 10 c/uL |
| Coronavirus HKU1 | < 100 c/uL |
| Coronavirus MERS | < 100 c/uL |
| Coronavirus NL63 | < 10 c/uL |
| Coronavirus OC43 | < 100 c/uL |
| Enterobacter aerogenes | < 10 c/uL |
| Enterobacter cloacae | < 10 c/uL |
| Enterococcus faecalis | < 10 c/uL |
| Enterococcus faecium | < 10 c/uL |
| Group A Streptococcus | < 10 c/uL |
| Group B Streptococcus | < 10 c/uL |
| Haemophilus influenzae | < 10 c/uL |
| Haemophilus parainfluenzae | < 10 c/uL |
| HMPV-A | < 100 c/uL |
| HMPV-B | < 100 c/uL |
| Klebsiella pneumoniae KPC | < 10 c/uL |
| Klebsiella pneumoniae phoE | < 10 c/uL |
| Legionella pneumophila | < 10 c/uL |
| Moraxella catarrhalis | < 10 c/uL |
| MRSA | < 10 c/uL |
| MTB | < 10 c/uL |
| Mycobacterium abscessus | < 10 c/uL |
| Mycoplasma pneumoniae | < 10 c/uL |
| Parainfluenza Virus 1 | < 100 c/uL |
| Parainfluenza Virus 2 | < 100 c/uL |
| Parainfluenza Virus 3 | < 100 c/uL |
| Parainfluenza Virus 4a | < 100 c/uL |
| Parainfluenza Virus 4b | < 10 c/uL |
| PenS Streptococcus pneumoniae | < 10 c/uL |
| Pseudomonas aeruginosa | < 10 c/uL |
| RSV-A | < 100 c/uL |
| RSV-B | < 100 c/uL |
| Serratia marcescens | < 10 c/uL |
| Staphylococcus aureus | < 10 c/uL |
| Streptococcus pneumoniae | < 10 c/uL |
| Streptococcus pyogenes | < 10 c/uL |
| vanA, vancomycin resistant Enterococci | < 10 c/uL |
| vanB, vancomycin resistant Enterococci | < 10 c/uL |

(Respiratory Panel)

Fig. 24A

Upper and Lower Respiratory Panel

|  | Organism | LOD |
|---|---|---|
| HAI | Streptococcus pyogenes | < 10 c/uL |
|  | Acinetobacter baumanii | < 10 c/uL |
|  | blaROB, Haemophilus influenzae | < 10 c/uL |
|  | blaTEM, Haemophilus influenzae | < 10 c/uL |
|  | Burkholderia cepacia | < 10 c/uL |
|  | Chlamydophila pneumoniae | < 10 c/uL |
|  | Enterobacter aerogenes | < 10 c/uL |
|  | Enterobacter cloacae | < 10 c/uL |
|  | Enterococcus faecalis | < 10 c/uL |
|  | Enterococcus faecium | < 10 c/uL |
|  | Group A Streptococcus | < 10 c/uL |
|  | Group B Streptococcus | < 10 c/uL |
|  | Klebsiella pneumoniae KPC | < 10 c/uL |
|  | Klebsiella pneumoniae phoE | < 10 c/uL |
|  | Legionella pneumophila | < 10 c/uL |
|  | Moraxella catarrhalis | < 10 c/uL |
|  | MRSA | < 10 c/uL |
|  | Mycobacterium abscessus | < 10 c/uL |
|  | Mycoplasma pneumoniae | < 10 c/uL |
|  | PenS Streptococcus pneumoniae | < 10 c/uL |
|  | Pseudomonas aeruginosa | < 10 c/uL |
|  | Serratia marcescens | < 10 c/uL |
|  | Staphylococcus aureus | < 10 c/uL |
|  | vanA, vancomycin resistant Enterococci | < 10 c/uL |
|  | vanB, vancomycin resistant Enterococci | < 10 c/uL |

Fig. 25A

Influenza A – Matrix Protein assay: designed to be inclusive for all Influenza A subtypes.

Fig. 27

| STD Swab Interfering Substance Panel | | |
|---|---|---|
| Substance | 1x Concentration | 0.1x Concentration |
| 1 KY lubricant | 2.5% w/v | 0.25% w/v |
| 2 Options Gynol II Contraceptive Jelly (spermicide) | 2.5% w/v | 0.25% w/v |
| 3 Vagisil feminine powder | 2.5% w/v | 0.25% w/v |
| 4 Preparation H hemorrhoid cream | 2.5% w/v | 0.25% w/v |
| 5 Monistat 3 (miconazole) | 2.5% w/v | 0.25% w/v |
| 6 hgDNA | 200 ng/mL | 20 ng/mL |
| 7 Vagisil anti-itch cream | 2.5% w/v | 0.25% w/v |
| 8 Clotrimazole vaginal cream | 2.5% w/v | 0.25% w/v |
| 9 Universal transport media (viral) | 50% v/v | 5% v/v |
| 10 Amies transport media (bacteria) | 50% v/v | 5% v/v |
| 11 DNA/RNA Shield | 50% v/v | 5% v/v |
| 12 blood | 10% v/v | 1% v/v |
| 13 mucin | 2.5% w/v | 0.25% w/v |
| 14 acyclovir | 0.125% w/v | 0.013% w/v |
| 15 Abreva cold sore treatment | 2.5% w/v | 0.025% w/v |
| 16 urine | 50% v/v | 5% v/v |
| 17 feces (1 swab diluted in 1.2 mL) | 50% v/v | 5% v/v |

Potential Interfering Substances – STD Swab Panel

Fig. 29

| STD Urine Interfering Substance Panel | | |
|---|---|---|
| Substance | 1x Concentration | 0.1x Concentration |
| 1 BSA | 120 g/L | 12 g/L |
| 2 glucose | 10 mg/mL | 1 mg/mL |
| 3 bilirubin | 40 mg/dL | 4 mg/dL |
| 4 nitrites | 1354 µmol/L | 135.4 µmol/L |
| 5 beta-hCG | 300,000 mIU/mL | 30,000 mIU/mL |
| 6 acetone | 12 mmol/L | 1.2 mmol/L |
| 7 low pH urine (pH 4.0) | 50% v/v | 5% v/v |
| 8 high pH urine (pH 9.0) | 50% v/v | 5% v/v |
| 9 acetaminophen | 1.95 mg/mL | 0.195 mg/mL |
| 10 aspirin | 0.652 mg/mL | 0.065 mg/mL |
| 11 Bactrim | 308 µM | 30.8 µM |
| 12 progestin + ethinyl estradiol | 7 mg/mL + 0.07 mg/mL | 0.7 mg/mL + 0.007 mg/mL |
| 13 Abbott Multi-collect urine specimen transport buffer | 50% | 5% |
| 14 Gen-Probe Aptima urine specimen transport media | 50% | 5% |
| 15 Norgen Biotek urine preservative | 15% | 1.5% |
| 16 seminal fluid | 5% v/v | 0.5% v/v |

Potential Interfering Substances – STD Urine Panel

Fig. 30

| Blood Interfering Substance Panel | | |
|---|---|---|
| Substance | 1x Concentration | 0.1x Concentration |
| 1 hemoglobin | 5 g/L | 0.5 g/L |
| 2 triglycerides | 1430 mg/dL | 143 mg/dL |
| 3 BSA | 120 g/L | 12 g/L |
| 4 EDTA, pH 8.0 (anticoagulant) | 10 mg/mL | 1 mg/mL |
| 5 heparin sodium salt (anticoagulant) | 106 U/mL | 10.6 U/mL |
| 6 cholesterol | 13 mmol/L | 1.3 mmol/L |
| 7 γ-globulin | 60 g/L | 6 g/L |
| 8 universal transfer media (viral) | 50% v/v | 5% v/v |
| 9 Amies transfer media (bacteria) | 50% v/v | 5% v/v |
| 10 BACTEC™ Plus Anaerobic/F Medium | 50% v/v | 5% v/v |
| 11 BACTEC™ Standard/10 Aerobic/F Medium | 50% v/v | 5% v/v |
| 12 bilirubin | 684 μmol/L | 68.4 μmol/L |
| 13 hgDNA | 200 ng/mL | 20 ng/mL |
| 14 ampicillin sodium salt | 152 μmol/L | 15.2 μmol/L |
| 15 Bactrim (1:5 trimethoprim:sulfamethoxazole) | 308 μmol/L | 30.8 μmol/L |
| 16 azithromycin | 1.38 mg/mL | 0.138 mg/mL |
| 17 nicotine/cotinine | 6.2 μmol/L; 10.8 μmol/L | 0.62 μmol/L; 1.08 μmol/L |
| 18 DNA/RNA shield | 50% v/v | 5% v/v |

Potential Interfering Substances - Blood Panel

Fig. 31

SYSTEMS AND METHODS FOR DETECTING INFECTIOUS DISEASES

BACKGROUND

Infectious diseases, whether or bacterial, viral, or other origin, present acute and chronic challenges to human health. Many common infections affect the respiratory tract. Respiratory tract diseases, particularly infectious respiratory diseases of viral and bacterial origin, are prevalent in patients of all ages, although often are more serious in the very young and the very old. Viruses include DNA viruses and RNA viruses. Bacteria include Gram positive and Gram negative bacteria, and may include *mycoplasma* (bacteria lacking cell walls). In addition to disease-causing bacteria, some diseases, such as, e.g., respiratory diseases, may be caused by other microorganisms such as yeasts, fungi, and other small, disease-causing organisms.

An example of a common viral cause of respiratory (and other) disorders in patients is the influenza ("flu") virus. Influenza ("flu") refers to disease caused by one of several related RNA viruses of the Orthomyxoviridae family, typified by fever, headache, fatigue, and other symptoms. There are different types of influenza; influenza A and influenza B are both about equally prevalent in humans. Identification of the strain of flu in a sample can help suggest treatments, can help suggest preventive measures to be taken, and can help to track such infections in a population.

Examples of common bacterial causes of respiratory (and other) disorders in patients include whooping cough, pneumonia, and tuberculosis. Whooping cough is caused by *Bordetella pertussis* and is typified by fits of violent coughing, which may persist for weeks. Pneumonia is the name given to respiratory disorders characterized by fluid in the lungs, coughing, fever, vomiting, fatigue, and other symptoms. Pneumonia may be caused by bacterial or viral infection; determination of the cause of a particular case is critical in determining the course of treatment of the patient. Causes of pneumonia include *Streptococcus pneumonia*, *Staphylococcus aureus*, adenovirus, influenza viruses, respiratory syncytial virus, *Pneumocystis, jirovecii* (a fungus), and other agents. Tuberculosis is caused by *Mycobacterium tuberculosis*, is typified by cough including spitting up blood, chest pain, chills, fever, night sweats, and other symptoms, and may be fatal.

Agents that cause infectious respiratory diseases typically differ between upper respiratory tract diseases and lower respiratory tract disorders; thus, the variety or range of bacterial or viral agents found in patients suffering from upper respiratory disorders may be different than those bacterial or viral agents found in patients suffering from lower respiratory disorders. However, successful diagnosis and treatment of respiratory diseases often requires identification of disease-causing organisms present in a clinical sample obtained from a subject suffering, or suspected of suffering, from an infectious respiratory disorder. Differentiating between organisms typical of upper respiratory and those typical of lower respiratory disorders may also be critical in the successful diagnosis and treatment of respiratory diseases. In addition, identification of other symptoms and sequelae of respiratory disorders may aid the successful diagnosis and treatment of respiratory diseases.

Sexually transmitted diseases, whether viral or bacterial, or otherwise, present particular public health problems since some patients are reluctant to acknowledge the risks of, or possible exposure to, such diseases, and may be reluctant to be tested for these diseases. However, lack of testing and resulting lack of information regarding disease status may lead to increased spread of such diseases, and delays treatment for those affected.

Some diseases may be detected by blood tests (e.g., dengue virus, Epstein-Barr virus, trypanosomal diseases, *plasmodium* diseases, and others). Some diseases may be detected by analysis of swabs, or fluid obtained from swabs, such as throat swabs, nasal swabs, cheek swabs, or other swabs. Diseases may also be detected by analysis of urine samples, and other clinical samples.

In order to be effective in treating such infectious disorders, testing must be timely. However, present methods and systems for testing are often time-consuming, inconvenient for patients, may require sample collection methods or amounts that are painful or uncomfortable for patients, and may be expensive. Methods that require large amounts of sample, or that require incubation of a sample for a day or days, are often ineffective at timely detection or identification of the cause of a respiratory disorder, and thus may not be helpful in the diagnosis or treatment of infectious respiratory disorders.

In addition, many infectious respiratory disorders present many of the same, or similar symptoms, so that useful and effective testing requires testing for the presence of multiple agents, and of multiple kinds of agents (e.g., viral, bacterial, and fungal). However, present methods are often limited to testing for a single agent or kind of agent, or only a small number of possible agents, limiting the utility of the results and raising the likelihood that the causal agent may not be identified.

Thus, improved methods, systems, and assays for the detection and identification of agents that cause diseases, such as influenza, respiratory diseases, sexually transmitted diseases, blood diseases, viral diseases, bacterial diseases, and other diseases, are desired.

INCORPORATION BY REFERENCE

All publications, patents, and patent applications mentioned in this specification are herein incorporated by reference to the same extent as if each individual publication, patent, or patent application was specifically and individually indicated to be incorporated by reference.

SUMMARY

Systems, methods, and devices for detecting the presence of markers indicative of one or more of a plurality of infectious agents in a single clinical sample, or in a plurality of aliquots of a single clinical sample, are provided. The systems, methods, and devices disclosed herein may be point-of-service systems, methods, and devices, configured for use at a point-of-service location, where a point-of-service location may be a location at which a sample is obtained from a subject.

In embodiments, Applicants disclose systems, methods, and devices for testing for presence of one or more of a plurality of markers indicative of an infectious disease in a single small-volume clinical sample, or aliquots thereof. In embodiments, the system, method, or device is a point-of service (POS) system, method or device. In embodiments, the sample is collected at the POS location, and is analyzed in a device at the POS location. In embodiments, the analysis of the small-volume clinical sample is completed in a short period of time. In embodiments, the infectious disease comprises a respiratory disease. In embodiments, the infectious disease comprises a respiratory disease selected from an upper respiratory disease and a lower respiratory disease. In embodiments, the infectious disease comprises a sexually transmitted disease.

In embodiments, Applicants disclose systems, methods, and devices for detecting the presence of one or more of a plurality of markers indicative of an infectious disease in a single small-volume clinical sample, or aliquots thereof. In embodiments, the system, method or device is a POS system, method or device. In embodiments, the sample is collected at the POS location, and is analyzed in a device at the POS location. In embodiments, the analysis of the small-volume clinical sample is completed in a short period of time.

In embodiments, the infectious disease is a bacterial disease, or a viral disease, or another type of disease, and the analysis of the small-volume clinical sample determines whether the infectious disease is a bacterial disease, a viral disease, or another type of disease. The determination of the type of infectious disease aids in determining the type of treatment to provide to the subject, e.g., where the determination indicates the infectious disease is a fungal disease, the subject should be treated with anti-fungal drugs; where the determination indicates the infectious disease is a yeast infection, the subject should be treated with anti-yeast drugs; and so forth.

In embodiments, the infectious disease is a bacterial disease. In embodiments, the analysis of the small-volume clinical sample determines whether the infectious disease is a bacterial disease. In embodiments where the analysis of the small-volume clinical sample determines that the infectious disease is a bacterial disease, said determination indicates the use of antibiotics in the treatment of that disease. In embodiments, the infectious disease is a viral disease. In embodiments, the analysis of the small-volume clinical sample determines whether the infectious disease is a viral disease. In embodiments where the analysis of the small-volume clinical sample determines that the infectious disease is a viral disease, said determination indicates the use of antiviral drugs in the treatment of that disease. In embodiments where the analysis of the small-volume clinical sample determines that the infectious disease is a viral disease, said determination indicates that antibiotics should not be used in the treatment of that disease. In embodiments, the infectious disease is a bacterial disease, or a viral disease. In embodiments, the analysis of the small-volume clinical sample determines whether the infectious disease is a bacterial disease or a viral disease. Similarly, where the analysis of the small volume clinical sample determines the infectious disease is a fungal disease, the subject should be treated with anti-fungal drugs; where the determination indicates the infectious disease is a yeast infection, the subject should be treated with anti-yeast drugs; and so forth.

In embodiments, the infectious disease comprises a respiratory disease. In embodiments, the infectious disease comprises a respiratory disease selected from an upper respiratory disease and a lower respiratory disease. In embodiments, the analysis of the small-volume clinical sample determines whether the infectious disease is an upper respiratory disease or a lower respiratory disease. In embodiments, the analysis of the small-volume clinical sample determines the type of upper respiratory disease or a lower respiratory disease present in the small volume clinical sample. For example, in embodiments, the upper or lower respiratory disease is a bacterial disease, or a viral disease, or another type of disease, and the analysis of the small-volume clinical sample determines whether the upper or lower respiratory disease is a bacterial disease, a viral disease, or another type of disease. In embodiments where the analysis of the small-volume clinical sample determines that the upper or lower respiratory disease is a bacterial disease, said determination indicates the use of antibiotics in the treatment of that disease. In embodiments where the analysis of the small-volume clinical sample determines that the upper or lower respiratory disease is a viral disease, said determination indicates the use of antiviral drugs in the treatment of that disease. In embodiments where the analysis of the small-volume clinical sample determines that the upper or lower respiratory disease is a viral disease, said determination indicates that antibiotics should not be used in the treatment of that disease. Similarly, where the analysis of the small volume clinical sample determines the upper or lower respiratory disease is a fungal disease, the subject should be treated with anti-fungal drugs; where the determination indicates the infectious disease is a yeast infection, the subject should be treated with anti-yeast drugs; and so forth.

In embodiments, the infectious disease comprises a sexually transmitted disease. In embodiments, the analysis of the small-volume clinical sample determines the type of sexually transmitted disease present in the small volume clinical sample. For example, in embodiments, the sexually transmitted disease is a bacterial disease, or a viral disease, or another type of disease, and the analysis of the small-volume clinical sample determines whether the sexually transmitted disease is a bacterial disease, a viral disease, or another type of disease. In embodiments where the analysis of the small-volume clinical sample determines that the sexually transmitted disease is a bacterial disease, said determination indicates the use of antibiotics in the treatment of that disease. In embodiments where the analysis of the small-volume clinical sample determines that the sexually transmitted disease is a viral disease, said determination indicates the use of antiviral drugs in the treatment of that disease. In embodiments where the analysis of the small-volume clinical sample determines that the sexually transmitted disease is a viral disease, said determination indicates that antibiotics should not be used in the treatment of that disease. Similarly, where the analysis of the small volume clinical sample determines the sexually transmitted disease is a fungal disease, the subject should be treated with anti-fungal drugs; where the determination indicates the infectious disease is a yeast infection, the subject should be treated with anti-yeast drugs; and so forth.

In embodiments of the systems, methods, and devices configured for testing for a plurality of markers, and in systems, methods or devices configured for detecting a plurality of markers, the markers may be indicative of respiratory diseases; in embodiments, the markers may be indicative of upper respiratory diseases; in embodiments, the markers may be indicative of lower respiratory diseases. In embodiments, Applicants disclose systems, methods and devices configured for testing for a plurality of markers, wherein the respiratory disease markers are indicative of two or more of the group of respiratory disease markers consisting of adenovirus B, adenovirus C, adenovirus E, *Bordetella pertussis, mycobacterium tuberculosis* (MTB), *Staphylococcus aureus*, Methicillin-Resistant *Staphylococcus aureus* (MRSA), Group A *streptococcus*, and Group B *streptococcus*. In embodiments, Applicants disclose systems, methods and devices configured for testing for a plurality of markers, wherein the respiratory disease markers are indicative of two or more of the group of respiratory disease markers consisting of adenovirus B, adenovirus C, adenovirus E, *Bordetella pertussis, Bordetella parapertus-*

*sis, mycobacterium tuberculosis* (MTB), *Staphylococcus aureus*, Methicillin-Resistant *Staphylococcus aureus* (MRSA), Group A *streptococcus*, Group B *streptococcus, Moraxella catarrhais, Enterobacter aerogenes, Haemophilus parainfluenzae,* Metapneumo Virus, *Streptococcus pneumonia*, Parainfluenza Virus 1, Parainfluenza Virus 2, Parainfluenza Virus 3, Coronavirus OC43, Coronavirus NL63, Coronavirus MERS, Coronavirus HKU1, Coronavirus 229E, *Klibsiella* pneumonia phoE, *Klebsiella* pneumonia KPC, Bocavirus type 2,4, and Bocavirus type 1,3. In embodiments, the respiratory disease markers are indicative of three or more, or of four or more, or of five or more, or of six or more, or of seven or more, or of eight of that group of respiratory disease markers.

In embodiments of the systems, methods, and devices configured for testing for a plurality of markers, and in systems, methods, and devices configured for detecting a plurality of markers, the markers may be indicative of sexually transmitted diseases. In embodiments, Applicants disclose systems, methods, and devices configured for testing for a plurality of markers, wherein the sexually transmitted disease markers are indicative of two or more of the group of markers consisting of herpes simplex virus (HSV), human immunodeficiency virus (HIV), *streptococcus* B, and *treponema pallidum*. In embodiments, Applicants disclose systems, methods, and devices configured for testing for a plurality of markers, wherein the sexually transmitted disease markers are indicative of two or more of the group of markers consisting of HIV-2 Group A, HIV-2, Group B, HIV-1 Group M, Hepatitis B, Hepatitis Delta, herpes simplex virus (HSV), *streptococcus* B, and *treponema pallidum*. In embodiments, the sexually transmitted disease markers are indicative of three or more, or four of that group of sexually transmitted disease markers.

In embodiments of the systems, methods, and devices configured for testing for a plurality of markers, and in systems, methods, and devices configured for detecting a plurality of markers, the markers may be indicative of influenza. In embodiments, Applicants disclose systems, methods, and devices configured for testing for a plurality of markers, wherein the influenza markers are indicative of influenza A and of influenza B. In embodiments, Applicants disclose systems, methods, and devices configured for testing for a plurality of markers, wherein the influenza markers are indicative of two or more of the group of markers consisting of the following forms of influenza: H1N1 (seasonal), H1N1 (novel), H3N2, H7N9 (hemagglutinin gene marker (HA) and neuraminidase gene (NA)), and H5N1. In embodiments, the influenza markers are indicative of three or more, or four or more, or five of that group of influenza markers. In embodiments, the influenza markers may be influenza Matrix Protein markers, or may be influenza neuraminidase protein markers, or may be influenza hemagglutinin markers, or other influenza markers. In embodiments, the analysis of the small-volume clinical sample determines whether the infectious disease is an influenza. In embodiments, the analysis of the small-volume clinical sample determines the type of influenza present in the small volume clinical sample. In embodiments where the analysis of the small-volume clinical sample determines that the infectious disease is an influenza (which is a viral disease), said determination indicates that antibiotics should not be used in the treatment of that disease. In embodiments where the analysis of the small-volume clinical sample determines that the infectious disease is an influenza, said determination indicates that antiviral drugs should be used in the treatment of that disease.

In embodiments of the systems, methods, and devices configured for testing for a plurality of markers, and in systems, methods, and devices configured for detecting a plurality of markers, the markers may be indicative of diseases and disease markers which may be detected by analysis of a blood sample. In embodiments, such diseases and disease markers which may be detected by analysis of a blood sample include West Nile Virus, Epstein-Barr Virus, *plasmodium, Trypanosoma cruzi,* and Dengue Virus (including types 1, 2, 3, and 4).

Samples from the throat of a subject may be obtained, e.g., by a throat swab; samples obtained from the nose of a subject may be obtained, e.g., by a nasal swab. In embodiments, samples obtained from the throat and from the nose of a subject may be tested together. In embodiments, testing of samples obtained from the throat, or from the nose, or from both the nose and from the throat, may be tested by nucleic acid analysis; or by amino acid analysis (e.g., ELISA or other antibody-based or binding protein-based analysis); or by general chemistry analysis; or by cytometric analysis; or by combinations thereof. For example, samples may be tested by nucleic acid analysis and by amino acid analysis. Such tests may be used to determine how long a subject has had an infection, for example, by noting the delay in rise of levels of antibodies indicative of a particular disease in the sample; or by tracking the rise in the levels of antibodies indicative of a particular disease in the sample over time (e.g., by repeated testing over time). Similarly, such testing may be used to detect, or to determine, the effect of treatment, by noting the delay in rise of levels of antibodies indicative of a particular disease in the sample; or by tracking the rise in the levels of antibodies indicative of a particular disease in the sample over time (e.g., by repeated testing over time). In embodiments, samples from throat and from nose may be included in a single solution, and tested together. In embodiments, samples from throat and from nose may be in separate vessels (e.g., sample containers), but both included in a single cartridge, and the separate vessels tested at the same time. Such testing at the same time may comprise testing the vessels separately, or may include mixing the contents of the vessels and testing the mixture.

In embodiments, Applicants disclose systems, methods, and devices configured for identifying, or estimating, or otherwise determining the stage of an infection in a subject by detecting, or determining the amounts of, or both, both nucleic acid markers indicative of a particular infection and antibody markers indicative of the same infection. Such systems, methods, and devices may be used to detect, measure, and track such markers over time, effective to provide an estimate or determination of how recently an infection occurred. Such systems, methods, and devices may be used to detect, measure, and track such markers over time, effective to aid in evaluating the present status of a subject suffering from an infection. Such systems, methods, and devices may be used to detect, measure, and track such markers over time, effective to aid in determining the likely prognosis of a subject suffering from an infection. For example, where nucleic acid markers indicative of a particular infection are relatively numerous, while antibody or other protein markers indicative of that particular infection are relatively sparse, then it can be estimated or determined that the infection is a recent infection; however, where nucleic acid markers indicative of a particular infection are relatively numerous, and antibody or other protein markers indicative of that particular infection are also relatively numerous, then it can be estimated or determined that the infection is not a recent infection, since the subject has had the time to produce infection-specific antibodies. Where nucleic acid markers indicative of a particular infection are relatively sparse, and antibody or other protein markers indicative of that particular infection are also relatively numerous, then it can be estimated or determined that the infection in a late stage, and indicates that the infection is waning, since such observations indicate that the subject is overcoming the infection.

In embodiments, Applicants disclose systems, methods, and devices configured for testing for a plurality of markers, and disclose systems configured for detecting a plurality of markers, where the markers are indicative of a plurality of infectious diseases in a single small-volume clinical sample, or aliquots thereof. In embodiments, the systems, methods, and devices may be configured for testing for, or for detecting, markers indicative of more than about 8 different diseases, or more than about 8 different diseases, or more than about 12 different diseases, or more than about 16 different diseases, or more than about 20 different diseases, or more than about 25 different diseases, or more than about 35 different diseases, or more than about 45 different diseases, or more than about 60 different diseases. In embodiments, the systems, methods, and devices may be configured to test for, or to detect a plurality of nucleic acid markers and protein markers, each marker being indicative of at least one of a plurality of diseases or conditions. In embodiments, the systems, methods, and devices may be configured to test for, or to detect a plurality of nucleic acid markers, protein markers, and cytometric markers, each marker being indicative of at least one of a plurality of diseases or conditions. In embodiments, the systems, methods, and devices may be configured to test for, or to detect a plurality of nucleic acid markers, protein markers, cytometric markers, cytokines, and markers of inflammation, each marker or cytokine being indicative of at least one of a plurality of diseases or conditions. In embodiments, the systems, methods, and devices comprise a point-of service system. In embodiments, the sample may be collected at the point of service, and may be analyzed in a device at the POS location. In embodiments, the analysis of the small-volume clinical sample may be completed in a short period of time.

In embodiments, the infectious disease comprises a respiratory disease. In embodiments, the infectious disease comprises a respiratory disease selected from an upper respiratory disease and a lower respiratory disease. In embodiments, the analysis of the small-volume clinical sample determines whether the infectious disease is an upper respiratory disease or a lower respiratory disease. In embodiments, the analysis of the small-volume clinical sample determines the type of upper respiratory disease or a lower respiratory disease present in the small volume clinical sample. In embodiments, the respiratory disease comprises a respiratory disease caused by a disease-causing agent selected from a virus, a bacterium, a yeast, a fungus, a *mycoplasma*, and other micro-organisms. In embodiments, the analysis of the small-volume clinical sample determines the type of upper respiratory disease or a lower respiratory disease present in the small volume clinical sample. In embodiments, the analysis of the small-volume clinical sample determines whether the upper respiratory disease or a lower respiratory disease is a viral disease, or a bacterial disease, or some other type of disease. In embodiments in which the analysis of the small-volume clinical sample determines that the disease is a viral disease, said determination indicates that antibiotics should not be used in the treatment of that disease. In embodiments where the analysis of the small-volume clinical sample determines that the disease is a viral disease, said determination indicates that antiviral drugs should be used in the treatment of that disease. In embodiments in which the analysis of the small-volume clinical sample determines that the disease is a bacterial disease, said determination indicates that antibiotics should be used in the treatment of that disease.

In embodiments, the infectious disease comprises a sexually transmitted disease. In embodiments, the sexually transmitted disease comprises a sexually transmitted disease caused by a disease-causing agent selected from a virus, a bacterium, a yeast, a fungus, a *mycoplasma*, and other micro-organisms. In embodiments, the analysis of the small-volume clinical sample determines the type of sexually transmitted disease present in the small volume clinical sample. In embodiments, the analysis of the small-volume clinical sample determines whether the sexually transmitted disease is a viral disease, or a bacterial disease, or some other type of disease. In embodiments in which the analysis of the small-volume clinical sample determines that the disease is a viral disease, said determination indicates that antibiotics should not be used in the treatment of that disease. In embodiments where the analysis of the small-volume clinical sample determines that the disease is a viral disease, said determination indicates that antiviral drugs should be used in the treatment of that disease. In embodiments in which the analysis of the small-volume clinical sample determines that the disease is a bacterial disease, said determination indicates that antibiotics should be used in the treatment of that disease.

Applicant further discloses a method of determining the state of response to a disease in a subject, the method comprising: a) introducing a clinical sample into a sample processing device, said sample having been obtained from a subject suspected of suffering from a disease caused by a disease-causing organism, said clinical sample having a volume of no greater than 500 microliters, wherein the device comprises: i) a sample handling system; ii) a detection station; and iii) an assay station comprising at least a first and a second independently movable assay unit; b) with the aid of the sample handling system, transferring a portion of the clinical sample to each of the first and second assay units, wherein an assay for the detection of a nucleic acid indicative of the disease-causing organism is performed in said first assay unit, and an assay for the detection of antibodies to the disease-causing organism is performed in the second assay unit; c) transferring the first and second assay units to the detection station with the aid of the sample handling system; d) obtaining data measurements with the aid of the detection station, said data measurements comprising determining the level of nucleic acid indicative of a disease organism in the sample, and determining the level of antibodies directed to that disease organism in the sample; and e) i) determining that the infection is a recent infection, and in an early stage of the disease, where the level of nucleic acid indicative of a disease organism is high and the level of antibodies directed to that disease organism is low or normal; ii) determining that the infection is not a recent infection, and not in an early stage of the disease, where the level of nucleic acid indicative of a disease organism is high and the level of antibodies directed to that disease organism is high; and iii) determining that the infection is a waning infection, and in a late stage of the disease, where the level of nucleic acid indicative of a disease organism is low or normal and the level of antibodies directed to that disease organism is high, where a normal level of a marker is the level of that marker determined in a healthy population of normal subjects, where a high level is one that significantly exceeds a normal level as determined in a healthy population, and a low level is one that is at or below the normal level as determined in a healthy population.

In embodiments, the method of determining the state of response to a disease in a subject further comprises detecting the level of inflammatory cytokines. In embodiments of the method of determining the state of response to a disease in a subject, the device further comprises a cytometry station comprises an imaging device and a stage for receiving a microscopy cuvette, and the method further comprises imaging a white blood cell in a blood sample obtained from the subject. In embodiments, imaging a white blood cell in a blood sample obtained from the subject comprises detecting the level of a white blood cell type in a blood sample obtained from the subject, and determining whether said detected level of said type of white blood cell is above, at, or below a normal level for that type of blood cell, wherein the normal level for that type of white blood cell is determined by the level of that type of white blood cell in blood samples from a healthy population.

Tests may be for the detection of markers indicative of any infectious disease. For example, diseases that may be tested for include respiratory diseases, and include upper respiratory diseases and lower respiratory diseases. Markers may include nucleic acid markers, protein markers, polysaccharide markers, cellular markers (including cells and cellular organelles or fragments), and other markers. Markers may include markers for viral infections, bacterial infections, fungal infections, yeast infections, *mycoplasma* infections, and for other infections. Samples may be tested for markers indicative of inflammation. Samples may be tested for cytokines Samples may be tested for inflammatory cytokines. Samples may be tested for anti-inflammatory cytokines. The amount of dilution of a sample, or a level of detection of a marker, may be determined by the condition or past history of a subject.

Test results may be obtained within three hours, or two hours, or one hour, or ½ hour, or less from the time a sample is placed in a testing device for analysis. A sample may be placed in a testing device for analysis within five hours, or four hours, or three hours, or two hours, or one hour, or ½ hour, or less from the time a sample was obtained from a subject. Test results may be obtained within eight hours, seven hours, or six hours, or five hours, or three hours, or two hours, or one hour, or ½ hour, or less from the time a sample was obtained from a subject.

In embodiments, Applicant discloses a method of detecting a disease marker, comprising: a) introducing a cartridge comprising one or more samples into an automatic sample processing device, said cartridge being configured to hold at least one sample and being configured to hold a swab, wherein said automatic sample processing device comprises: i) a sample handling system configured to transport at least a portion of a sample and being configured to transport an independently movable assay unit; and ii) an optical detector; b) contacting a sample, or a portion thereof, with a movable assay unit, or a reagent, or both, for the performance of an assay for the detection of a disease marker, said contacting comprising transporting, with the aid of said sample handling system, at least a portion of said sample, or a movable assay unit, or a reagent, or combinations thereof; c) positioning said sample, or portion thereof, at a location suitable for detection of an optical signal from the sample or portion thereof by said optical detector; and d) detecting the presence of a disease marker. In embodiments, such a method may comprise performing two or more assays for the detection of disease markers, and detecting two or more disease markers in said one or more samples, or in one or more portions thereof. In embodiments, the sample has a volume of less than about 500 microliters (µL). In embodiments, the one or more samples comprises a blood sample; or comprises a sample obtained using a swab; or comprises both a blood sample and a sample obtained using a swab. In embodiments, a sample obtained using said swab may be obtained by swabbing a mouth, a throat, a nasal passage, a vaginal area, or other body cavity of a subject. In embodiments, the method comprises detecting the presence of a nucleic acid disease marker and a protein disease marker.

The methods disclosed herein include performing two or more assays for the detection of disease markers, and detecting two or more disease markers in said samples, or in one or more portions thereof. In embodiments, the methods comprise detecting the presence of a nucleic acid disease marker and a protein disease marker. In embodiments, the disease marker is selected from a nucleic acid disease marker, a protein disease marker, a saccharide, a prostaglandin, a cytokine, histamine, a steroid, and a marker for inflammation. In embodiments, two or more disease markers are detected, wherein the disease markers are selected from a nucleic acid disease marker, a protein disease marker, a saccharide, a prostaglandin, a cytokine, histamine, a steroid, and a marker for inflammation. In embodiments, a disease marker is a marker for inflammation selected from prostaglandins, tumor necrosis factor alpha (TNF-α), interleukin-1 (IL-1), interleukin-8 (IL-8), interleukin-12 (IL-12), interferon gamma (IF-γ), bradykinin, complement system molecules, blood-clotting factors, C-reactive protein, erythrocyte sedimentation rate (ESR), white blood cell count, and morphological changes in blood and other cells.

In embodiments, a disease marker is a marker for a disease-causing agent, wherein said disease-causing agent is selected from the group of disease-causing organisms consisting of a virus, a bacterium, a mycoplasm, a fungus, a yeast, and other micro-organisms. In embodiments, a disease marker for a disease-causing agent is selected from the group consisting of Influenza A Matrix protein, Influenza H3N2, Influenza H1N1 seasonal, Influenza H1N1 novel, Influenza B, *Streptococcus pyogenes* (A), *Mycobacterium Tuberculosis*, *Staphylococcus aureus* (MR), *Staphylococcus aureus* (RS), *Bordetella pertussis* (whooping cough), *Streptococcus agalactiae* (B), Influenza H5N1, Influenza H7N9, Adenovirus B, Adenovirus C, Adenovirus E, Hepatitis b, Hepatitis c, Hepatitis delta, *Treponema pallidum*, HSV-1, HSV-2, HIV-1, HIV-2, Dengue 1, Dengue 2, Dengue 3, Dengue 4, Malaria, West Nile Virus, *Trypanosoma cruzi* (Chagas), *Klebsiella pneumoniae* (Enterobacteriaceae spp), *Klebsiella pneumoniae* carbapenemase (KPC), Epstein Barr Virus (mono), Rhinovirus, Parainfluenza virus (1), Parainfluenza virus (2), Parainfluenza virus (3), Parainfluenza virus (4a), Parainfluenza virus (4b), Respiratory syncytial virus (RSV) A, Respiratory syncytial virus (RSV) B, Coronavirus 229E, Coronavirus HKU1, Coronavirus OC43, Coronavirus NL63, Novel Coronavirus, Bocavirus, human metapneumovirus (HMPV), *Streptococcus pneumoniae* (penic R), *Streptococcus pneumoniae* (S), *Mycoplasma pneumoniae*, *Chlamydia pneumoniae*, *Bordetella parpertussis*, *Haemophilus influenzae* (ampic R), *Haemophilus influenzae* (ampic S), *Moraxella catarrhalis*, *Pseudomonas* spp (*aeruginosa*), *Haemophilus parainfluenzae*, *Enterobacter cloacae* (Enterobacteriaceae spp), *Enterobacter aerogenes* (Enterobacteriaceae spp), *Serratia marcescens* (Enterobacteriaceae spp), *Acinetobacter baumanii*, *Legionella* spp, *Escherichia* coli, Candida, Chlamydia trachomatis, Human Papilloma Virus, Neisseria gonorrhoeae, plasmodium, and Trichomonas (vagin).

In embodiments, the methods comprise detecting a disease marker in a blood sample and detecting a disease marker in a sample obtained from a swab, wherein one of said disease markers is a marker for inflammation, and one of said disease markers a marker for a disease-causing agent. In embodiments, such a disease marker for inflammation is selected from prostaglandins, tumor necrosis factor alpha (TNF-α), interleukin-1 (IL-1), interleukin-8 (IL-8), interleukin-12 (IL-12), interferon gamma (IF-γ), bradykinin, complement system molecules, blood-clotting factors, C-reactive protein, erythrocyte sedimentation rate (ESR), white blood cell count, and morphological changes in blood and other cells, and such a disease marker for a disease-causing agent is selected from the group of disease-causing organisms consisting of a virus, a bacterium, a mycoplasm, a fungus, a yeast, and other micro-organisms.

In embodiments, a disease marker is a marker for a disease selected from influenza, a respiratory disease, a sexually transmitted disease, and another infectious disease. In embodiments where the disease is influenza, the disease marker is selected from H1N1 (seasonal), H1N1 (novel), H3N2, H7N9, and H5N1. In embodiments, the disease is respiratory disease selected from an upper respiratory disease and a lower respiratory disease. In embodiments where the disease is a respiratory disease, the marker may be a marker for a disease-causing organism selected from the group consisting of adenovirus B, adenovirus C, adenovirus E, Bordetella pertussis, mycobacterium tuberculosis (MTB), Staphylococcus aureus, Methicillin-Resistant Staphylococcus aureus (MRSA), Group A streptococcus, Group B streptococcus, Moraxella catarrhalis, Enterobacter aerogenes, Haemophilus parainfluenzae, Metapneumo Virus, Streptococcus pneumonia, Parainfluenza Virus 1, Parainfluenza Virus 2, Parainfluenza Virus 3, Coronavirus OC43, Coronavirus NL63, Coronavirus MERS, Coronavirus HKU1, Coronavirus 229E, Klibsiella pneumonia phoE, Klebsiella pneumonia KPC, Bocavirus type 2,4, and Bocavirus type 1,3.

In embodiments where the disease is a sexually transmitted disease, the marker may comprise a marker for a disease-causing organism indicative of a sexually transmitted disease selected from herpes simplex virus (HSV), human immunodeficiency virus (HIV), HIV-2 Group A, HIV-2 Group B, HIV-1 Group M, Hepatitis B, Hepatitis Delta, herpes simplex virus (HSV), streptococcus B, and treponema pallidum.

In embodiments, the method comprises detecting a disease marker in a blood sample and detecting a disease marker in a sample obtained from a swab, wherein at least one of said disease markers is a marker for a disease-causing organism indicative of a respiratory disease selected from the group consisting of adenovirus B, adenovirus C, adenovirus E, Bordetella pertussis, mycobacterium tuberculosis (MTB), Staphylococcus aureus, Methicillin-Resistant Staphylococcus aureus (MRSA), Group A streptococcus, Group B streptococcus, Moraxella catarrhalis, Enterobacter aerogenes, Haemophilus parainfluenzae, Metapneumo Virus, Streptococcus pneumonia, Parainfluenza Virus 1, Parainfluenza Virus 2, Parainfluenza Virus 3, Coronavirus OC43, Coronavirus NL63, Coronavirus MERS, Coronavirus HKU1, Coronavirus 229E, Klibsiella pneumonia phoE, Klebsiella pneumonia KPC, Bocavirus type 2,4, and Bocavirus type 1,3.

In embodiments where the disease is an infectious disease, the disease marker may comprise a marker for an infectious disease-causing agent selected from the group consisting of West Nile Virus, Epstein-Barr Virus, plasmodium, Trypanosoma cruzi, and a Dengue Virus.

In embodiments comprising detecting a disease marker in a blood sample and detecting a disease marker in a sample obtained from a swab, wherein at least one of said disease markers is a marker for a disease-causing organism indicative of a sexually transmitted disease selected from herpes simplex virus (HSV), human immunodeficiency virus (HIV), HIV-2 Group A, HIV-2 Group B, HIV-1 Group M, Hepatitis B, Hepatitis Delta, herpes simplex virus (HSV), streptococcus B, and treponema pallidum.

In embodiments comprising detecting a disease marker in a blood sample and detecting a disease marker in a sample obtained from a swab, wherein at least one of said disease markers is a marker for a disease-causing agent selected from the group consisting of West Nile Virus, Epstein-Barr Virus, plasmodium, Trypanosoma cruzi, and a Dengue Virus.

In embodiments of the methods of detecting a disease marker, the method is a point-of service method performed at a point-of-service location. In embodiments of methods of detecting a disease marker, the method may be performed in less than about 40 minutes. In embodiments comprising detecting a disease marker in a blood sample and detecting a disease marker in a sample obtained from a swab, the method is a point-of service method performed at a point-of-service location. In embodiments comprising detecting a disease marker in a blood sample and detecting a disease marker in a sample obtained from a swab, the method may be performed in less than about 40 minutes.

For example, Applicant discloses herein a method of determining the stage of an infection in a subject suffering from an infection, comprising: Testing at least one sample, or an aliquot or aliquots thereof, obtained from said subject 1) for the presence of a nucleic acid indicative of the infection, and 2) for the presence of an antibody indicative of the infection, and Determining whether the relative amounts of a) nucleic acids indicative of the infection and b) antibodies indicative of the infection indicate that the infection is a recent infection, wherein i) a greater relative amount of the nucleic acids indicative of the infection as compared to the relative amount of the antibodies indicative of the infection indicate that the infection is a recent infection, and ii) a significant amount of antibodies to the infectious agent indicate the infection is not a recent infection. In embodiments of such a method, the at least one sample comprises a blood sample. In embodiments of such a method, the at least one sample comprises a sample selected from a throat swab sample, a cheek swab sample, nasal swab sample, a saliva sample, and a blood sample. In embodiments of such a method, where a significant amount of antibody to the infectious agent is detected, and where nucleic acid markers indicative of the infectious agent are relatively sparse, then the method indicates that the infection is in a late stage and that the infection is waning.

In embodiments, such a method may further include testing a sample or samples for a marker for inflammation. In embodiments, the marker for inflammation may be selected from a prostaglandin, tumor necrosis factor alpha (TNF-α), interleukin-1 (IL-1), interleukin-8 (IL-8), interleukin-12 (IL-12), interferon gamma (IF-γ), bradykinin, a complement system molecule, a blood-clotting factor, and a morphological change in a blood or other cell. In embodiments, the marker for inflammation is a cytokine selected from a lymphokine, a chemokine, an interleukin, and an interferon.

In embodiments, a method disclosed herein comprises testing to determine whether the subject suffers from a bacterial infection, a viral infection, a yeast infection, a *mycoplasma* infection, a fungal infection, other infection, or combination thereof. In embodiments, such testing comprises determining whether markers indicative of viral infection or markers indicative of bacterial infection are detected, effective to determine whether the subject suffers from a bacterial infection or a viral infection.

In embodiments of the methods disclosed herein, the methods further comprise prescribing a prescription suitable for treatment of the infection. In embodiments, methods disclosed herein comprise providing a prescription suitable for treatment of said infection comprises prescription of an antibiotic when the testing determines that the subject suffers from a bacterial infection. In embodiments, methods disclosed herein comprise providing a prescription suitable for treatment of said infection comprises the prescription of an anti-mycoplasmal drug when the testing determines that the subject suffers from a mycoplasmal infection. In embodiments, methods disclosed herein comprise providing a prescription suitable for treatment of said infection comprises the prescription of an anti-viral drug when the testing determines that the subject suffers from a viral infection. In embodiments, methods disclosed herein comprise providing a prescription suitable for treatment of said infection comprises avoiding the prescription of an antibiotic, when the testing determines that the subject suffers from a viral infection. In embodiments, methods disclosed herein comprise providing a prescription suitable for treatment of said infection comprises avoiding the prescription of an antibiotic, and providing the prescription of an anti-viral drug, when the testing determines that the subject suffers from a viral infection. In embodiments, methods disclosed herein comprise providing a prescription suitable for treatment of said infection comprises the prescription of an anti-fungal drug when the testing determines that the subject suffers from a fungal infection. In embodiments, methods disclosed herein comprise providing a prescription suitable for treatment of said infection comprises the prescription of an anti-yeast drug when the testing determines that the subject suffers from a yeast infection.

In embodiments, the methods comprise detecting a disease, wherein the disease detected is caused by a disease-causing agent selected from the group of disease-causing organisms consisting of a virus, a bacterium, a mycoplasm, a fungus, a yeast, and other micro-organisms, and further comprising providing a prescription for the suitable treatment of said virus, bacterium, mycoplasm, fungus, yeast, or other micro-organism.

In embodiments, the methods are point-of service methods performed at a point-of-service location. In embodiments, the methods comprise performing a plurality of assays on a single small-volume clinical sample, or on aliquots thereof, and may be performed in less than about 40 minutes. In embodiments, the infection is caused by a disease selected from influenza, a respiratory disease, a sexually transmitted disease, and another infectious disease. In embodiments where the infection comprises influenza, the influenza may be selected from H1N1 (seasonal), H1N1 (novel), H3N2, H7N9, and H5N1. In embodiments where the infection comprises a respiratory disease, the infection may be selected from an upper respiratory disease and a lower respiratory disease. In embodiments, the respiratory disease is selected from the group consisting of adenovirus B, adenovirus C, adenovirus E, *Bordetella pertussis, mycobacterium tuberculosis* (MTB), *Staphylococcus aureus*, Methicillin-Resistant *Staphylococcus aureus* (MRSA), Group A *streptococcus*, Group B *streptococcus, Moraxella catarrhalis, Enterobacter aerogenes, Haemophilus parainfluenzae*, Metapneumo Virus, *Streptococcus pneumonia*, Parainfluenza Virus 1, Parainfluenza Virus 2, Parainfluenza Virus 3, Coronavirus OC43, Coronavirus NL63, Coronavirus MERS, Coronavirus HKU1, Coronavirus 229E, *Klibsiella* pneumonia phoE, *Klebsiella* pneumonia KPC, Bocavirus type 2,4, and Bocavirus type 1,3.

In embodiments, the infection comprises a sexually transmitted disease selected from a disease caused by herpes simplex virus (HSV), human immunodeficiency virus (HIV), HIV-2 Group A, HIV-2 Group B, HIV-1 Group M, Hepatitis B, Hepatitis Delta, herpes simplex virus (HSV), *streptococcus* B, and *treponema pallidum*. In embodiments, the infection comprises a disease caused by an infectious disease-causing agent selected from the group consisting of Influenza A Matrix protein, Influenza H3N2, Influenza H1N1 seasonal, Influenza H1N1 novel, Influenza B, *Streptococcus pyogenes* (A), *Mycobacterium Tuberculosis, Staphylococcus aureus* (MR), *Staphylococcus aureus* (RS), *Bordetella pertussis* (whooping cough), *Streptococcus agalactiae* (B), Influenza H5N1, Influenza H7N9, Adenovirus B, Adenovirus C, Adenovirus E, Hepatitis b, Hepatitis c, Hepatitis delta, *Treponema pallidum*, HSV-1, HSV-2, HIV-1, HIV-2, Dengue 1, Dengue 2, Dengue 3, Dengue 4, Malaria, West Nile Virus, *Trypanosoma cruzi* (Chagas), *Klebsiella pneumoniae* (Enterobacteriaceae spp), *Klebsiella pneumoniae* carbapenemase (KPC), Epstein Barr Virus (mono), Rhinovirus, Parainfluenza virus (1), Parainfluenza virus (2), Parainfluenza virus (3), Parainfluenza virus (4a), Parainfluenza virus (4b), Respiratory syncytial virus (RSV) A, Respiratory syncytial virus (RSV) B, Coronavirus 229E, Coronavirus HKU1, Coronavirus OC43, Coronavirus NL63, Novel Coronavirus, Bocavirus, human metapneumovirus (HMPV), *Streptococcus pneumoniae* (penic R), *Streptococcus pneumoniae* (S), *Mycoplasma pneumoniae, Chlamydia pneumoniae, Bordetella parpertussis, Haemophilus influenzae* (ampic R), *Haemophilus influenzae* (ampic S), *Moraxella catarrhalis, Pseudomonas* spp (*aeruginosa*), *Haemophilus parainfluenzae,* Enterobacter cloacae (Enterobacteriaceae spp), *Enterobacter aerogenes* (Enterobacteriaceae spp), *Serratia marcescens* (Enterobacteriaceae spp), *Acinetobacter baumanii, Legionella* spp, *Escherichia coli, Candida, Chlamydia trachomatis*, Human Papilloma Virus, *Neisseria gonorrhoeae, plasmodium*, and *Trichomonas* (vagin).

In embodiments, the infection comprises a bacterial infection caused by bacteria selected from the group consisting of *Bordetella pertussis, mycobacterium tuberculosis* (MTB), *Staphylococcus aureus*, Methicillin-Resistant *Staphylococcus aureus* (MRSA), Group A *streptococcus*, Group B *streptococcus, Moraxella catarrhalis, Enterobacter aerogenes, Haemophilus parainfluenzae, Streptococcus pneumonia, Klibsiella* pneumonia phoE, *Klebsiella* pneumonia KPC, and *treponema pallidum*.

In embodiments, the infection comprises a viral infection caused by a virus selected from the group consisting of an influenza virus, herpes simplex virus (HSV), human immunodeficiency virus (HIV), HIV-2 Group A, HIV-2 Group B, HIV-1 Group M, Hepatitis B, Hepatitis Delta, herpes simplex virus (HSV), West Nile Virus, Epstein-Barr Virus, a Dengue Virus, adenovirus B, adenovirus C, adenovirus E, Metapneumo Virus, Parainfluenza Virus 1, Parainfluenza Virus 2, Parainfluenza Virus 3, Coronavirus OC43, Coronavirus NL63, Coronavirus MERS, Coronavirus HKU1, Coronavirus 229E, Bocavirus type 2,4, and Bocavirus type 1,3. In embodiments of influenza infections, the influenza may be selected from H1N1 (seasonal), H1N1 (novel), H3N2, H7N9, and H5N1 influenza viruses. In embodiments, a viral infection comprises infection by a Dengue virus, wherein said Dengue virus is selected from Dengue virus type 1, Dengue virus type 2, Dengue virus type 3, and Dengue virus type 4.

A bill for the testing may be automatically generated at the POS. The amount of the bill may be calculated per the tests performed, or pursuant to the results of the testing. A bill for the testing may be automatically sent to the subject's insurance provider. Payment for the testing may be automatically obtained from the subject, or from the subject's insurance carrier, or from another source.

A prescription for treatment of a detected disorder may be provided at the POS location. A prescription for treatment of a detected disorder may be filled at the POS location. A bill for the filled prescription may be automatically generated. A bill for the prescription may be automatically sent to the subject's insurance provider. Payment for the filled prescription may be automatically obtained from the subject, or from the subject's insurance carrier, or from another source.

Accordingly, Applicants provide systems, methods, and devices for rapid analysis of a small-volume clinical sample in a short period of time. Such rapid analysis includes testing for the presence of markers indicative of a plurality of disease-causing agents in a short period of time. In embodiments, such disease-causing agents include agents which cause upper respiratory disorders, and include agents which cause lower respiratory disorders. In embodiments, such systems, methods, and devices are configured to detect one or more indicators of inflammation. In embodiments, such systems, methods, and devices are configured to detect one or more cytokines. In embodiments, such systems, methods, and devices are configured to detect one or more inflammatory cytokines. In embodiments, such systems, methods, and devices are configured to detect one or more anti-inflammatory cytokines.

In embodiments, Applicants provide systems, methods, and devices for detecting a plurality of disease-causing agents in a single clinical sample, or in a plurality of aliquots of a single clinical sample. In embodiments, a single clinical sample may be a small volume clinical sample of blood, sputum, tears, nasal swabs, throat swabs, mouth swabs (e.g., cheek swabs), vaginal swabs, or other bodily fluid, tissue, secretion, or excretion taken from a subject. In embodiments, a single clinical sample has a volume of less than about 500 µL, or less than about 250 µL, or less than 150 µL, or less than about 100 µL, or less than about 50 µL, or less than about 25 µL, or less than about 10 µL, or less than about 5 µL, or less than about 1 µL, or less.

In embodiments, clinical samples may be obtained at a point-of-service (POS) location. A POS location may be, for example, a retail pharmacy, a supermarket, a hospital, a clinic, a physician's office, or other location. Clinical samples may be tested at the POS location for multiple markers indicative of agents which may cause one or more of a plurality of diseases (e.g., at least 8, or at least 10, or at least 12, or at least 20, or at least 30, or at least 40, or at least 50, or at least 60, or more markers, indicative of the same or similar numbers of different diseases). The testing may be completed in a short period of time. In embodiments, the short period of time may be measured from the time the sample is inserted into a device or system for performing an analysis. In embodiments, the short period of time may be measured from the time the sample is obtained from the subject.

In embodiments, clinical samples may be analyzed at a POS location. In embodiments, clinical samples obtained at a POS location may be analyzed at the same POS location. In embodiments, clinical samples may be obtained at a point-of-service (POS) location and may be analyzed at a different location. In embodiments, clinical samples may be analyzed in a short period of time, e.g., in a period of time that is less than about 5 hours, or less than about 4 hours, or less than about 3 hours, or less than about 2 hours, or less than about 1 hour, or less than about half an hour.

In embodiments, Applicants provide devices (e.g., cartridges) for use in performing assays for detecting a plurality of disease-causing agents in a single clinical sample, or in a plurality of aliquots of a single clinical sample. In embodiments, such a device may comprise a plurality of vessels containing reagents for use in an assay for the detection of a plurality of markers indicative of an infectious agent, e.g., an upper respiratory infectious agent; a lower respiratory infectious agent; a sexually transmitted disease-causing agent; an agent detectable from a sample obtained from a swab (e.g., a throat swab, a nasal swab, or other swab); an agent detectable from a blood sample; or combinations thereof. In embodiments, a device may be a cartridge configured to contain a plurality of reagent vessels. In embodiments, a device may be a cartridge configured to contain a reagent vessel containing a reagent for detecting a marker indicative of a disease-causing agent. In embodiments, a device may be a cartridge configured to contain a plurality of reagent vessels containing reagents for detecting a marker indicative of a disease-causing agent. In embodiments, such a disease-causing agent, or such a plurality of disease-causing agents, includes disease-causing agents which cause upper respiratory disorders. In embodiments, such a disease-causing agent, or such a plurality of disease-causing agents, includes disease-causing agents which cause lower respiratory disorders. In embodiments, such a disease-causing agent, or such a plurality of disease-causing agents, includes disease-causing agents which cause sexually transmitted diseases. In embodiments, such a disease-causing agent, or such a plurality of disease-causing agents, includes disease-causing agents which may be detected in a blood sample. In embodiments, such a disease-causing agent, or such a plurality of disease-causing agents, includes disease-causing agents which may be detected in a sample obtained with a swab, such as a throat swab, or a nasal swab, or a cheek swab, or other sample, or combinations thereof.

In embodiments, devices for use in performing assays for detecting a plurality of disease-causing agents as disclosed herein may further include a space, or a vessel, for holding a swab; or may further include a space, or a vessel, for holding two swabs, or a plurality of swabs. In embodiments, such devices may further include two spaces, or two vessels, for holding two swabs; or may include a plurality of spaces, or of vessels, for holding a plurality of swabs. In embodiments, a single swab may be placed in a single space, or vessel; in embodiments, two swabs may be placed in a single space, or vessel; and in embodiments, a plurality of swabs may be placed in a single space, or vessel. Thus, in embodiments, a swab may be placed in a vessel, and, in embodiments, a swab, or a plurality of swabs, may be placed in a single vessel. In embodiments, a plurality of swabs may be placed in a plurality of vessels. Such a vessel for holding a swab, or such vessels for holding swabs, may contain a reagent, or a diluent, or other solution for use with a swab or swabs. In embodiments, a vessel for holding a swab may be used to provide a clean swab for use in obtaining a sample. In embodiments, a vessel for holding a swab may be used to i) provide a clean swab for use in obtaining a sample and also to ii) receive the swab after its use in obtaining a sample from a subject. In embodiments, a vessel for holding a plurality of swabs may be used to provide a plurality of clean swabs for use in obtaining a sample. In embodiments, a vessel for holding a plurality of swabs may be used to i) provide a plurality of clean swabs for use in obtaining a sample and also to ii) receive one or more of the plurality of swabs after its use in obtaining a sample from a subject.

For example, a throat swab and a nasal swab may be obtained from a subject. A nasal swab may be useful for testing for upper respiratory diseases, and a throat swab may be useful for testing lower respiratory diseases. In embodiments, the throat swab may be placed in one vessel in a device (e.g., a cartridge), and the nasal swab may be placed in a different vessel in the device. These vessels may contain a reagent, or a diluent, or other solution for use with the swabs; such reagents may be different for the throat swab and the nasal swab. In embodiments, the throat swab and the nasal may be placed in the same vessel in a device. The vessel may contain a reagent, or a diluent, or other solution for use with these swabs. The device may be placed in an analysis device, or within an analysis system, for analysis. Such analysis devices and analysis systems may be placed at the same location as that where the sample was obtained; or such analysis devices and analysis systems may be at a different location or locations than the location where the sample was obtained.

In embodiments, a device may be or comprise a cartridge configured to contain a reaction vessel or a plurality of reagent vessels. In embodiments, a device may be or comprise a cartridge configured to contain a reaction vessel or a plurality of reaction vessels. In embodiments, a device may be a cartridge configured to contain a cytometry cuvette, or a plurality of cytometry cuvettes. In embodiments, a device may be or comprise a cartridge configured to contain a waste container, or a plurality of waste containers. In embodiments, a device may be or comprise a cartridge configured to contain a sample; in embodiments, a sample may be contained in a sample collection device. In embodiments, a device may be or comprise a cartridge configured to contain a sample collection vessel.

In embodiments, a device may be or comprise a cartridge configured to contain a reagent vessel, or a plurality of reagent vessels, and a reaction vessel or a plurality of reaction vessels. In embodiments, such a device may include reagents for use in nucleic acid assays; for immunoassays (e.g., ELISA assays); general chemistry assays (e.g., for clinical electrolytes, vitamin levels, blood component levels, and other targets); cytometric assays; and for combinations thereof. In embodiments, such a device may include reagents and reaction vessels for use in nucleic acid assays; for immunoassays (e.g., ELISA assays); general chemistry assays (e.g., for clinical electrolytes, vitamin levels, blood component levels, and other targets); cytometric assays; and for combinations thereof. In embodiments, such a device may include reagents, reaction vessels, and tools, cuvettes, and other implements for use in nucleic acid assays; for immunoassays (e.g., ELISA assays); general chemistry assays (e.g., for clinical electrolytes, vitamin levels, blood component levels, and other targets); cytometric assays; and for combinations thereof.

Accordingly, Applicants disclose systems for detecting the presence of one or more of a plurality of markers indicative of an infectious disease in a small-volume clinical sample, comprising:
a) a sample handling system;
b) a detection station comprising an optical sensor;
c) a fluidically isolated sample collection unit configured to retain a clinical sample;
d) an assay station comprising at least a first and a second fluidically isolated assay unit, wherein the first unit comprises a first reagent and the second unit comprises a second reagent; and
e) a controller, wherein the controller comprises a local memory and is operatively coupled to the sample handling system and the detection station;
wherein the system is configured to perform assays with one or both of the first and second assay units; wherein the local memory of the controller comprises a protocol comprising instructions for: i) directing the sample handling system to transfer a portion of the clinical sample to the first assay unit and to the second assay unit; and ii) directing the sample handling system to transfer the first assay unit and the second unit assay unit to the detection station.

Accordingly, Applicants disclose systems for detecting the presence of one or more of a plurality of markers indicative of an infectious disease in a small-volume clinical sample, comprising:
a) a sample handling system;
b) a detection station comprising an optical sensor;
c) a fluidically isolated sample collection unit configured to retain a clinical sample;
d) an assay station comprising at least a first, second, and third fluidically isolated assay unit, wherein the first unit comprises a first reagent, the second unit comprises a second reagent, and the third unit comprises a third reagent; and
e) a controller, wherein the controller comprises a local memory and is operatively coupled to the sample handling system and the detection station;
wherein the system is configured to perform assays with any one or more of the first, second, and third assay units; wherein the local memory of the controller comprises a protocol comprising instructions for: i) directing the sample handling system to transfer a portion of the clinical sample to the first assay unit, the second assay unit and the third assay unit; and ii) directing the sample handling system to transfer the first assay unit, the second assay unit, and the third assay unit to the detection station. In embodiments, the system may include only two assay units; or may include four assay units; or may include more than four assay units.

In embodiments, the system is a point-of service system. In embodiments, the system is contained within a housing. In embodiments, the system is located at a point-of-service location, and is configured for use in analyzing a sample at said point-of-service location. In embodiments, the system is a point-of service system configured to perform a plurality of assays on a single small volume sample, or on aliquots thereof.

Applicants further disclose systems for detecting the presence of one or more of a plurality of markers indicative of an infectious disease in a small-volume clinical sample, comprising:
a) a sample handling system;
b) a detection station comprising an optical sensor;

c) a fluid handling system configured to transport fluids between components of said system, wherein said transport of fluids comprises transport of isolated aliquots of fluid;
d) a fluidically isolated sample collection unit configured to retain a clinical sample;
e) an assay station comprising at least a first, second, and third fluidically isolated assay unit, wherein the first unit comprises a first reagent, the second unit comprises a second reagent, and the third unit comprises a third reagent; and
f) a controller, wherein the controller comprises a local memory and is operatively coupled to the sample handling system and the detection station;

wherein the system is configured to perform assays with any one or more of the first, second, and third assay units; wherein the local memory of the controller comprises a protocol comprising instructions for: i) directing the sample handling system to transfer a portion of the clinical sample to the first assay unit, the second assay unit and the third assay unit; and ii) directing the sample handling system to transfer the first assay unit, the second assay unit, and the third assay unit to the detection station.

In embodiments, the system is a point-of service system. In embodiments, the system is contained within a housing. In embodiments, the fluid handling system is configured to transport fluid within said housing. In embodiments, the system is located at a point-of-service location, and is configured for use in analyzing a sample at said point-of-service location. In embodiments, the system is a point-of service system configured to perform a plurality of assays on a single small volume sample, or on aliquots thereof.

In embodiments, Applicants disclose a clinical sample processing system, comprising:
a) a sample handling system;
b) a detection station comprising an optical sensor;
c) a fluidically isolated sample collection unit configured to retain a clinical sample;
d) an assay station comprising at least a first, second, and third fluidically isolated assay unit, wherein the first unit comprises an antibody, the second unit comprises an oligonucleotide, and the third unit comprises a chromogen or a dye or other label; and
e) a controller, wherein the controller is operatively coupled to the sample handling system, wherein the sample handling system is configured to transfer a portion of the clinical sample from the sample collection unit to each of the first assay unit, the second assay unit, and the third assay unit, and the device is configured to perform an immunoassay, a nucleic acid assay, and a general chemistry assay comprising a chromogen. In embodiments, the system is a point-of service system. In embodiments, the system is contained within a housing. In embodiments, the system is located at a point-of-service location, and is configured for use in analyzing a sample at said point-of-service location. In embodiments, the system is a point-of service system configured to perform a plurality of assays on a single small volume sample, or on aliquots thereof.

In embodiments, Applicants disclose methods of performing at least 4 different assays selected from immunoassays, nucleic acid assays, cytometric assays, and general chemistry assays on a small-volume clinical sample, comprising:
a) introducing a clinical sample having a volume of no greater than 500 microliters into a sample processing device, wherein the device comprises:
i) a sample handling system;
ii) a detection station;
iii) a cytometry station comprising an imaging device and a stage for receiving a microscopy cuvette; and
iv) an assay station comprising at least a first, a second, a third, and a fourth independently movable assay unit;
b) with the aid of the sample handling system, transferring a portion of the clinical sample to each of the first, second, third, and fourth assay units, wherein a different assay is performed in each of the first, second, third, and fourth assay units;
c) with the aid of the sample handling system, transferring the first, second, third, and fourth assay units to the detection station or cytometry station, wherein assay units comprising immunoassays or general chemistry assays are transferred to the detection station and assay units comprising cytometric assays are transferred to the cytometry station;
d) with the aid of the detection station or cytometry station, obtaining data measurements of the assay performed in each of the first, second, third, and fourth assay units.

In embodiments, the methods are point-of service methods. In embodiments, the system used in performing the methods is contained within a housing. In embodiments, the methods are performed at a point-of-service location, and may be used in analyzing a sample at said point-of-service location. In embodiments, the methods comprise point-of service methods for performing a plurality of assays on a single small volume sample, or on aliquots thereof.

In embodiments, the methods include methods of determining the type of infection suffered by a subject. Methods of determining the type of infection as disclosed herein include, without limitation, methods as disclosed herein comprising determining whether a subject suffers from a bacterial, viral, yeast, fungus, and other infection. For example, methods of determining the type of infection as disclosed herein include methods of determining whether a subject suffers from a bacterial infection or from a viral infection. In embodiments, the methods include methods of detecting, identifying, quantifying, and combinations thereof, markers in a sample indicative of the type of infection suffered by a subject. Methods of detecting, identifying, quantifying, and combinations thereof, markers in a sample indicative of the type of infection as disclosed herein include, without limitation, methods as disclosed herein comprising detecting, identifying, quantifying, and combinations thereof, markers in a sample indicative of a bacterial, viral, yeast, fungus, and other infection. For example, methods as disclosed herein include methods of detecting, identifying, quantifying, and combinations thereof, markers in a sample indicative of a bacterial infection or a viral infection.

Methods disclosed herein may be used to determine whether a subject suffers from, e.g., a bacterial, viral, yeast, fungus, and other infection. Determination of the type of infection as disclosed herein may be used to guide therapy of the subject suffering from the infection. Determination of the type of infection as disclosed herein may be used to guide selection of pharmaceuticals for treatment of the subject suffering from the infection. Determination of the type of infection as disclosed herein may be used to guide selection of the dosage, or the dosing regimen, of pharmaceuticals used for the treatment of the subject suffering from the infection. For example, methods disclosed herein may be used to determine whether a subject suffers from a bacterial infection or a viral infection. Determination of whether a subject suffers from a bacterial infection or a viral infection as disclosed herein may be used to guide therapy of the subject suffering from the infection. Determination of whether a subject suffers from a bacterial infection or a viral infection as disclosed herein may be used to guide selection of pharmaceuticals for treatment of the subject suffering from the infection. Determination of whether a subject suffers from a bacterial infection or a viral infection as disclosed herein may be used to guide the selection of a pharmaceutical, selection of the dosage, the dosing regimen, or a combination thereof, used in the treatment of the subject suffering from the infection. For example, where an infection is determined to be a bacterial infection, antibiotics may be prescribed; however, where an infection is determined to be a viral infection, antibiotics are not indicated, and, in embodiments, will not be prescribed. Determination that a subject suffers from a viral infection may enable the subject to avoid unnecessary treatment and expense (e.g., where antibiotic therapy is avoided when the infection is identified as being a viral infection). Determination that a subject suffers from a viral infection may enable the subject to obtain more appropriate therapy directed to viral infections, as opposed to antibiotic therapy that is directed to bacterial infections.

Similarly, determination of whether a subject suffers from a yeast, fungus, and other infection, as opposed to a bacterial or viral infection, may guide or determine the therapy provided to a subject suffering from an infectious disease, including guiding or determining the selection of a pharmaceutical, the selection of the dosage, the dosing regimen, or a combination thereof, used in the treatment of the subject suffering from the infection. Determination of the type of infection may enable the subject to obtain more appropriate therapy directed to the particular type of infection suffered by the subject, as opposed to inappropriate, or less specific, therapy that may not be as effective for that type of infection.

Accordingly, Applicants disclose herein methods for providing a prescription for treatment of an infectious disease in a subject, comprising: providing a clinical sample obtained from a subject; analyzing said clinical sample, wherein analyzing comprises testing for, or detecting the presence of, a plurality of disease markers, in the clinical sample; determining a suitable treatment for a disease indicated by the presence of a marker detected by said analysis; and providing a prescription for said suitable treatment. Applicants further disclose herein methods for providing a prescription for treatment of an infectious disease in a subject, comprising: providing a clinical sample obtained from a subject; analyzing said clinical sample at a point-of-service (POS) location, wherein analyzing comprises testing for, or detecting the presence of, a plurality of disease markers, in the clinical sample; determining a suitable treatment for a disease indicated by the presence of a marker detected by said analysis; and providing a prescription for said suitable treatment.

In embodiments of methods for providing a prescription for treatment of an infectious disease in a subject, the analysis of the sample comprises analysis to determine whether the subject suffers from a bacterial infection, a viral infection, a yeast infection, a fungal infection, other infection, or combination thereof. In embodiments of methods for providing a prescription for treatment of an infectious disease in a subject, the analysis of the sample comprises analysis to determine whether the subject suffers from a bacterial infection or a viral infection. In embodiments of methods for providing a prescription for treatment of an infectious disease in a subject, where the analysis of the sample determines that the subject suffers from a bacterial infection, providing a prescription for said suitable treatment comprises prescription of an antibiotic. In embodiments of methods for providing a prescription for treatment of an infectious disease in a subject, where the analysis of the sample determines that the subject suffers from a viral infection, providing a prescription for said suitable treatment comprises avoiding the prescription of an antibiotic, and may include the prescription of an anti-viral drug. In embodiments of methods for providing a prescription for treatment of an infectious disease in a subject, where the analysis of the sample determines that the subject suffers from a fungal infection, providing a prescription for said suitable treatment comprises the prescription of an anti-fungal drug. In embodiments of methods for providing a prescription for treatment of an infectious disease in a subject, where the analysis of the sample determines that the subject suffers from a bacterial infection that is a *mycoplasma* infection, providing a prescription for said suitable treatment comprises the prescription of an anti-mycoplasmal drug. In embodiments of methods for providing a prescription for treatment of an infectious disease in a subject, where the analysis of the sample determines that the subject suffers from a yeast infection, providing a prescription for said suitable treatment comprises the prescription of an anti-yeast drug.

Accordingly, the systems, devices, and methods disclosed herein are point-of service methods. In embodiments, the systems disclosed herein, including the systems used in performing the methods disclosed herein, may be contained and the methods performed within a housing. In embodiments, the devices disclosed herein may be placed or used within a housing, e.g., a housing containing a system disclosed herein. In embodiments, the systems disclosed herein may be located at a POS location, and the methods may be performed at a point-of-service location. The systems and methods disclosed herein may be used in analyzing a sample at said point-of-service location. In embodiments, the systems and methods comprise point-of service methods for performing a plurality of assays on a single small volume sample, or on aliquots thereof.

In embodiments, Applicants disclose systems, methods, and devices for detecting one or more of a plurality of markers indicative of a disease in a clinical sample obtained at a point-of-service (POS) location. In embodiments, such a clinical sample is a small volume clinical sample. In embodiments, the one or more markers are detected in a short period of time. In embodiments, the sample is obtained at a POS location. In embodiments, the systems and devices are located at a POS location. In embodiments, the detection of the one or more markers is performed at a POS location. In embodiments, the diseases are infectious diseases. In embodiments, the diseases are caused by a disease-causing agent selected from the group of disease-causing organisms consisting of a virus, a bacterium (including a *mycoplasma*), a fungus, a yeast, and other micro-organisms. In embodiments, the diseases are infectious respiratory diseases, and may be upper respiratory diseases, and may be lower respiratory diseases.

Accordingly, in embodiments, Applicants disclose POS systems, methods, and devices. In embodiments, such POS systems, methods, and devices comprise automated POS systems, methods, and devices. In embodiments, for example, Applicants disclose an automated POS system, automated methods, and devices thereof, for detecting one or more of a plurality of markers indicative of a disorder in a clinical sample obtained at a POS location; such a disorder may be a respiratory disorder, and may be a disorder caused by a disease-causing agent selected from the group of disease-causing organisms consisting of a virus, a bacterium (including a *mycoplasma*), a fungus, a yeast, and other micro-organisms. In embodiments, such automated POS systems, automated methods, and devices thereof, are configured for use at POS locations, and for use with samples obtained at POS locations. In embodiments, such automated POS systems, automated methods, and devices thereof, are configured for use on a single small-volume clinical sample. In embodiments, such automated POS systems, automated methods, and devices thereof, are configured to detect, if present, one or more of a plurality of markers indicative of a disorder in a clinical sample in a short period of time.

In embodiments, such automated POS systems, methods, and devices are located at a POS location selected from a retail pharmacy, a supermarket, a clinic, a hospital, and a doctor's office. In embodiments, a prescription for a treatment is issued at said POS location. In embodiments, a prescription for a treatment is issued at said POS location pursuant to the results of such testing performed by an automated POS systems, methods, and devices located at the POS location. In embodiments, a prescription for a treatment is filled at said POS location, wherein the prescription was issued for a treatment is pursuant to the results of such testing performed by an automated POS systems, methods, and devices located at the POS location. In embodiments, a bill for testing is issued at the POS location; such a bill may be issued automatically. In embodiments, a bill for a prescription is issued at the POS location, wherein the prescription was issued for a treatment is pursuant to the results of such testing performed by an automated POS systems, methods, and devices located at the POS location; such a bill may be issued automatically. In embodiments, a bill for a test or a prescription may be issued from the POS location to a subject's insurance carrier; such a bill may be issued automatically. In embodiments, an automatic payment may be made for a test performed or a prescription filled at from the POS location to a subject's insurance carrier, pursuant to a bill issued automatically from the POS location.

Accordingly, Applicants disclose devices configured to measure or detect a disease-causing agent or marker indicative of a disease-causing agent in a sample according to a method disclosed herein. Such a sample may be a small-volume clinical sample. Such devices may be configured to measure or detect a particular disease-causing agent or marker indicative of a particular disease-causing agent in a sample in less than about three hours, or less than about two hours, or in less than about one hour, or, in embodiments, in less than about 40 minutes, or in less than about 30 minutes.

Devices disclosed herein may be configured to perform an assay for the detection or measurement of a plurality of disease-causing agents or markers indicative thereof. Devices disclosed herein may be configured to perform an assay for the detection or measurement of a particular disease-causing agent or marker indicative thereof and also to perform an assay comprising the measurement of a morphological characteristic of a cell in the sample. Devices disclosed herein may be configured to perform an assay for the measurement of a disease-causing agent or marker indicative thereof and also to perform an assay comprising the measurement of another analyte, e.g., a cytokine, a prostaglandin, histamine, a steroid (e.g., a glucocorticoid, or other steroid), a vitamin, a hormone, a drug or metabolite of a drug, or other analyte. Such devices may be configured wherein the assays, or the order of performance of assays, that are performed by said device may be altered by communication with another device.

Methods and compositions disclosed herein provide rapid assays which require only small amounts of sample, such as only small amounts of saliva, urine, blood, or fluid in which a throat swab, cheek swab, or nasal swab has been immersed. In embodiments, a plurality of samples, including a plurality of small samples, may comprise a plurality of sample types, such as saliva, urine, blood, or fluid samples, may be provided to, and analyzed by, systems, devices, and methods disclosed herein. Methods, devices and systems disclosed herein are configured to perform such rapid assays which require only small amounts of sample. Methods, devices and systems disclosed herein are configured to perform such rapid assays on a plurality of sample types, and may require only small amounts of each sample type. Methods, devices and systems disclosed herein are configured to perform multiple assays on a sample, or on a plurality of sample types, and may be used to screen for one or more of a plurality of diseases. Methods, devices and systems disclosed herein are configured to perform multiple assays on a sample, or on a plurality of sample types, and may be used to screen for diseases caused by one or more of viruses, bacteria, yeast, fungus, *mycoplasma*, archea, fungus, yeast, parasites, and other micro-organisms. Accordingly, the methods, devices, and systems disclosed herein provide rapid tests, which require only small clinical samples, and thus provide advantages over other methods, devices, and systems.

BRIEF DESCRIPTION OF THE DRAWINGS

FIG. 2B shows detection of influenza A (seasonal H1N1 strain) marker at times well before any significant amounts of amplification of non-target nucleic acid message occurred.

FIG. 3B shows detection of influenza A (novel H1N1 strain) marker at times well before any significant amounts of amplification of non-target nucleic acid message occurred.

FIG. 4B shows detection of influenza A (H3N2 strain) marker at times well before any significant amounts of amplification of non-target nucleic acid message occurred.

FIG. 5B shows detection of influenza A (H7N9 strain) marker at times well before any significant amounts of amplification of non-target nucleic acid message occurred.

FIG. 6B shows detection of influenza A (H5N1 strain) marker at times well before any significant amounts of amplification of non-target nucleic acid message occurred.

FIG. 7B shows detection of influenza B marker at times well before any significant amounts of amplification of non-target nucleic acid message occurred.

FIG. 8B shows detection of influenza Matrix Protein marker at times well before any significant amounts of amplification of non-target nucleic acid message occurred.

FIG. 22 shows various panels naming disorders which may be identified by the methods and devices discussed herein.

FIG. 24A shows various respiratory disease panels naming respiratory disease types which may be identified by the methods and devices discussed herein.

FIG. 25A shows various hospital acquired infectious disease panels naming respiratory disease types which may be identified by the methods and devices discussed herein.

FIG. 27 shows the specificity of the nucleic acid assays for the target H2N2 influenza type.

FIG. 29 lists potential interfering substances for the sexually transmitted disease (STD) panel that were found not to interfere with the nucleic acid assays.

FIG. 30 lists potential interfering substances for the sexually transmitted disease (STD) urine panel that were found not to interfere with the nucleic acid assays.

FIG. 31 lists potential interfering substances for the blood panel that were found not to interfere with the nucleic acid assays.

DETAILED DESCRIPTION

Figure 1A:
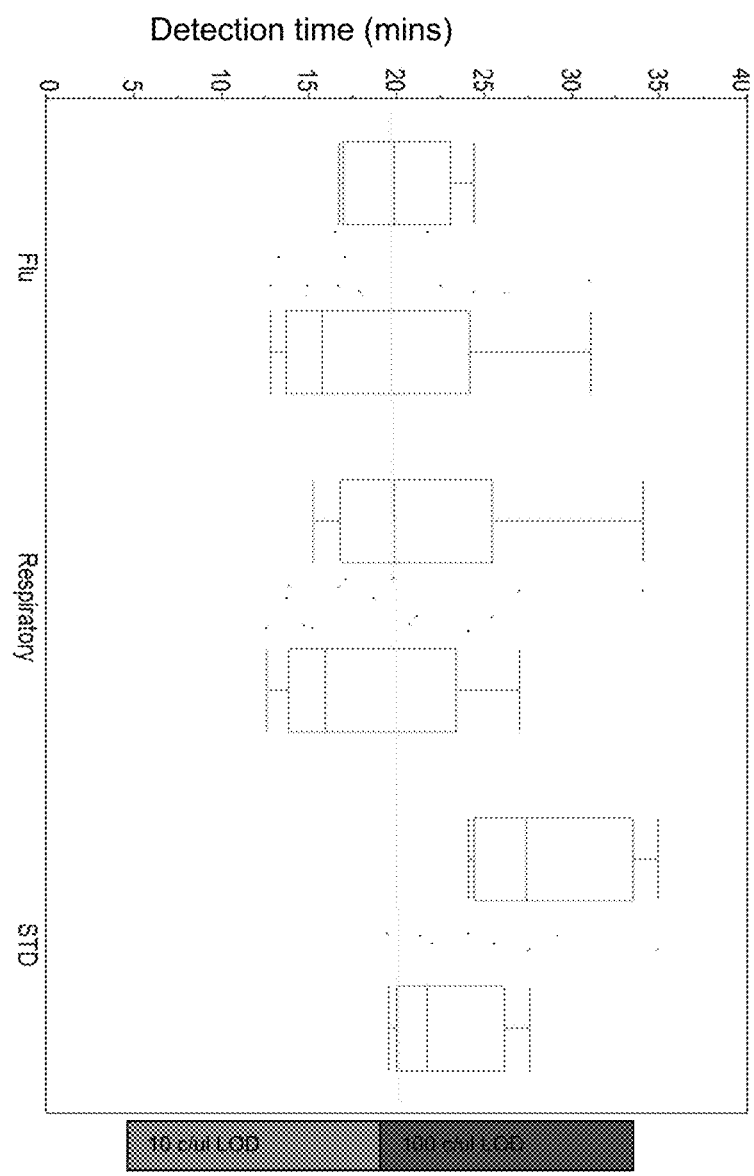
FIG. 1A provides a graphic summary of the durations of time from the initiation of nucleic acid assay until detection of the presence of a target nucleic acid in a sample for a range of markers and for two different concentration ranges of the markers (10 c/µl and 100 c/µl, where "c/µl" means copies per microliter (µL)). The times are labeled "LOD" ("length of delay"). The vertical axis is shown in units of relative fluorescence (relative fluorescence units, RFU), in thousands.

Description and disclosure of examples of reagents, assays, methods, kits, devices, and systems which may be used with the methods, assays, reagents, devices and systems disclosed herein may be found, for example, in U.S. Pat. Nos. 8,088,593; 8,380,541; U.S. patent application Ser. No. 13/769,798, filed Feb. 18, 2013; U.S. patent application Ser. No. 13/769,779, filed Feb. 18, 2013; U.S. patent application Ser. No. 13/769,820, filed Feb. 18, 2013; PCT/US2012/57155, filed Sep. 25, 2012; U.S. patent application Ser. No. 13/244,949, filed Sep. 26, 2011; U.S. Application Ser. No. 61/766,095, filed Feb. 18, 2013; U.S. Application Ser. No. 61/673,245, filed Sep. 26, 2011; U.S. Patent Application Ser. No. 61/874,976, filed Sep. 6, 2013; U.S. Patent Application Ser. No. 61/885,462, filed Oct. 1, 2013; U.S. Patent Application Ser. No. 62/001,039, filed May 20, 2014; U.S. Patent Application Ser. No. 62/001,053, filed May 21, 2014; U.S. Patent Application Ser. No. 62/010,382, filed Jun. 10, 2014; U.S. Patent Application Ser. No. 61/885,467, filed Oct. 1, 2013; U.S. Patent Application Ser. No. 61/879,664, filed Sep. 18, 2013; and U.S. Patent Application 61/805,923, filed Mar. 27, 2013, the disclosures of which patents and patent applications are all hereby incorporated by reference in their entireties.

Disclosure of methods of detecting nucleic acid targets include, for example, methods, assays, reagents, and devices as disclosed in U.S. Application Ser. No. 61/800,606, filed Mar. 15, 2013; U.S. Application Ser. No. 61/908,027, filed Nov. 22, 2013; U.S. Application Ser. No. 62/001,050, filed May 20, 2014; U.S. application Ser. No. 14/214,850, filed Mar. 15, 2014; PCT/US2014/030034, filed Mar. 15, 2014; U.S. Application Ser. No. 61/800,241, filed Mar. 15, 2013; and U.S. Application Ser. No. 61/800,340, filed Mar. 15, 2013; the disclosures of which patent applications are hereby incorporated by reference in their entireties. Further methods for the detection of nucleic acid targets include, for example, Polymerase Chain Reaction (PCR) methods described, for example, in U.S. Pat. No. 4,683,195; and generally in Mullis et al., Cold Spring Harbor Symp. Quant. Biol. 51:263 (1987); Erlich, ed., PCR Technology (Stockton Press, N.Y., 1989).

Disclosure of methods for detecting protein targets, including antibody methods, may be found, for example, in U.S. Pat. Nos. 4,376,110; 4,816,567; 7,429,652; European Patent EP 404,097; and International Patent Application Publication WO 93/11161, the disclosures of which are hereby incorporated by reference in their entireties. Further methods for the detection of protein targets (generically termed "immunoassays" herein) include, for example, direct or competitive binding assays using techniques such as western blots, radioimmunoassays, ELISA (enzyme linked immunosorbent assay), "sandwich" immunoassays, immunoprecipitation assays, fluorescent immunoassays, and protein A immunoassays.

Disclosure regarding systems, devices, and methods for analyzing clinical samples, including clinical samples such as small-volume clinical samples, and including systems, devices, and methods for analyzing small-volume clinical samples in short periods of time, may be found, for example, in U.S. Pat. Nos. 8,380,541; 8,088,593; 8,380,541; U.S. patent application Ser. No. 13/769,798, filed Feb. 18, 2013; U.S. patent application Ser. No. 13/769,820, filed Feb. 18, 2013; U.S. patent application Ser. No. 13/769,779, filed Feb. 18, 2013; PCT/US2012/57155, filed Sep. 25, 2012; U.S. Patent Application 61/805,923, filed Mar. 27, 2013; and incorporated by reference herein (supra).

Before the present novel target-binding molecules, compositions, assays, methods, and kits are disclosed and described, it is to be understood that the terminology used herein is for the purpose of describing particular embodiments only and is not intended to be limiting. It is also to be understood that the present disclosure provides explanatory and exemplary descriptions and examples, so that, unless otherwise indicated, the molecules, compositions, assays, methods, and kits disclosed herein are not limited to the specific embodiments described herein.

It must be noted that, as used in the specification and the appended claims, the singular forms "a," "an" and "the" include plural referents unless the context clearly dictates otherwise. Thus, for example, reference to "a salt" refers to a single salt or mixtures of different salts, and the like.

In this specification and in the claims that follow, reference will be made to a number of terms, which shall be defined to have the following meanings:

Acronyms and abbreviations, such as "rpm" (revolutions per minute), "min" (minute), "sec" (second), and so forth, have their customary meanings.

As used herein, the terms "normal" and "normal level" refer to the levels of a marker as found in a healthy population of normal subjects. For example, the normal level for a particular type of white blood cell found is the level of that type of white blood cell found in blood samples from a healthy population of normal subjects.

As used herein, the terms "high" and "high level" and the like refer to levels that significantly exceed normal levels, that is, a high level of a marker is one that significantly exceeds the levels of that marker that is found in a healthy population of normal subjects.

As used herein, the terms "low" and "low level" and the like refer to levels that are below normal levels, that is, a low level of a marker is one that is below the levels of that marker that is found in a healthy population of normal subjects.

It will be understood that, where a marker is typically absent, or scarce, in normal subjects, a normal level of a marker may be very low in absolute numbers (e.g., as measured by numbers of markers per unit volume, or weight of marker per unit volume), and still be the normal level for that marker. Thus, for example, where the marker is an antibody to a particular infectious disease, and most healthy normal subjects have not been recently exposed to that particular disease, the normal levels of antibodies to that disease may be low in absolute terms, and levels in a subject that exceed the normal level would indicate that the subject has recently been exposed to, or is suffering an infection by, that disease.

The term "isolated" as used herein when used to describe the various nucleic acids and proteins disclosed herein, means the nucleic acid or protein (or other molecule) has been separated and/or recovered from at least one contaminant with which it is ordinarily associated. Ordinarily, however, isolated nucleic acids and proteins will be prepared by at least one purification step.

The term "moiety" as used herein refers to any particular composition of matter, e.g., a molecular fragment, an intact molecule, or a mixture of materials.

As used herein, the terms "disease-causing agent", "disease-causing organism" and plurals and grammatical equivalents are used interchangeably to refer to viruses, bacteria, yeast, and other micro-organisms which may cause disease in a subject. Thus, when referring to diseases and their causes, the terms "agent", "organism" and plurals and grammatical equivalents are used interchangeably herein.

As used herein, the term "virus" refers to organisms which include nucleic acid message (either RNA or DNA) which allows their replication in infected host cells. The term virus includes both DNA viruses or RNA viruses. Viruses may cause diseases.

As used herein, the term "micro-organism" refers to small unicellular or multicellular organisms which may infect cells, organs, tissues, or surfaces of plants or animals, including humans. The term microorganism includes bacteria (including *mycoplasma*), archea, fungus, yeast, parasites, and other small organisms. Micro-organisms may cause diseases.

As used herein, the term "bacteria" refers to small unicellular, prokaryotic organisms which may infect cells, organs, tissues, or surfaces of plants or animals, including humans. The term bacteria includes Gram negative bacteria and Gram positive bacteria. Bacteria may cause diseases. *Mycoplasma* are a form of bacteria that lack cell walls.

As used herein, the term "drug" is used broadly to refer to any agent which may be administered to a subject for the purpose of treating a disease or condition suffered by the subject; such treating may include prevention, amelioration of symptoms, hastening recovery, strengthening the patient in the face of a disease or condition, as well as directly combatting the disease or condition. Where the disease or condition results from an infection, e.g., is due to an infectious disease, the drug may be, without limitation, an antibiotic, an anti-viral drug, an anti-fungal drug, an anti-mycoplasmal drug, an anti-yeast drug, or combinations thereof.

As used herein, the term "antibiotic" is used broadly to refer to drugs which act to reduce or eliminate bacterial infections. Antibiotics include, without limitation, penicillin, ampicillin, amoxicillin, tetracycline, oxytetracycline, doxycycline, minocycline, a sulfonamide sulfa-drug (such as, e.g., sulfanilamide, sulfamethoxazole, sulfadiazine), erythromycin, ciprofloxacin, gentamycin, oligomycin, azithromycin, clarithromycin, a cephalosporin, e.g., cefaclor, cefprozil, cefuroxime axetil, loracarbef, cefdinir, cefixime, cefpodoxime proxetil, ceftibuten, or ceftriaxone, gramicidin, valinomycin, nonactin, alamethicin, and other antibiotics.

As used herein, the term "anti-*mycoplasma*" is used broadly to refer to drugs which act to reduce or eliminate bacterial infections where the bacteria are *mycoplasma*. Antibiotics that target the cell wall are typically ineffective against *mycoplasma*, which lack cell walls. Antibiotics such as, e.g., plasmocin, doxocycline, minocycline, gramicidin, valinomycin, nonactin, alamethicin, macrolide antibiotics, and others may be used to treat mycoplasmal infections.

As used herein, the term "anti-viral" is used broadly to refer to drugs which act to reduce or eliminate viral infections. Ant-viral drugs include, for example, zanamivir, oseltamivir, acyclovir, adefovir, darunivir, famciclovir, ganciclovir, nexavir, rifampicin, pieconaril, amantadine, rimantadine, and others.

As used herein, the term "anti-fungal" is used broadly to refer to drugs which act to reduce or eliminate fungus infections. Ant-fungal drugs include, for example, amphotericin, nystatin, candicin, filipin, hamycin, netamycin, rimocydin, bifonazole, clotrimazole, other imidazole, triazole, and thiazoles, and others. Some drugs which may be used to treat fungal infections may also be suitable for treating yeast infections.

As used herein, the term "anti-yeast" is used broadly to refer to drugs which act to reduce or eliminate yeast infections. Anti-yeast drugs include, for example, antimycotics such as, e.g., clotrimazole, nystatin, fluconazole, ketoconazole, amphotericin, gentian violet, and other drugs. Some drugs which may be used to treat yeast infections may also be suitable for treating fungal infections.

As used herein, the phrase "nucleic acid markers indicative of" a particular infection refers to nucleic acid molecules (including single-stranded and double-stranded DNA and RNA molecules) and fragments thereof, which are derived from disease-causing organisms, or are copies of, or are substantially similar to, or are complementary to, nucleic acid molecules derived from the organism which causes that particular infectious disease. Detection of nucleic acid markers indicative of a particular infection in a sample indicates that the disease-causing organism is, or was, present in the sample and thus that the subject has been exposed to the disease-causing organism, and likely suffers or suffered from the particular infection caused by that particular disease-causing organism.

As used herein, the phrase "antibody markers indicative of" a particular infection refers to antibodies (or portions or fragments thereof) which are directed to an antigen or antigens found on the organisms that cause that particular infectious disease. Detection of antibody markers indicative of a particular infection in a sample indicates that the disease-causing organism is, or was, present in the sample and thus that the subject has been exposed to the disease-causing organism, and likely suffers or suffered from the particular infection caused by that particular disease-causing organism.

As used herein, a nucleic acid comprises a molecule made up of nucleotides, and refers to deoxyribonucleic acid (DNA) and to ribonucleic acid (RNA) molecules.

As used herein, "nucleic acid" includes both DNA and RNA, including DNA and RNA containing non-standard nucleotides. A "nucleic acid" contains at least one polynucleotide (a "nucleic acid strand"). A "nucleic acid" may be single-stranded or double-stranded. The term "nucleic acid" refers to nucleotides and nucleosides which make up, for example, deoxyribonucleic acid (DNA) macromolecules and ribonucleic acid (RNA) macromolecules. Nucleic acids may be identified by the base attached to the sugar (e.g., deoxyribose or ribose); as used herein, the following abbreviations for these bases are used to represent nucleic acids in sequence listings identifying and describing their structures (either upper-case or lower-case may be used).

TABLE 1A

| Base (in Nucleic Acid) | Letter Code |
|---|---|
| Adenine | A |
| Thymine | T |
| Guanine | G |
| Cytosine | C |
| Uracil | U |

As used herein, a "polynucleotide" refers to a polymeric chain containing two or more nucleotides. "Polynucleotides" includes primers, oligonucleotides, nucleic acid strands, etc. A polynucleotide may contain standard or non-standard nucleotides. Typically, a polynucleotide contains a 5' phosphate at one terminus ("5' terminus") and a 3' hydroxyl group at the other terminus ("3' terminus) of the chain. The most 5' nucleotide of a polynucleotide may be referred to herein as the "5' terminal nucleotide" of the polynucleotide. The most 3' nucleotide of a polynucleotide may be referred to herein as the "3' terminal nucleotide" of the polynucleotide.

As used herein, a "target" nucleic acid or molecule refers to a nucleic acid of interest. A target nucleic acid/molecule may be of any type, including single-stranded or double stranded DNA or RNA (e.g. mRNA).

As used herein, a nucleic acid molecule which is described as containing the "sequence" of a template or other nucleic acid may also be considered to contain the template or other nucleic acid itself (e.g. a molecule which is described as containing the sequence of a template may also be described as containing the template), unless the context clearly dictates otherwise.

As used herein, "complementary" sequences refer to two nucleotide sequences which, when aligned anti-parallel to each other, contain multiple individual nucleotide bases which pair with each other. It is not necessary for every nucleotide base in two sequences to pair with each other for sequences to be considered "complementary". Sequences may be considered complementary, for example, if at least 30%, 40%, 50%, 55%, 60%, 65%, 70%, 75%, 80%, 85%, 90%, 95%, 98%, 99%, or 100% of the nucleotide bases in two sequences pair with each other. In addition, sequences may still be considered "complementary" when the total lengths of the two sequences are significantly different from each other. For example, a primer of 15 nucleotides may be considered "complementary" to a longer polynucleotide containing hundreds of nucleotides if multiple individual nucleotide bases of the primer pair with nucleotide bases in the longer polynucleotide when the primer is aligned anti-parallel to a particular region of the longer polynucleotide.

As used herein, a "concatemer" refers to a nucleic acid molecule which contains within it two or more copies of a particular nucleic acid, wherein the copies are linked in series. Within the concatemer, the copies of the particular nucleic acid may be linked directly to each other, or they may be indirectly linked (e.g. there may be nucleotides between the copies of the particular nucleic acid). In an example, the particular nucleic acid may be that of a double-stranded nucleic acid template, such that a concatemer may contain two or more copies of the double-stranded nucleic acid template. In another example, the particular nucleic acid may be that of a polynucleotide template, such that a concatemer may contain two or more copies of the polynucleotide template.

As used herein, a "saccharide" is a molecule comprising one, a few, or multiple sugar moieties, and includes monosaccharides, oligosaccharides, and polysaccharides.

As used herein, a protein comprises a molecule made up of amino acids, the amino acids covalently linked by amide bonds. The terms "peptide", "polypeptide" and "protein" may be used interchangeably to refer to molecules comprised of amino acids linked by peptide bonds. Individual amino acids may be termed "residues" of a polypeptide or protein. The amino acid sequences of polypeptides disclosed herein may be identified by SEQ ID NO: presented as a string of letters, where the letters have the following meanings

TABLE 1B

| AminoAcid | 3-Letter Code | 1-Letter Code |
|---|---|---|
| Alanine | Ala | A |
| Arginine | Arg | R |
| Asparagine | Asn | N |
| Aspartic acid | Asp | D |
| Cysteine | Cys | C |
| Glutamic acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |

TABLE 1B-continued

| AminoAcid | 3-Letter Code | 1-Letter Code |
|---|---|---|
| Proline | Pro | P |
| Serine | Ser | S |
| Threonine | Thr | T |
| Tryptophan | Trp | W |
| Tyrosine | Tyr | Y |
| Valine | Val | V |

As used herein, a "cytokine" is a naturally occurring protein molecules often released in mammals in response to injury, infection, inflammation, or other stressor. Cytokines include lymphokines, interleukins, chemokines, interferons, and other cytokines Cytokines may be inflammatory cytokines (tending to cause inflammation; also termed pro-inflammatory cytokines) or may be anti-inflammatory cytokines (tending to suppress inflammation). Inflammatory cytokines include, for example, interleukin-1 (IL-1), interleukin-6 (IL-6), interleukin-12 (IL-12), interleukin-18 (IL-18), gamma interferon (IFN-γ), and tumor necrosis factor alpha (TNF-α). Anti-inflammatory cytokines include, for example, interleukin-10 (IL-10). Some cytokines may have multiple actions or effects (e.g., interleukin-6 (IL-6) has both inflammatory and anti-inflammatory effects).

As used herein, the terms "marker of inflammation", "inflammatory marker", and plurals and grammatical equivalents thereof refer to markers which may be detected in a sample, and which may be identified in a sample, which indicate the presence of, or level of, inflammation in the subject from which the sample was obtained. Markers of inflammation include both peptide and non-peptide markers; for example, markers of inflammation include, without limitation, prostaglandins, tumor necrosis factor alpha (TNF-α), interleukin-1 (IL-1), interleukin-8 (IL-8), interleukin-12 (IL-12), interferon gamma (IF-γ), bradykinin, complement system molecules, blood-clotting factors, C-reactive protein, erythrocyte sedimentation rate (ESR), white blood cell count, and morphological changes in blood and other cells.

The term "antibody" is used in the broadest sense and specifically covers single monoclonal antibodies (including agonist and antagonist antibodies), antibody compositions with polyepitopic specificity, and antibody fragments, and includes human an humanized antibodies. Monoclonal antibodies are obtained from a population of substantially homogeneous antibodies, i.e., the individual antibodies comprising the population are identical except for possible naturally-occurring mutations that may be present in minor amounts. The most abundant class of antibodies is the IgG class, characterized by having molecular weights of about 150 kD.

The term "monoclonal antibody" (mAb) as used herein refers to an antibody obtained from a population of substantially homogeneous antibodies, i.e., the individual antibodies comprising the population are identical except for possible naturally occurring mutations that may be present in minor amounts. For example, monoclonal antibodies may be made by the hybridoma method first described by Kohler et al., Nature, 256:495 (1975), or may be made by recombinant DNA methods (see, e.g., U.S. Pat. No. 4,816,567 to Cabilly et al.).

The term "intact antibody" refers to the complete antibody, or the amino acid sequence of the complete antibody, of which an antibody fragment is a part. It will be understood that an antibody fragment may be produced by partial digestion (e.g., by papain or pepsin) of an intact antibody, or may be produced by recombinant or other means.

"Antibody fragment", and all grammatical variants thereof, as used herein is defined as a (1) portion of an intact antibody comprising the antigen binding site or variable region of the intact antibody, wherein the portion is free of the constant heavy chain domains of the Fc region of the intact antibody, and (2) constructs comprising a portion of an intact antibody (as defined by the amino acid sequence of the intact antibody) comprising the antigen binding site or variable region of the intact antibody.

An antibody fragment is, or comprises, a polypeptide having a primary structure consisting of one uninterrupted sequence of contiguous amino acid residues having the amino acid sequence of an intact antibody. Examples of antibody fragments include Fab, Fab', Fab'-SH, F(ab')$_2$, Fd, Fc, Fv, diabodies, and any other "Non-single-chain antigen-binding unit" as described, e.g., in U.S. Pat. No. 7,429,652.

The term "diabodies" refers to small antibody fragments with two antigen-binding sites, which fragments comprise a heavy chain variable domain connected to a light chain variable domain in the same polypeptide chain. By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA, 90:6444-6448 (1993).

As used herein, an "antigen-binding antibody fragment" is any antibody fragment that retains the ability to bind to the specific target to which the intact antibody specifically binds. An antigen-binding antibody fragment may have different (e.g., lesser) binding affinity for the target antigen than the intact antibody. As used herein, unless otherwise stated, an antibody fragment is an antigen-binding antibody fragment An antibody that "specifically binds to" or is "specific for" a particular polypeptide or, an epitope on a particular polypeptide is one that binds to that particular polypeptide or epitope on a particular polypeptide without substantially binding to any other polypeptide or polypeptide epitope.

The terms "antigen", "target molecule", "target polypeptide", "target epitope", and the like are used herein to denote the molecule specifically bound by an antibody or antibody fragment.

As used herein, a "marker", a "label", a "marker moiety" and a "label moiety" refer to a detectable compound or composition which is conjugated directly or indirectly to the antibody so as to generate a "labeled" antibody. A label or marker provides a detectable signal for at least the time period during which a signal is to be observed. The label or marker may be detectable by itself (e.g. radioisotope labels or fluorescent labels) or, in the case of an enzymatic label, may catalyze chemical alteration of a substrate compound or composition which is detectable.

A label or marker moiety may be, for example, a dye, an epitope tag, a fluorescent moiety, a luminescent moiety, a chemiluminescent moiety, an enzymatic label, a magnetic label, a paramagnetic label, a contrast agent, a nanoparticle, a radioisotope, biotin, streptavidin, and a quencher. A nanoparticle may be a particle of an element, such as a gold nanoparticle, or of an alloy or compound, such as a quantum dot (a particle of a semiconductor material), or other particle having a size typically in a range between about 1 nm to about 100 nm.

A label or marker moiety may provide a signal by reflecting, or modulating, energy impinging on the label or marker moiety. A label or marker moiety may provide a signal by emitting, or by increasing, a detectable signal. Similarly, a label or marker moiety may provide a signal by diminishing, or extinguishing, a signal (e.g., the quenching of a signal). It will be understood that a label or marker moiety may be directly detectable (e.g., may provide a detectable signal without further action or input of energy), or may use or require energy, a substrate, a binding partner, or other action in order to provide a detectable signal. An enzymatic label may be suitable for use with a binding partner or substrate; for example, a peroxidase such as horseradish peroxidase may serve as a label as it may be used to detect the presence of a target, or to measure the amount of target, when used with, e.g., diaminobenzidine or other molecule suitable for use with a peroxidase; for another, non-limiting example, luciferase may serve as a label as it may be used to detect the presence of a target, or to measure the amount of target, when used with luciferin.

As used herein, the term "chromogen" refers to a compound which may be readily converted into a dye or other colored compound.

As used herein, "BSA" means bovine serum albumin; "PEG" means polyethylene glycol; "ELISA" means enzyme-linked immunosorbent assay; and other terms, abbreviations, and acronyms have the standard meanings understood in the chemical and biological arts.

A composition may include a buffer. Buffers include, without limitation, phosphate, citrate, ammonium, acetate, carbonate, tris(hydroxymethyl)aminomethane (TRIS), 3-(N-morpholino) propanesulfonic acid (MOPS), 3-morpholino-2-hydroxypropanesulfonic acid (MOPSO), 2-(N-morpholino)ethanesulfonic acid (MES), N-(2-Acetamido)-iminodiacetic acid (ADA), piperazine-N,N'-bis(2-ethanesulfonic acid) (PIPES), N-(2-Acetamido)-2-aminoethanesulfonic acid (ACES), cholamine chloride, N,N-Bis(2-hydroxyethyl)-2-aminoethanesulfonic acid (BES), 2-[[1,3-dihydroxy-2-(hydroxymethyl)propan-2-yl]amino]ethanesulfonic acid (TES), 4-(2-hydroxyethyl)-1-piperazine ethanesulfonic acid (HEPES), acetamidoglycine, tricine (N-(2-Hydroxy-1,1-bis(hydroxymethyl)ethyl)glycine), glycinamide, and bicine (2-(Bis(2-hydroxyethyl)amino)acetic acid) buffers. Buffers include other organic acid buffers in addition to the phosphate, citrate, ammonium, acetate, and carbonate buffers explicitly mentioned herein.

A composition may include a physiologically acceptable carrier. For example, a physiologically acceptable carrier may be an aqueous pH buffered solution. Examples of physiologically acceptable carriers include buffers such as phosphate, citrate, and other organic acids as discussed above; antioxidants including ascorbic acid; low molecular weight (less than about 10 residues) polypeptides; proteins, such as, e.g., serum albumin, gelatin, cytochromes, and immunoglobulins; hydrophilic polymers such as polyvinylpyrrolidone; amino acids such as glycine, glutamine, asparagine, arginine or lysine; monosaccharides, disaccharides, polysaccharides, and other carbohydrates including glucose, mannose, and dextrins; chelating agents such as ethylene diamine tetraacetic acid (EDTA); sugar alcohols such as mannitol or sorbitol; salt-forming counterions such as sodium, potassium, calcium, magnesium and others; nonionic surfactants such as TWEEN™, polyethylene glycol (PEG), and PLURONICS™; and/or other compounds known in the art.

For example, a composition may include albumin, gelatin, cytochrome C, an immunoglobulin, an amino acid, agar, glycerol, ethylene glycol, a protease inhibitor, an antimicrobial agent, a metal chelating agent, a monosaccharide, a disaccharide, a polysaccharide, a reducing agent, a chelating agent, or combinations thereof.

As used herein, a "sample", or "biological sample", or "clinical sample" refers to a sample of fluid, tissue, secretion, or excretion obtained from a subject. A sample, biological sample, or clinical sample may be a sample of blood, serum, plasma, saliva, sputum, urine, gastric fluid, digestive fluid, tears, sweat, stool, semen, vaginal fluid, interstitial fluid, fluid derived from tumorous tissue, ocular fluids, mucus, earwax, oil, glandular secretions, spinal fluid, skin, cerebrospinal fluid from within the skull, tissue, fluid or material from a nasal swab, a throat swab, a mouth swab (e.g., a cheek swab), a vaginal swab, or nasopharyngeal wash, biopsy fluid or material, placental fluid, amniotic fluid, cord blood, lymphatic fluids, cavity fluids, pus, microbiota obtained from a subject, meconium, breast milk, or other secretion or excretion. A sample may be a breath sample, a hair sample, a fingernail sample, or other sample.

Biological and clinical samples may include nasopharyngeal wash, or other fluid obtained by washing a body cavity or surface of a subject, or by washing a swab following application of the swab to a body cavity or surface of a subject. Nasal swabs, mouth swabs (including cheek swabs), throat swabs, vaginal swabs, stool samples, hair, finger nail, ear wax, breath, and other solid, semi-solid, or gaseous samples may be processed in an extraction buffer, e.g., for a fixed or variable amount of time, prior to their analysis. The extraction buffer or an aliquot thereof may then be processed similarly to other fluid samples if desired. Examples of tissue samples of the subject may include but are not limited to, connective tissue, muscle tissue, nervous tissue, epithelial tissue, cartilage, cancerous sample, or bone. The sample may be obtained from a human or animal. The sample may be obtained from a vertebrate, e.g., a bird, fish, or mammal, such as a rat, a mouse, a pig, an ape, another primate (including humans), a farm animal, a sport animal, or a pet. The sample may be obtained from a living or dead subject. The sample may be obtained fresh from a subject or may have undergone some form of pre-processing, storage, or transport.

As used herein, a "small volume" refers to a volume of less than about 1 mL, or less than about 500 µL, or less than about 250 µL, or less than 150 µL, or less than about 100 µL, or less than about 50 µL, or less than about 25 µL, or less. In particular embodiments, a small volume, such as a "finger-stick" volume, may comprise less than about 250 µL, and typically comprises less than 150 µL, or less than about 100 µL, or less than about 50 µL, or less than about 25 µL, or less.

A sample may be divided into two or more portions. As used herein, when referring to a sample or samples, the terms "portion" and "aliquot" and their plurals and grammatical equivalents are used interchangeably to refer to a fractional amount of sample taken from an original complete sample. Such a fraction may be any fraction or amount, so that a portion or aliquot may comprise most of the original sample, a large fraction of the original sample, a small fraction of the original sample, or a relatively small fraction of the original sample. The phrases "at least a portion", "at least an aliquot", and the like, may refer both to a fractional part of an original sample and to the entire original sample.

Detection of markers, and detection of disease-causing (or other) organisms may include detection of nucleic acid markers; detection of protein (peptide) markers, including detection of antibodies; detection of markers of inflammation (including both peptide and non-peptide markers); and detection of other markers. Identification of markers, and of disease-causing (or other) organisms may include identification of nucleic acid markers; identification of protein (peptide) markers, including identification of antibodies; identification of markers of inflammation (including both peptide and non-peptide markers); and identification of other markers. Detection and identification of markers and organisms may include quantitative detection and identification of such markers and such organisms.

A method may be performed in a short period of time. A device may be capable of performing all steps of a method in a short period of time. A device may be capable of performing all steps of a method on a single sample in a short amount of time. A device may be capable of performing all steps of a method on two samples, such as a blood sample and a sample obtained from a swab, in a short amount of time. A device may be capable of performing all steps of a method on more than two samples in a short amount of time. For example, from sample collection from a subject to detecting a disease marker, or to detecting multiple disease markers, may take about 3 hours or less, 2 hours or less, 1 hour or less, 50 minutes or less, 45 minutes or less, 40 minutes or less, 30 minutes or less, 20 minutes or less, 15 minutes or less, 10 minutes or less, 5 minutes or less, 4 minutes or less, 3 minutes or less, 2 minutes or less, or 1 minute or less. For example, from sample collection from a subject to transmitting data regarding, and/or to analysis of, a sample or samples may take about 3 hours or less, 2 hours or less, 1 hour or less, 50 minutes or less, 45 minutes or less, 40 minutes or less, 30 minutes or less, 20 minutes or less, 15 minutes or less, 10 minutes or less, 5 minutes or less, 4 minutes or less, 3 minutes or less, 2 minutes or less, or 1 minute or less.

For example, the period of time from initiating a method of detecting a disease marker to detecting a disease marker, or to detecting multiple disease markers, may be about 3 hours or less, 2 hours or less, 1 hour or less, 50 minutes or less, 45 minutes or less, 40 minutes or less, 30 minutes or less, 20 minutes or less, 15 minutes or less, 10 minutes or less, 5 minutes or less, 4 minutes or less, 3 minutes or less, 2 minutes or less, or 1 minute or less. For example, the period of time from initiating a method of detecting a disease marker to transmitting data regarding such detection may be about 3 hours or less, 2 hours or less, 1 hour or less, 50 minutes or less, 45 minutes or less, 40 minutes or less, 30 minutes or less, 20 minutes or less, 15 minutes or less, 10 minutes or less, 5 minutes or less, 4 minutes or less, 3 minutes or less, 2 minutes or less, or 1 minute or less.

The period of time from accepting a sample within the device to detecting a disease marker, or to detecting a plurality of disease markers, or to transmitting data regarding, and/or to analysis of, a sample or samples may depend on the type or number of steps, tests, or assays performed on the sample or samples. The amount of time from accepting a sample, or samples, within the device to detecting a disease marker or markers, or to transmitting data and/or to analysis from the device regarding such a sample or samples may take about 3 hours or less, 2 hours or less, 1 hour or less, 50 minutes or less, 45 minutes or less, 40 minutes or less, 30 minutes or less, 20 minutes or less, 15 minutes or less, 10 minutes or less, 5 minutes or less, 4 minutes or less, 3 minutes or less, 2 minutes or less, or 1 minute or less.

Thus, as used herein, a "short period of time" refers to a period of time of about 5 hours or less, or about 4 hours or less, or about 3 hours or less, or about 2 hours or less, or about 1 hour or less, or about 50 minutes or less, or about 40 minutes or less, or about 30 minutes or less, or about 20 minutes or less, or about 10 minutes or less, or about 5 minutes or less. A short period of time may be determined with respect to an initial time; the initial time may be the time at which a sample analysis began; the initial time may be the time at which a sample is inserted into a device for the analysis of the sample; the initial time may be the time at which a sample was obtained from a subject.

The terms "point of service" (abbreviated POS) and "point of service system," as used herein, refer to a location, and a system at that location, that is capable of providing a service (e.g. testing, monitoring, treatment, diagnosis, guidance, sample collection, verification of identity (ID verification), and other services) at or near the site or location of the subject. A service may be a medical service, and may be a non-medical service. In some situations, a POS system provides a service at a predetermined location, such as a subject's home, school, or work, or at a grocery store, a drug store, a community center, a clinic, a doctor's office, a hospital, etc. A POS system can include one or more point of service devices. In some embodiments, a POS system is a point of care system.

A "point of care" (abbreviated POC) is a location at which medical-related care (e.g. treatment, testing, monitoring, diagnosis, counseling, etc.) is provided. A POC may be, e.g. at a subject's home, work, or school, or at a grocery store, a community center, a drug store, a doctor's office, a clinic, a hospital, etc. A POC system is a system which may aid in, or may be used in, providing such medical-related care, and may be located at or near the site or location of the subject or the subject's health care provider (e.g. subject's home, work, or school, or at a grocery store, a community center, a drug store, a doctor's office, a clinic, a hospital, etc.).

As used herein, the term "immunoassay" refers to any assay which detects, identifies, characterizes, quantifies, or otherwise measures an amino acid target in a sample (where an amino acid target may be a small peptide, a polypeptide, a protein, or proteinaceous macromolecule). Immunoassays include, for example, direct or competitive binding assays using techniques such as western blots, radioimmunoassays, ELISA (enzyme linked immunosorbent assay), "sandwich" immunoassays, immunoprecipitation assays, fluorescent immunoassays, and protein A immunoassays. Immunoassays typically use antibodies or antibody fragments, but may also use binding proteins or carrier proteins which bind target molecules with high specificity.

As used herein, the term "nucleic acid assay" is used to refer to any assay which detects, identifies, characterizes, quantifies, or otherwise measures a nucleic acid target in a sample (where a nucleic acid target may be a single stranded, double stranded, or other nucleic acid molecule of any size. Nucleic acid assays include polymerase chain reaction (PCR) assays (see, e.g. U.S. Pat. No. 4,683,202), loop-mediated isothermal amplification ("LAMP") (see, e.g. U.S. Pat. No. 6,410,278), and other methods, including methods discussed below for detecting nucleic acid targets in a sample. Nucleic acid markers may be detected by any suitable means, including means that include nucleic acid amplification (e.g., thermal cycling amplification methods including PCR, and other nucleic acid amplification methods; isothermal amplification methods, including LAMP, etc.) and any other method that can be used to detect the presence of nucleic acid markers indicative of a disease-causing organism in a sample.

As used herein, the term "general chemistry assay" refers to any assay which detects, identifies, characterizes, quantifies, or otherwise measures a target in a sample, other than a target which is a nucleic acid or other than by use of an antibody or other specifically binding protein. General chemistry assays include, e.g., assays for electrolytes; for vitamin levels; for blood component levels; for trace metals; for lipids; and other targets). General chemistry assays may include, for example, assays of a Basic Metabolic Panel [glucose, calcium, sodium (Na), potassium (K), chloride (Cl), $CO_2$ (carbon dioxide, bicarbonate), creatinine, blood urea nitrogen (BUM], assays of an Electrolyte Panel [sodium (Na), potassium (K), chloride (Cl), $CO_2$ (carbon dioxide, bicarbonate)], assays of a Chem 14 Panel/Comprehensive Metabolic Panel [glucose, calcium, albumin, total protein, sodium (Na), potassium (K), chloride (Cl), $CO_2$ (carbon dioxide, bicarbonate), creatinine, blood urea nitrogen (BUN), alkaline phosphatase (ALP), alanine aminotransferase (ALT/GPT), aspartate aminotransferase (AST/GOT), total bilirubin] assays of a Lipid Profile/Lipid Panel [LDL cholesterol, HDL cholesterol, total cholesterol, and triglycerides], assays of a Liver Panel/Liver Function [alkaline phosphatase (ALP), alanine aminotransferase (ALT/GPT), aspartate aminotransferase (AST/GOT), total bilirubin, albumin, total protein, gamma-glutamyl transferase (GGT), lactate dehydrogenase (LDH), prothrombin time (PT)], alkaline phosphatase (APase), hemoglobin, VLDL cholesterol, ethanol, lipase, pH, zinc protoporphyrin, direct bilirubin, blood typing (ABO, RHD), lead, phosphate, hemagglutination inhibition, magnesium, iron, iron uptake, fecal occult blood, and others, individually or in any combination.

As used herein the term "cytometric assay" refers to any which detects, identifies, characterizes, quantifies, or otherwise measures a cell or large particle (e.g., a crystal) in a sample. Cytometric assays typically utilize imaging of other light-based techniques to detect, measure, characterize, and quantify cells and particles in a sample.

Systems, Devices, and Methods

In embodiments, Applicants disclose systems, including such systems discussed above, for detecting one or more of a plurality of disease-causing agents in a clinical sample. In embodiments, Applicants disclose systems, including such systems discussed above, for detecting one or more of a plurality of disease-causing agents in a clinical sample, wherein said diseases comprise respiratory diseases. In embodiments, Applicants disclose systems, including such systems discussed above, for detecting one or more of a plurality of disease-causing agents in a clinical sample, wherein said disease-causing agents cause respiratory diseases selected from viral diseases, bacterial diseases, fungal diseases, *mycoplasma* diseases, and other diseases.

In embodiments, the plurality of disease-causing agents causes a number of diseases, wherein said number of diseases comprises 8 or more diseases, or 10 or more diseases, or 12 or more diseases, or 14 or more diseases, or 16 or more diseases, or 18 or more diseases, or 20 or more diseases, or 30 or more diseases, or 40 or more diseases, or 50 or more diseases, or 60 or more diseases, or more. In embodiments, the plurality of disease-causing agents causes a number of diseases, wherein said diseases are selected from viral diseases, bacterial diseases, fungal diseases, *mycoplasma* diseases, and other diseases.

In embodiments, the systems disclosed herein, and the methods disclosed herein, may be used to perform all of a plurality of assays on a single small volume sample, or an aliquot or aliquots thereof. In embodiments, a small volume sample has a volume selected from no more than about 1 mL, or no more than about 500 μL, or no more than about 250 μL, or no more than about 150 μL, or no more than about 100 µL, or no more than about 75 µL, or no more than about 50 µL, or no more than about 25 µL, or no more than about 15 µL, or no more than about 10 µL, or no more than about 5 µL, or no more than about 4 µL, or no more than about 3 µL, or no more than about 2 µL, or no more than about 1 µL, or less than about 1 µL.

In embodiments, the systems disclosed herein, and the methods disclosed herein, may be used to perform all of a plurality of assays in a short time period. In embodiments, such a short time period comprises less than about three hours, or less than about 2 hours, or less than about 1 hour, or less than about 50 minutes, or less than about 45 minutes, or less than about 40 minutes, or less than about 30 minutes, or less than about 20 minutes, or less than about 15 minutes, or less than about 10 minutes, or less than about 5 minutes, or less than about 4 minutes, or less than about 3 minutes, or less than about 2 minutes, or less than about 1 minute.

In embodiments, the plurality of disease-causing agents may cause a number of diseases, wherein said disease-causing agents are selected from *mycobacterium tuberculosis, staphylococcus aureus* (including methicillin-resistant *staphylococcus aureus*), *streptococcus* (including *streptococcus* Group A and *streptococcus* Group B), *bordetella pertussis*, adenovirus (including adenovirus B, adenovirus C, and adenovirus E), influenza, parainfluenza, respiratory syncytial virus (RSV), adenovirus, corona virus, bocavirus, *haemophilus parainfluenzae*, human papilloma virus (HPV), hepatitis, human inmmunodeficiency virus (HIV), herpes simplex virus (HSV), West Nile, Epstein Barr, Rhinovirus, and other viruses. In embodiments, the plurality of disease-causing agents causes a number of diseases, wherein said disease-causing agents are selected from *streptococcus, staphylococcus, bordetella pertussis*, tuberculosis, enterobacteria, *pseudomonas*, dengue, malaria, trypanosome *cruzi, treponema pallidum, mycoplasma, chlamydia, Moraxella catarrhalis, acinetobacter, legionella, Escherichia coli, candida, chlamydia, Neisseria, trichomonas*, and other microorganismal disease-causing agents, including but not limited to disease-causing agents named elsewhere herein.

In embodiments, the plurality of disease-causing agents may cause a number of respiratory diseases, wherein said number of respiratory diseases comprises 8 or more respiratory diseases, or 10 or more respiratory diseases, or 12 or more respiratory diseases, or 14 or more respiratory diseases, or 16 or more respiratory diseases, or 18 or more respiratory diseases, or 20 or more respiratory diseases, or 30 or more respiratory diseases, or 40 or more respiratory diseases, or 50 or more respiratory diseases, or 60 or more respiratory diseases, or more.

In embodiments, the plurality of disease-causing agents may cause a number of respiratory diseases, wherein said respiratory diseases are selected from viral diseases, bacterial diseases, fungal diseases, *mycoplasma* diseases, and other diseases.

In embodiments, the plurality of disease-causing agents may cause a number of respiratory diseases, wherein said respiratory disease-causing agents are selected from *mycobacterium tuberculosis, staphylococcus aureus* (including methicillin-resistant *staphylococcus aureus*), *streptococcus* (including *streptococcus* Group A), *bordetella pertussis*, adenovirus (including adenovirus B, adenovirus C, and adenovirus E). In embodiments, respiratory disease-causing agents may further include one or more of influenza, parainfluenza, respiratory syncytial virus (RSV), adenovirus, corona virus, bocavirus, *haemophilus parainfluenzae*, human papilloma virus (HPV), hepatitis, human inmmunodeficiency virus (HIV), herpes simplex virus (HSV), West Nile, Epstein Barr, Rhinovirus, and other viruses.

In embodiments, the plurality of disease-causing agents may cause influenza. In embodiments, the influenza may be selected from influenza A, influenza B, H1N1 influenza (including seasonal and novel forms of influenza H1N1), H3N2 influenza, H7N9 influenza, H5N1 influenza, and other influenzas.

In embodiments, the plurality of disease-causing agents may cause a sexually transmitted disease. In embodiments, the sexually transmitted disease is selected from herpes simplex virus (HSV), human immunodeficiency virus (HIV, including HIV-1, HIV-2, including HIV-2 Group A), gonorrhea, syphilis, human papilloma virus (PPV), *streptococcus* (including *streptococcus* B), *treponema pallidum*, and other sexually transmitted diseases.

Further targets include drug-resistant micro-organisms, including those exhibiting multi-drug resistance. Drug resistance (also termed antibiotic resistance) is found where a population (or subpopulation) of a micro-organism, such as a bacterium, acquires or exhibits resistance to one or more drugs (e.g., to one or more antibiotic). Micro-organisms that are resistant to treatment by multiple drugs are termed to be "multi-drug resistant" and those micro-organisms are termed to have or to exhibit "multi-drug resistance"; either term may be abbreviated by "MDR". Resistance to one or more drugs is observed, or exhibited, when a population of micro-organisms survives (and typically continues to grow and multiply in number) despite the presence of a drug, or (in the case of MDR) despite the presence of multiple drugs. Drug-resistant organisms of particular interest include, but are not limited to, Methicillin-Resistant *Staphylococcus aureus* (MRSA), vancomycin-intermediate *S. aureus* (VISA), vancomycin-resistant *S. aureus* (VRSA), bacteria (e.g., Enterobacteriaceae) having extended spectrum beta-lactamase (ESBL), Vancomycin-resistant *Enterococcus* (VRE), and Multidrug-resistant *A. baumannii* (MRAB). Drug-resistant target organisms, including MDR target organisms, may be identified by nucleic acid markers, protein (or peptide) markers, other markers, or combinations thereof, as well as by observing their growth in the presence of drugs.

Many antibiotic compounds include a β-lactam ring (a ring of four carbons); for example, penicillin is an antibiotic having a β-lactam ring. Many bacteria have β-lactamase enzymes which can cleave a β-lactam ring, and thus protect the bacteria against such antibiotics. Enzymes that can cleave a β-lactam ring, which are often found in Gram-negative bacteria, include the TEM and ROB β-lactamase enzymes. Drug-resistant *Haemophilus influenzae* bacteria may have the blaTEM or blaROB resistance gene (typically blaTEM-1, although blaTEM-2 and blaROB-1 and others are also found); other drug-resistance markers found in disease-causing organisms include the KPC resistance gene (found in *Klebsiella* pneumonia carbapenemas (KPC)); mecA and mecC resistance genes (responsible for resistance to β-lactam-containing antibiotics such as methicillin); vancomycin resistance genes A and B (vanA and vanB) may be found in disease-causing bacteria, such as, e.g., vancomycin resistant Enterococci; and others drug-resistance markers.

Disease-causing organisms of interest include viruses of the filoviridae family of viruses (filo viruses), which includes Ebola viruses, Marburg viruses, and Cueva viruses. Ebola viruses cause ebola virus disease (also known as Ebola hemorrhagic fever); Marburg viruses also cause a hemorrhagic fever, the Marburg hemorrhagic fever; and Cueva viruses such as lloviu virus (LLOV), may be endemic in France, Spain, or Portugal. Such viruses may be detected and may be identified in a sample from nucleic acid markers specific to these viruses, from protein (peptide) markers specific to these viruses, and from other markers specific to these viruses.

Filo viruses typically cause hemorrhagic fevers and related disorders. These and other diseases may be detected, and may be identified, by identifying nucleic acid markers, peptide markers, and other markers, alone or in combination, as disclosed herein. Filo viral diseases, other hemorrhagic fevers, and other diseases including many tropical diseases, e.g. Dengue 1, Dengue 2, Dengue 3, Dengue 4, malaria, typhoid, and other diseases, have many detrimental effects, including hemorrhage and internal bleeding, and may cause disruptions in electrolytes, may cause anemia, and may cause other symptoms and effects. Integrated electrolyte assays (e.g., for sodium, potassium, and other electrolytes, including sodium and potassium together, and including sodium and potassium together with other electrolytes) may identify subjects suffering from electrolyte imbalances, and may thus identify subjects suffering from a hemorrhagic fever, from anemia, or both. Assays for hemoglobin, for iron, and other assays may identify subjects suffering from anemia, from a hemorrhagic fever, or both. Anemia may be due to hemorrhage, parasitic infection (e.g., hookworm), both hemorrhage and parasitic infection, and other causes. Thus, in addition to testing for nucleic acid, peptide, and other markers, these hemorrhagic and other diseases may be detected, and may be identified, with integrated electrolyte measurements; with hemoglobin measurements; with iron measurements; and with other general chemistry assays, alone or in combination. In embodiments, integrated electrolyte measurements, hemoglobin, iron, or other general chemistry assays may provide indications that a subject suffers from anemia, a hemorrhagic fever such as Ebola, Marburg, or other disease such as malaria or typhoid fever; such indication may be used to suggest further testing for markers of such diseases. Thus, in embodiments, electrolyte testing including sodium and potassium, or other general chemistry assays, may be performed simultaneously when testing for Ebola, Marburg, or other hemorrhagic disease (e.g., when testing for nucleic acid, peptide, or other markers for such diseases).

In embodiments, such indications derived from general chemistry test results (e.g., from the results of integrated electrolyte measurements, hemoglobin, iron, or other general chemistry assays) may automatically trigger reflex testing for one or more hemorrhagic fever disease markers, or malaria, typhoid fever, or other disease marker, and may automatically trigger reflex testing for combinations or for all of such markers. In embodiments, a subject may be tested for other diseases and not (initially) for Ebola, Marburg, or other hemorrhagic disease (e.g., a patient that is weak, or feverish, may not initially be tested for Ebola, Marburg, or other hemorrhagic disease); based on the results of integrated electrolyte measurements, hemoglobin, iron, or other general chemistry assays, a reflex test for Ebola, Marburg, or other hemorrhagic disease may be automatically performed, or may be ordered by a health care professional. In embodiments, a patient or subject may not wish to be tested for Ebola, Marburg, or other hemorrhagic disease, or other disease of concern (e.g., a patient may fear quarantine, or may fear that the cost of the test might be prohibitive) and thus may not initially be tested for Ebola, Marburg, or other hemorrhagic disease; based on the results of integrated electrolyte measurements, hemoglobin, iron, or other general chemistry assays, a reflex test for Ebola, Marburg, or other hemorrhagic disease may be automatically performed, or may be ordered by a health care professional. In embodiments, such a reflex test for Ebola, Marburg, or other hemorrhagic disease, or other disease of concern may be performed if the patient is first tested for one or more infectious disease other than Ebola, Marburg, or other hemorrhagic disease, and the initial test panel does not show infection of any known disease (and thus further testing would be required in order to identify other possible sources of the subject's disease or condition).

Methods, devices, and systems disclosed herein may be used to detect, and may be used to identify, disease-causing organisms in normal or healthy individuals and populations. Methods, devices, and systems disclosed herein may be used to detect, and may be used to identify, benign organisms in normal or healthy individuals and populations. Such disease-causing organisms and such benign organisms may be detected, and may be identified, in samples obtained from a normal individual, e.g., once or on an on-going basis, in order to determine a baseline or normal level for that individual when that individual is healthy. Such detection of disease-causing and benign organisms may include detection of nucleic acid markers; detection of protein (peptide) markers, including detection of antibodies; detection of markers of inflammation (including both peptide and non-peptide markers); and detection of other markers. Such identification of disease-causing and benign organisms may include identification of nucleic acid markers; identification of protein (peptide) markers, including identification of antibodies; identification of markers of inflammation (including both peptide and non-peptide markers); and identification of other markers. Detection and identification of markers may include quantitative detection and identification of such markers. Differences between the results from a sample and normal or baseline results may be used to improve the likelihood of detecting whether or not an individual suffers from a disease or condition. For example, determination of a baseline or normal level for an individual aids in detecting, in identifying, and in diagnosing disease conditions, or progression towards a disease or a detrimental condition, by comparison of results from later-obtained samples to baseline or normal levels determined when the individual as healthy. Such comparisons between an individual subject's results and baseline or normal levels found in prior results obtained from the individual when healthy can be used to determine if it is likely that the individual subject suffers from an infection. Such comparisons may include consideration of symptoms, if any, of that individual subject in comparison to symptoms (or the lack thereof) previously found for that individual when healthy.

Such disease-causing organisms and such benign organisms may be may be detected, and may be identified, in samples obtained from multiple individuals, e.g., once or on an on-going basis, in order to determine a baseline or normal level found in a normal (healthy) population. Such detection of disease-causing and benign organisms may include detection of nucleic acid markers; detection of protein (peptide) markers, including detection of antibodies; detection of markers of inflammation (including both peptide and non-peptide markers); and detection of other markers. Such identification of disease-causing and benign organisms may include identification of nucleic acid markers; identification of protein (peptide) markers, including identification of antibodies; identification of markers of inflammation (including both peptide and non-peptide markers); and identification of other markers. Detection and identification of markers may include quantitative detection and identification of such marker. Differences between the results obtained from a sample from an individual subject and normal or baseline results obtained from a population of comparable healthy individuals may be used to improve the likelihood of detecting whether or not an individual subject suffers from a disease or condition. For example, determination of a baseline or normal level for an individual subject aids in detecting, in identifying, and in diagnosing disease conditions, or progression towards a disease or a detrimental condition, by comparison of results for the individual subject to baseline or normal levels found in a population of comparable healthy individuals. Such comparisons between an individual subject's results and baseline or normal levels found in a healthy population can be used to determine if it is likely that the individual subject suffers from an infection. Such comparisons may include consideration of symptoms, if any, of that individual subject in comparison to symptoms (or the lack thereof) found in a healthy population.

In embodiments, such a system is a point-of-service system (POS system), wherein a POS system is located at a point of service location. In embodiments, a POS system is located at a point of service location and is configured to accept a clinical sample obtained from a subject at the POS location. In embodiments, a POS system is located at a point of service location and is configured to accept a clinical sample obtained from a subject at the POS location, and is further configured to analyze the clinical sample at the POS location. In embodiments, the clinical sample is a small volume clinical sample. In embodiments, the clinical sample is analyzed in a short period of time. In embodiments, the short period of time is determined with respect to the time at which sample analysis began. In embodiments, the short period of time is determined with respect to the time at which the sample was inserted into a device for the analysis of the sample. In embodiments, the short period of time is determined with respect to the time at which the sample was obtained from the subject.

Applicants disclose herein methods for detecting the presence of a target disease-causing agent, or marker indicative of the presence of a target disease-causing agent, in a single small-volume sample or aliquot thereof. In embodiments, methods for detecting the presence of a plurality of target disease-causing agents, or markers indicative thereof, from a single sample, or aliquot thereof, within a short period of time are disclosed. In embodiments, the plurality of target disease-causing agents, or markers indicative thereof, termed "targets", comprises at least 5 targets, or at least 10 targets, or at least 15 targets, or at least 20 targets, or at least 25 targets, or at least 30 targets, or at least 35 targets, or at least 40 targets, or at least 45 targets, or at least 50 targets, or at least 55 targets, or at least 60 targets, or at least 65 targets, or more. In embodiments, a short period of time is a period of time that is five hours or less, or is four hours or less, or is three hours or less, or is two hours or less, or is one hour or less, or is 50 minutes or less, or is 40 minutes or less, or is 30 minutes or less, or is 20 minutes or less, or is 10 minutes or less, or is 5 minutes or less.

Applicants disclose herein methods for detecting the presence of a target flu virus molecule in a sample are disclosed herein, wherein the presence of a plurality of possible target flu viruses are tested from a single sample within a short period of time. In embodiments, the plurality of possible target flu viruses comprise at least 5 possible target flu viruses, or at least 10 possible target flu viruses, or at least 15 possible target flu viruses, or at least 20 possible target flu viruses, or at least 25 possible target flu viruses, or at least 30 possible target flu viruses, or at least 35 possible target flu viruses, or at least 40 possible target flu viruses, or at least 45 possible target flu viruses, or at least 50 possible target flu viruses, or at least 55 possible target flu viruses, or at least 60 possible target flu viruses, or at least 64 possible target flu viruses, or at least 65 possible target flu viruses, or more.

Applicants further disclose herein methods for detecting the presence of a plurality of target molecules in a single sample within a short period of time, wherein the plurality of target molecules comprises nucleic acid molecules, or protein molecules, or saccharides, or cytokines, or steroids, or histamine, or other molecules. Applicants further disclose herein methods for detecting the presence of a plurality of target molecules in a single sample within a short period of time, wherein the plurality of target molecules comprises nucleic acid molecules and protein molecules. Applicants further disclose herein methods for detecting the presence of a plurality of target molecules in a single sample within a short period of time, wherein the plurality of target molecules comprises nucleic acid molecules, protein molecules, markers of inflammation, and cytokines Applicants further disclose herein methods for detecting the presence of a plurality of target molecules in a single sample within a short period of time, wherein the plurality of target molecules comprises nucleic acid molecules, protein molecules, and saccharides.

Applicants disclose herein devices for use in systems and methods as disclosed herein, Such devices include, for example, devices comprising a holder configured to accept and retain a clinical sample (e.g., a clinical sample contained within a sample collection device); a reagent vessel or a plurality of reagent vessels; and a reaction vessel, or a plurality of reaction vessels. In embodiments, such devices may further configured to accept and retain one or more of a cytometry cuvette or cuvettes; a waste container or containers; a tip, or tips, configured to aspirate or release fluid; and other tools.

Applicants further disclose herein assays for the detection of one or more of a plurality of target molecules in a single sample within a short period of time, wherein the plurality of target molecules comprises one or more of nucleic acid molecules, protein molecules, saccharides, markers of inflammation, and cytokines. In embodiments, such assays may be configured for use with systems and devices as disclosed herein.

Accordingly, Applicants disclose herein systems, devices, and methods, including the following exemplary integrated systems.

1) An integrated system for providing testing and diagnosis of a subject suspected of suffering from a disease, said system comprising a means for obtaining a sample (which may include, e.g., a sample collection device comprising a lancet, a syringe, a needle and tube, or other blood collection device; or a nasal swab, a mouth swab (e.g., a cheek swab), a throat swab, a vaginal swab, or other swab, and fluid in which to immerse the swab following contacting the swab with a subject); a cartridge comprising reagents for assays for the disease; a device for running a plurality of assays for detecting a plurality of diseases; a device/means for displaying/communicating the detection of one or more of said diseases. Such integrated systems may be configured for uses wherein the sample is a small volume sample; for uses wherein detection is performed in a short period of time; or for uses both wherein the sample is a small volume sample and wherein detection is performed in a short period of time.

2) An integrated system for providing testing and diagnosis of a subject suspected of suffering from a respiratory disorder, said system comprising a means for obtaining a sample (which may include, e.g., a nasal swab, a throat swab, a mouth swab (e.g., a cheek swab), a vaginal swab, or other swab, and fluid in which to immerse the swab following contacting the swab with a subject); a cartridge comprising reagents for assays for respiratory disorders; a device for running a plurality of assays for detecting a plurality of respiratory disorders; a device/means for displaying/communicating the detection of one or more of said respiratory disorders. Such integrated systems may be configured for uses wherein the sample is a small volume sample; for uses wherein detection is performed in a short period of time; or for uses both wherein the sample is a small volume sample and wherein detection is performed in a short period of time.

3) An integrated system for providing testing, diagnosis, and prescription of a subject suspected of suffering from a respiratory disorder, said system comprising a means for obtaining a sample (which may include, e.g., a nasal swab, a throat swab, a mouth swab (e.g., a cheek swab), a vaginal swab, or other swab, and fluid in which to immerse the swab following contacting the swab with a subject); a cartridge comprising reagents for assays for respiratory disorders; a device for running a plurality of assays for detecting a plurality of respiratory disorders; a device/means for displaying/communicating the detection of one or more of said respiratory disorders; and means for providing a prescription for the treatment of a respiratory disorder detected in said sample. Such integrated systems may be configured for uses wherein the sample is a small volume sample; for uses wherein detection is performed in a short period of time; or for uses both wherein the sample is a small volume sample and wherein detection is performed in a short period of time.

4) An integrated system for providing testing, diagnosis, prescription, and treatment of a subject suspected of suffering from a respiratory disorder, said system comprising a means for obtaining a sample (which may include, e.g., a nasal swab, a throat swab, a mouth swab (e.g., a cheek swab), a vaginal swab, or other swab, and fluid in which to immerse the swab following contacting the swab with a subject); a cartridge comprising reagents for assays for respiratory disorders; a device for running a plurality of assays for detecting a plurality of respiratory disorders; a device/means for displaying/communicating the detection of one or more of said respiratory disorders; means for providing a prescription for the treatment of a respiratory disorder detected in said sample; and means for providing/selling/delivering a treatment (drug/pill/shot) to said subject pursuant to said prescription. Such integrated systems may be configured for uses wherein the sample is a small volume sample; for uses wherein detection is performed in a short period of time; or for uses both wherein the sample is a small volume sample and wherein detection is performed in a short period of time.

Methods of detecting the presence of a target flu virus molecule in a sample are disclosed herein, wherein the presence of a plurality of possible target flu viruses are tested from a single sample within a short period of time. In embodiments, the plurality of possible target flu viruses comprise at least 5 possible target flu viruses, or at least 10 possible target flu viruses, or at least 15 possible target flu viruses, or at least 20 possible target flu viruses, or at least 25 possible target flu viruses, or at least 30 possible target flu viruses, or at least 35 possible target flu viruses, or at least 40 possible target flu viruses, or at least 45 possible target flu viruses, or at least 50 possible target flu viruses, or at least 55 possible target flu viruses, or at least 60 possible target flu viruses, or at least 64 possible target flu viruses, or at least 65 possible target flu viruses, or more. In embodiments, a short period of time is a period of time that is five hours or less, or is four hours or less, or is three hours or less, or is two hours or less, or is one hour or less, or is 50 minutes or less, or is 40 minutes or less, or is 30 minutes or less, or is 20 minutes or less, or is 10 minutes or less, or is 5 minutes or less.

Methods of detecting the presence of a respiratory disease-causing agent in a subject suspected of having a respiratory disorder, wherein the presence of a plurality of possible respiratory disease-causing agents are tested from a single sample using both nucleic acid testing and protein testing, wherein nucleic acid testing comprises detection of the presence of target nucleic acid sequences, and wherein protein testing comprises detection of the presence of target proteins having target amino acid sequences. In embodiments, target nucleic acid sequences may comprise sequences having at least 8 nucleotides, or at least 10 nucleotides, or at least 15 nucleotides, or at least 20 nucleotides, or at least 30 nucleotides, or at least 40 nucleotides, or at least 50 nucleotides, or more, that are identical, or closely similar, to target nucleotide sequences. In embodiments, target amino acid sequences may comprise sequences having at least 8 amino acids, or at least 10 amino acids, or at least 15 amino acids, or at least 20 amino acids, or at least 30 amino acids, or at least 40 amino acids, or at least 50 amino acids, or more, that are identical, or closely similar, to target amino acids sequences.

In embodiments, a respiratory disease-causing agent is detected if more than a minimum level of such respiratory disease-causing agents is detected in a small-volume sample obtained from a subject, wherein the small-volume sample is tested for the presence of a plurality of respiratory disease-causing agents. In embodiments, the small-volume sample is 150 µL or less in volume, or is 75 µL or less in volume, or is 50 µL or less in volume, or is 25 µL or less in volume, or is 15 µL or less in volume, or is 10 µL or less in volume, or is 5 µL or less in volume.

Embodiments of methods disclosed herein include methods in which a disease-causing agent is detected if more than a minimum level of such disease-causing agents is detected in a small-volume sample obtained from a subject. For example, such methods include methods wherein a small-volume sample is tested for the presence of a plurality of disease-causing agents. In embodiments of such methods, that minimum level may be set at a level that is determined by the condition of the subject. The minimum level may be set at a higher level for subjects who exhibit symptoms of active infection. The minimum level may be set at a lower level for subjects who are receiving treatment for an infection at the time the sample was obtained. The minimum level may be set at a lower level for subjects who have received treatment for an infection prior to the time the sample was obtained, e.g., who have recently received treatment for an infection prior to the time the sample was obtained.

In embodiments, the sample may be diluted prior to testing for the presence of a plurality of disease-causing agents. In embodiments, such dilution of a sample is greater for subjects who have a condition which indicates they may have higher levels of disease-causing agents than subject who do not have that condition, or than subjects who have a different condition.

Embodiments of methods disclosed herein include methods in which a respiratory disease-causing agent is detected if more than a minimum level of such respiratory disease-causing agents is detected in a small-volume sample obtained from a subject. For example, such methods include methods wherein a small-volume sample is tested for the presence of a plurality of respiratory disease-causing agents. In embodiments of such methods, that minimum level may be set at a level that is determined by the condition of the subject. The minimum level may be set at a higher level for subjects who exhibit symptoms of active infection. The minimum level may be set at a lower level for subjects who are receiving treatment for an infection at the time the sample was obtained. The minimum level may be set at a lower level for subjects who have received treatment for an infection prior to the time the sample was obtained, e.g., who have recently received treatment for an infection prior to the time the sample was obtained.

In embodiments, the sample may be diluted prior to testing for the presence of a plurality of disease-causing agents, such as respiratory disease-causing agents. In embodiments, such dilution of a sample is greater for subjects who have a condition which indicates they may have higher levels of disease-causing agents, such as respiratory disease-causing agents, than subject who do not have that condition, or than subjects who have a different condition.

For example, conditions which indicate that a subject may have higher levels of disease-causing agents, such as respiratory disease-causing agents, include subjects with an active infection; subjects who have a cough, including a persistent cough; subjects who have a fever; subjects who report chills; subjects who report fatigue; subjects who report a headache; subjects who have sweats; and subjects who have or report other symptoms indicative of an active infection.

For example, conditions which indicate that a subject may not have higher levels of disease-causing agents, such as respiratory disease-causing agents, include subjects currently receiving treatment for infection; subjects who recently received treatment for infection; subjects currently receiving, or who recently received treatment for, a cough, including a persistent cough; a fever; chills; fatigue; headache; sweats; or other symptoms or indication of an infection.

In embodiments of methods in which a disease-causing agents, such as a respiratory disease-causing agent, is detected if more than a minimum level of such disease-causing agent (e.g., a respiratory disease-causing agent) is detected in a small-volume sample obtained from a subject, wherein the small-volume sample is tested for the presence of a plurality of disease-causing agents, such as respiratory disease-causing agents, the minimum level is set at a higher level for subjects who have not been recently diagnosed with a disease, such as a respiratory disease, than the minimum level set for subjects who have been recently diagnosed with a disease (such as a respiratory disease). In embodiments, the sample may be diluted prior to testing for the presence of said plurality of disease-causing agents, such as respiratory disease-causing agents. In embodiments, such dilution of a sample is greater for subjects who have not been recently diagnosed with a disease, such as a respiratory disease, than the dilution of samples obtained from subjects who have been recently diagnosed with a disease, such as a respiratory disease.

In embodiments, the sample may be further tested for the presence of indicators of inflammation. For example, the sample may be further tested for the presence of higher than normal levels of glucocorticoids such as cortisol (e.g., in the blood, or in saliva, or tears, or other bodily fluid or sample obtained by a swab). For example, the sample may be further tested for the presence of higher than normal levels of histamine (e.g., in the blood, or in saliva, or tears, or other bodily fluid or sample obtained by a swab). Further indicators of inflammation include, without limitation, increased levels of prostaglandins, increased levels of inflammatory cytokines (including, e.g., tumor necrosis factor alpha (TNF-α), interleukin-1 (IL-1), interleukin-8 (IL-8), interleukin-12 (IL-12), interleukin-18 (IL-18), and interferon gamma (IF-γ)), bradykinin, complement system molecules, blood-clotting factors, C-reactive protein, erythrocyte sedimentation rate (ESR), white blood cell count, morphological changes in blood and other cells, and other molecular and cellular markers indicative of inflammation. In addition, a subject may be examined, or asked to self-report, symptoms of inflammation, such as, e.g., swelling, redness, pain, or sensation of heat of an affected area or tissue.

In embodiments, the sample may be further tested for the presence of a cytokine or of a plurality of cytokines. In embodiments, the sample may be further tested for the level of a cytokine or of a plurality of cytokines. In embodiments, the target cytokine is selected from a lymphokine, a chemokine, an interleukin, and an interferon. In embodiments, the target cytokines are selected from lymphokines, chemokines, interleukins, and interferons. In embodiments, the cytokine may be an inflammatory cytokine. In embodiments, the cytokine may be an anti-inflammatory cytokine. In embodiments, a target cytokine may be a an interleukin (IL) selected from IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, and other interleukins. In embodiments, a target cytokine may be a chemokine selected from an a chemokine (also termed a CXC chemokine), a β-chemokine (also termed a CC-chemokine), a γ-chemokine (also termed a C-chemokine), and a d-chemokine (also termed a $CX_3C$-chemokine) In embodiments, a target cytokine may be a member of the tumor necrosis factor (TNF) family.

In embodiments, the same sample may be tested for disease-causing agents and for cytokines. In embodiments, the same sample may be tested for respiratory disease-causing agents and for cytokines In embodiments, the sample may be further tested for the presence of/antibodies to a disease-causing agent. In embodiments, the same sample may be tested for a plurality of disease-causing agents, and for antibodies to a plurality of disease-causing agents.

In embodiments, the sample may be further tested for the presence of antibodies to a respiratory disease-causing agent. In embodiments, the same sample may be tested for a plurality of respiratory disease-causing agents and for antibodies to a plurality of respiratory disease-causing agents.

Methods of detecting the presence of a target flu virus molecule in a sample are disclosed herein, wherein the presence of a plurality of possible target flu viruses are tested from a single sample using both nucleic acid testing and protein testing, wherein nucleic acid testing comprises detection of the presence of target nucleic acid sequences, and wherein protein testing comprises detection of the presence of target proteins having target amino acid sequences. In embodiments, target nucleic acid sequences may comprise sequences having at least 8 nucleotides, or at least 10 nucleotides, or at least 15 nucleotides, or at least 20 nucleotides, or at least 30 nucleotides, or at least 40 nucleotides, or at least 50 nucleotides, or more, that are identical, or closely similar, to target nucleotide sequences. In embodiments, target amino acid sequences may comprise sequences having at least 8 amino acids, or at least 10 amino acids, or at least 15 amino acids, or at least 20 amino acids, or at least 30 amino acids, or at least 40 amino acids, or at least 50 amino acids, or more, that are identical, or closely similar, to target amino acids sequences.

In embodiments, the plurality of possible target flu viruses comprise at least 5 possible target flu viruses, or at least 10 possible target flu viruses, or at least 15 possible target flu viruses, or at least 20 possible target flu viruses, or at least 25 possible target flu viruses, or at least 30 possible target flu viruses, or at least 35 possible target flu viruses, or at least 40 possible target flu viruses, or at least 45 possible target flu viruses, or at least 50 possible target flu viruses, or at least 55 possible target flu viruses, or at least 60 possible target flu viruses, or at least 64 possible target flu viruses, or at least 65 possible target flu viruses, or more.

The assays and methods disclosed herein may be performed on a device, or on a system, for processing a sample. Such a sample may be a small-volume clinical sample. The assays and methods disclosed herein can be readily incorporated into and used in device for processing a sample, or a system for processing a sample, which may be an automated assay device, or may be an automated assay system. Such a device, and such a system, may be useful for the practice of the methods disclosed herein. For example, a device may be useful for receiving a sample. A device may be useful for preparing, or for processing a sample. A device may be useful for performing an assay on a sample. A device may be useful for obtaining data from a sample. A device may be useful for transmitting data obtained from a sample. A device may be useful for disposing of a sample following processing or assaying of a sample.

The assays and methods disclosed herein can be readily incorporated into and used in an automated assay device, and in an automated assay system. For example, systems as disclosed herein may include a communication assembly for transmitting or receiving a protocol based on the analyte to be detected (e.g., a particular disease-causing agent or marker indicative of a particular disease-causing agent) or based on other analytes to be detected by the device or system. In embodiments, an assay protocol may be changed based on optimal scheduling of a plurality of assays to be performed by a device, or may be changed based on results previously obtained from a sample from a subject, or based on results previously obtained from a different sample from the subject. In embodiments, a communication assembly may comprise a channel for communicating information from said device to a computer, said wherein said channel is selected from a computer network, a telephone network, a metal communication link, an optical communication link, and a wireless communication link. In embodiments, systems as disclosed herein may transmit signals to a central location, or to an end user, and may include a communication assembly for transmitting such signals. Systems as disclosed herein may be configured for updating a protocol as needed or on a regular basis.

A device may be part of a system, a component of which may be a sample processing device. A device may be a sample processing device. A sample processing device may be configured to facilitate collection of a sample, prepare a sample for a clinical test, or effect a chemical reaction with one or more reagents or other chemical or physical processing, as disclosed herein. A sample processing device may be configured to obtain data from a sample. A sample processing device may be configured to transmit data obtained from a sample. A sample processing device may be configured to analyze data from a sample. A sample processing device may be configured to communicate with another device, or a laboratory, or an individual affiliated with a laboratory, to analyze data obtained from a sample.

A sample processing device may be configured to be placed in or on a subject. A sample processing device may be configured to accept a sample from a subject, either directly or indirectly. A sample may be, for example, a blood sample (e.g., a sample obtained from a fingerstick, or from venipuncture, or an arterial blood sample), a urine sample, a biopsy sample, a tissue slice, stool sample, or other clinical sample; a water sample, a soil sample, a food sample, an air sample; or other sample. A blood sample may comprise, e.g., whole blood, plasma, or serum. A sample processing device may receive a sample from the subject through a housing of the device. The sample collection may occur at a sample collection site, or elsewhere. The sample may be provided to the device at a sample collection site.

In some embodiments, a sample processing device may be configured to accept or hold a cartridge. In some embodiments, a sample processing device may comprise a cartridge. The cartridge may be removable from the sample processing device. In some embodiments, a sample may be provided to the cartridge of the sample processing device. Alternatively, a sample may be provided to another portion of a sample processing device. The cartridge and/or device may comprise a sample collection unit that may be configured to accept a sample.

A cartridge may include a sample, and may include reagents for use in processing or testing a sample, disposables for use in processing or testing a sample, or other materials. Following placement of a cartridge on, or insertion of a cartridge into, a sample processing device, one or more components of the cartridge may be brought into fluid communication with other components of the sample processing device. For example, if a sample is collected at a cartridge, the sample may be transferred to other portions of the sample processing device. Similarly, if one or more reagents are provided on a cartridge, the reagents may be transferred to other portions of the sample processing device, or other components of the sample processing device may be brought to the reagents. In some embodiments, the reagents or components of a cartridge may remain on-board the cartridge. In some embodiments, no fluidics are included that require tubing or that require maintenance (e.g., manual or automated maintenance).

A sample or reagent may be transferred to a device, such as a sample processing device. A sample or reagent may be transferred within a device. Such transfer of sample or reagent may be accomplished without providing a continuous fluid pathway from cartridge to device. Such transfer of sample or reagent may be accomplished without providing a continuous fluid pathway within a device. In embodiments, such transfer of sample or reagent may be accomplished by a sample handling system (e.g., a pipette); for example, a sample, reagent, or aliquot thereof may be aspirated into an open-tipped transfer component, such as a pipette tip, which may be operably connected to a sample handling system which transfers the tip, with the sample, reagent, or aliquot thereof contained within the tip, to a location on or within the sample processing device. The sample, reagent, or aliquot thereof can be deposited at a location on or within the sample processing device. Sample and reagent, or multiple reagents, may be mixed using a sample handling system in a similar manner. One or more components of the cartridge may be transferred in an automated fashion to other portions of the sample processing device, and vice versa.

A device, such as a sample processing device, may have a fluid handling system. A fluid handling system may perform, or may aid in performing, transport, dilution, extraction, aliquotting, mixing, and other actions with a fluid, such as a sample. In some embodiments, a fluid handling system may be contained within a device housing. A fluid handling system may permit the collection, delivery, processing and/or transport of a fluid, dissolution of dry reagents, mixing of liquid and/or dry reagents with a liquid, as well as collection, delivery, processing and/or transport of non-fluidic components, samples, or materials. The fluid may be a sample, a reagent, diluent, wash, dye, or any other fluid that may be used by the device, and may include, but not limited to, homogenous fluids, different liquids, emulsions, suspensions, and other fluids. A fluid handling system, including without limitation a pipette, may also be used to transport vessels (with or without fluid contained therein) around the device. The fluid handling system may dispense or aspirate a fluid. The sample may include one or more particulate or solid matter floating within a fluid.

In embodiments, a fluid handling system may comprise a pipette, pipette tip, syringe, capillary, or other component. The fluid handling system may have portion with an interior surface and an exterior surface and an open end. The fluid handling system may comprise a pipette, which may include a pipette body and a pipette nozzle, and may comprise a pipette tip. A pipette tip may or may not be removable from a pipette nozzle. In embodiments, a fluid handling system may use a pipette mated with a pipette tip; a pipette tip may be disposable. A tip may form a fluid-tight seal when mated with a pipette. A pipette tip may be used once, twice, or more times. In embodiments, a fluid handling system may use a pipette or similar device, with or without a pipette tip, to aspirate, dispense, mix, transport, or otherwise handle the fluid. The fluid may be dispensed from the fluid handling system when desired. The fluid may be contained within a pipette tip prior to being dispensed, e.g., from an orifice in the pipette tip. In embodiments, or instances during use, all of the fluid may be dispensed; in other embodiments, or instances during use, a portion of the fluid within a tip may be dispensed. A pipette may selectively aspirate a fluid. The pipette may aspirate a selected amount of fluid. The pipette may be capable of actuating stirring mechanisms to mix the fluid within the tip or within a vessel. The pipette may incorporate tips or vessels creating continuous flow loops for mixing, including of materials or reagents that are non-liquid form. A pipette tip may also facilitate mixture by metered delivery of multiple fluids simultaneously or in sequence, such as in 2-part substrate reactions.

The fluid handling system may include one or more fluidically isolated or hydraulically independent units. For example, the fluid handling system may include one, two, or more pipette tips. The pipette tips may be configured to accept and confine a fluid. The tips may be fluidically isolated from or hydraulically independent of one another. The fluid contained within each tip may be fluidically isolated or hydraulically independent from one fluids in other tips and from other fluids within the device. The fluidically isolated or hydraulically independent units may be movable relative to other portions of the device and/or one another. The fluidically isolated or hydraulically independent units may be individually movable. A fluid handling system may comprise one or more base or support. A base or support may support one or more pipette or pipette units. A base or support may connect one or more pipettes of the fluid handling system to one another.

A sample processing device may be configured to perform processing steps or actions on a sample obtained from a subject. Sample processing may include sample preparation, including, e.g., sample dilution, division of a sample into aliquots, extraction, contact with a reagent, filtration, separation, centrifugation, or other preparatory or processing action or step. A sample processing device may be configured to perform one or more sample preparation action or step on the sample. Optionally, a sample may be prepared for a chemical reaction and/or physical processing step. A sample preparation action or step may include one or more of the following: centrifugation, separation, filtration, dilution, enriching, purification, precipitation, incubation, pipetting, transport, chromatography, cell lysis, cytometry, pulverization, grinding, activation, ultrasonication, micro column processing, processing with magnetic beads, processing with nanoparticles, or other sample preparation action or steps. For example, sample preparation may include one or more step to separate blood into serum and/or particulate fractions, or to separate any other sample into various components. Sample preparation may include one or more step to dilute and/or concentrate a sample, such as a blood sample, or other clinical samples. Sample preparation may include adding an anti-coagulant or other ingredient to a sample. Sample preparation may also include purification of a sample. In embodiments, all sample processing, preparation, or assay actions or steps are performed by a single device. In embodiments, all sample processing, preparation, or assay actions or steps are performed within a housing of a single device. In embodiments, most sample processing, preparation, or assay actions or steps are performed by a single device, and may be performed within a housing of a single device. In embodiments, many sample processing, preparation, or assay actions or steps are performed by a single device, and may be performed within a housing of a single device. In embodiments, sample processing, preparation, or assay actions or steps may be performed by more than one device.

A sample processing device may be configured to run one or more assay on a sample, and to obtain data from the sample. An assay may include one or more physical or chemical treatments, and may include running one or more chemical or physical reactions. A sample processing device may be configured to perform one, two or more assays on a small sample of bodily fluid. One or more chemical reaction may take place on a sample having a volume, as described elsewhere herein. For example one or more chemical reaction may take place in a pill having less than femtoliter volumes. In an instance, the sample collection unit is configured to receive a volume of the bodily fluid sample equivalent to a single drop or less of blood or interstitial fluid. In embodiments, the volume of a sample may be a small volume, where a small volume may be a volume that is less than about 1000 µL, or less than about 500 µL, or less than about 250 µL, or less than about 150 µL, or less than about 100 µL, or less than about 75 µL, or less than about 50 µL, or less than about 40 µL, or less than about 20 µL, or less than about 10 µL, or other small volume. In embodiments, all sample assay actions or steps are performed on a single sample. In embodiments, all sample assay actions or steps are performed by a single device. In embodiments, all sample assay actions or steps are performed within a housing of a single device. In embodiments, most sample assay actions or steps are performed by a single device, and may be performed within a housing of a single device. In embodiments, many sample assay actions or steps are performed by a single device, and may be performed within a housing of a single device. In embodiments, sample processing, preparation, or assay actions or steps may be performed by more than one device.

A sample processing device may be configured to perform a plurality of assays on a sample. In embodiments, a sample processing device may be configured to perform a plurality of assays on a single sample. In embodiments, a sample processing device may be configured to perform a plurality of assays on a single sample, where the sample is a small sample. For example, a small sample may have a sample volume that is a small volume of less than about 1000 µL, or less than about 500 µL, or less than about 250 µL, or less than about 150 µL, or less than about 100 µL, or less than about 75 µL, or less than about 50 µL, or less than about 40 µL, or less than about 20 µL, or less than about 10 µL, or other small volume. A sample processing device may be capable of performing multiplexed assays on a single sample. A plurality of assays may be run simultaneously; may be run sequentially; or some assays may be run simultaneously while others are run sequentially. One or more control assays and/or calibrators (e.g., including a configuration with a control of a calibrator for the assay/tests) can also be incorporated into the device; control assays and assay on calibrators may be performed simultaneously with assays performed on a sample, or may be performed before or after assays performed on a sample, or any combination thereof. In embodiments, all sample assay actions or steps are performed by a single device. In embodiments, all of a plurality of assay actions or steps are performed within a housing of a single device. In embodiments, most sample assay actions or steps, of a plurality of assays, are performed by a single device, and may be performed within a housing of a single device. In embodiments, many sample assay actions or steps, of a plurality of assays, are performed by a single device, and may be performed within a housing of a single device. In embodiments, sample processing, preparation, or assay actions or steps may be performed by more than one device.

In embodiments, all of a plurality of assays may be performed in a short time period. In embodiments, such a short time period comprises less than about three hours, or less than about two hours, or less than about one hour, or less than about 40 minutes, or less than about 30 minutes, or less than about 25 minutes, or less than about 20 minutes, or less than about 15 minutes, or less than about 10 minutes, or less than about 5 minutes, or less than about 4 minutes, or less than about 3 minutes, or less than about 2 minutes, or less than about 1 minute, or other short time period.

A sample processing device may be configured to detect one or more signals relating to the sample. A sample processing device may be configured to identify one or more properties of the sample. For instance, the sample processing device may be configured to detect the presence or concentration of one analyte or a plurality of analytes or a disease condition in the sample (e.g., in or through a bodily fluid, secretion, tissue, or other sample). Alternatively, the sample processing device may be configured to detect a signal or signals that may be analyzed to detect the presence or concentration of one or more analytes (which may be indicative of a disease condition) or a disease condition in the sample. The signals may be analyzed on board the device, or at another location. Running a clinical test may or may not include any analysis or comparison of data collected.

A chemical reaction or other processing step may be performed, with or without the sample. Examples of steps, tests, or assays that may be prepared or run by the device may include, but are not limited to immunoassay, nucleic acid assay, receptor-based assay, cytometric assay, colorimetric assay, enzymatic assay, electrophoretic assay, electrochemical assay, spectroscopic assay, chromatographic assay, microscopic assay, topographic assay, calorimetric assay, turbidmetric assay, agglutination assay, radioisotope assay, viscometric assay, coagulation assay, clotting time assay, protein synthesis assay, histological assay, culture assay, osmolarity assay, and/or other types of assays, centrifugation, separation, filtration, dilution, enriching, purification, precipitation, pulverization, incubation, pipetting, transport, cell lysis, or other sample preparation action or steps, or combinations thereof. Steps, tests, or assays that may be prepared or run by the device may include imaging, including microscopy, cytometry, and other techniques preparing or utilizing images. Steps, tests, or assays that may be prepared or run by the device may further include an assessment of histology, morphology, kinematics, dynamics, and/or state of a sample, which may include such assessment for cells.

A device may be capable of performing all on-board steps (e.g., steps or actions performed by a single device) in a short amount of time. A device may be capable of performing all on-board steps on a single sample in a short amount of time. For example, from sample collection from a subject to transmitting data and/or to analysis may take about 3 hours or less, 2 hours or less, 1 hour or less, 50 minutes or less, 45 minutes or less, 40 minutes or less, 30 minutes or less, 20 minutes or less, 15 minutes or less, 10 minutes or less, 5 minutes or less, 4 minutes or less, 3 minutes or less, 2 minutes or less, or 1 minute or less. The amount of time from accepting a sample within the device to transmitting data and/or to analysis from the device regarding such a sample may depend on the type or number of steps, tests, or assays performed on the sample. The amount of time from accepting a sample within the device to transmitting data and/or to analysis from the device regarding such a sample may take about 3 hours or less, 2 hours or less, 1 hour or less, 50 minutes or less, 45 minutes or less, 40 minutes or less, 30 minutes or less, 20 minutes or less, 15 minutes or less, 10 minutes or less, 5 minutes or less, 4 minutes or less, 3 minutes or less, 2 minutes or less, or 1 minute or less.

A device may be configured to prepare a sample for disposal, or to dispose of a sample, such as a clinical sample, following processing or assaying of a sample.

In embodiments, a sample processing device may be configured to transmit data obtained from a sample. In embodiments, a sample processing device may be configured to communicate over a network. A sample processing device may include a communication module that may interface with the network. A sample processing device may be connected to the network via a wired connection or wirelessly. The network may be a local area network (LAN) or a wide area network (WAN) such as the Internet. In some embodiments, the network may be a personal area network. The network may include the cloud. The sample processing device may be connected to the network without requiring an intermediary device, or an intermediary device may be required to connect a sample processing device to a network. A sample processing device may communicate over a network with another device, which may be any type of networked device, including but not limited to a personal computer, server computer, or laptop computer; personal digital assistants (PDAs) such as a Windows CE device; phones such as cellular phones, smartphones (e.g., iPhone, Android, Blackberry, etc.), or location-aware portable phones (such as GPS); a roaming device, such as a network-connected roaming device; a wireless device such as a wireless email device or other device capable of communicating wireless with a computer network; or any other type of network device that may communicate possibly over a network and handle electronic transactions. Such communication may include providing data to a cloud computing infrastructure or any other type of data storage infrastructure which may be accessed by other devices.

A sample processing device may provide data regarding a sample to, e.g., a health care professional, a health care professional location, such as a laboratory, or an affiliate thereof. One or more of a laboratory, health care professional, or subject may have a network device able to receive or access data provided by the sample processing device. A sample processing device may be configured to provide data regarding a sample to a database. A sample processing device may be configured to provide data regarding a sample to an electronic medical records system, to a laboratory information system, to a laboratory automation system, or other system or software. A sample processing device may provide data in the form of a report.

A laboratory, device, or other entity or software may perform analysis on data regarding a sample in real-time. A software system may perform chemical analysis and/or pathological analysis, or these could be distributed amongst combinations of lab, clinical, and specialty or expert personnel. Analysis may include qualitative and/or quantitative evaluation of a sample. Data analysis may include a subsequent qualitative and/or quantitative evaluation of a sample. Optionally, a report may be generated based on raw data, pre-processed data, or analyzed data. Such a report may be prepared so as to maintain confidentiality of the data obtained from the sample, the identity and other information regarding the subject from whom a sample was obtained, analysis of the data, and other confidential information. The report and/or the data may be transmitted to a health care professional. Data obtained by a sample processing device, or analysis of such data, or reports, may be provided to a database, an electronic medical records system, to a laboratory information system, to a laboratory automation system, or other system or software.

Nucleic Acid Detection

Markers indicative of a disease, such as a respiratory disease, include nucleic acid markers. Such nucleic acid markers include, for example, viral nucleic acids, or portions thereof; bacterial nucleic acids, or portions thereof; and nucleic acids, or portions thereof, derived from other microorganisms. Methods for detecting nucleic acid markers in a sample, including in a small volume sample, include methods in which small amounts of nucleic acid may be amplified (e.g., copies made). For example, polymerase chain reaction (PCR) and related methods are common methods of nucleic acid amplification. PCR is discussed, for example, in in U.S. Pat. No. 4,683,195; and generally in Mullis et al., Cold Spring Harbor Symposium on Quantitative Biology, volume 51:263 (1987); Erlich, ed., PCR Technology (Stockton Press, N.Y., 1989). PCR is one, but not the only, example of a nucleic acid polymerase reaction method for amplifying a nucleic acid test sample comprising the use of a known nucleic acid as a primer and a nucleic acid polymerase to amplify or generate a specific piece of nucleic acid. Further discussion of PCR and other methods may be found, for example, in *Molecular Cloning A Laboratory Manual* by Green and Sambrook, Cold Spring Harbor Laboratory Press, 4$^{th}$ Edition 2012, which is incorporated by reference herein in its entirety. PCR and many other amplification methods must be performed at multiple different temperatures, requiring repeated temperature changes during the PCR reaction ("thermal cycling"). Other amplification methods, such as, e.g., loop-mediated isothermal amplification ("LAMP") (see, e.g. U.S. Pat. No. 6,410,278), and other methods, including methods discussed below, require less or less extensive thermal cycling than does PCR, or require no thermal cycling.

Nucleic Acid Amplification and Detection Methods without Thermal Cycling

Methods for nucleic acid amplification which do not require thermal cycling are described in U.S. Patent Application 61/800,606, filed Mar. 15, 2013, incorporated by reference herein in its entirety. Such methods may be used to detect nucleic acid markers of disease, such as respiratory disease, in small-volume samples in short periods of time. Such methods are discussed below, and examples of results obtained with such methods, from small samples and in short periods of time, are presented in the Figures and Examples disclosed herein. In the following, such methods are termed "non-cycling amplification methods."

Non-cycling amplification methods of nucleic acid amplification may be applied to double-stranded DNA. However, target nucleic acid molecules need not be limited to double-stranded DNA targets; for example, double-stranded DNA for use in non-cycling amplification methods described herein may be prepared from viral RNA, or mRNA, or other single stranded RNA target sources, by reverse transcriptase. In further example, double-stranded DNA for use in non-cycling amplification methods described herein may be prepared from single-stranded DNA targets by DNA polymerase. Such methods may be applied as an initial step, prior to application of the non-cycling amplification methods discussed below.

Amplification of a double-stranded DNA target, for example, begins with a primary double-stranded DNA to be amplified (termed the "primary nucleic acid" in the following). The primary nucleic acid contains a target region termed a template region; the template region has a template sequence. Such a double-stranded template region contains a first DNA strand and a complementary second DNA strand, and includes a 5' terminal nucleotide in one strand and a 3' terminal nucleotide in the other strand that are complementary to each other.

A first primer and a second primer are provided which each have template-binding regions and tail regions; the primer template-binding regions are complementary to the target template regions. The tail regions of the primers may contain three components: a) the 5' terminal nucleotide of the primer, b) an innermost nucleotide, wherein the innermost nucleotide is downstream from the 5' terminal nucleotide, and c) a middle section between the 5' terminal nucleotide and the innermost nucleotide, comprising one or more nucleotides. In addition, at least portions of the two primer tail regions may be complementary to each other when properly aligned.

It should be noted that although the tail region of the second primer may contain a nucleotide sequence which is complementary to the nucleotide sequence of the tail region of the first primer, typically, products formed by the annealing of the first primer and second primer are not desirable or useful for methods or compositions provided herein. Accordingly, in some embodiments, steps may be taken to minimize the formation of first primer—second primer annealed products. Such steps may include, for example, not pre-incubating a first primer and a second primer under conditions where the primers may anneal for an extended period of time before initiating a method provided herein.

The primary nucleic acid may be treated with a polymerase and a first copy of the first primer under conditions such that the template-binding region of the first copy of the first primer anneals to the first strand of the nucleic acid template. Under these conditions, an extension product of the first copy of the first primer is formed. The polymerase, which may have strand displacement activity, may catalyze the formation of the extension product of the first copy of the first primer. The first copy of the first primer may be covalently linked to the synthesized extension product, such that the first copy of the first primer (which is complementary to the first strand of the nucleic acid template) becomes part of the molecule described herein as the "extension product of the first copy of the first primer." The template-binding region but not the tail region of the first copy of the first primer anneals to the first strand of the nucleic acid template. Examples of conditions suitable for polymerase-based nucleic acid synthesis are known in the art and are provided, for example, in *Molecular Cloning: A Laboratory Manual*, M. R. Green and J. Sambrook, Cold Spring Harbor Laboratory Press (2012), which is incorporated by reference herein in its entirety.

The extension product of the first copy of the first primer may be treated with a polymerase (which may have strand displacement activity) and with the second primer under conditions such that the template-binding region of the second primer anneals to the extension product of the first copy of the first primer. In this way, an extension product of the second primer may be formed. The polymerase may displace the first strand of the nucleic acid template from the extension product of the first copy of the first primer during the synthesis of the extension product of the second primer. The second primer may be covalently linked to the synthesized extension product, such that the second primer becomes part of the molecule described herein as the "extension product of the second primer." The extension product of the second primer is complementary to the extension product of the first copy of the first primer. The template-binding region but not the tail region of the second primer may anneal to the extension product of the first copy of the first primer when the second primer anneals to the extension product of the first copy of the first primer.

The extension product of the second primer may be treated with a polymerase (which may have strand displacement activity) and a second copy of the first primer so as to form an extension product of the second copy of the first primer. During the generation of the extension product of the second copy of the first primer, the second copy of the first primer may be covalently linked to the synthesized extension product, such that the second copy of the first primer becomes part of the molecule described herein as the "extension product of the second copy of the first primer." The extension product of the second copy of the first primer is complementary to the extension product of the second primer.

Generation of the extension product of the second copy of the first primer may result in the generation of a molecule comprising the extension product of the second copy of the first primer and the extension product of the second primer, which may be referred to herein as the "secondary nucleic acid." A secondary nucleic acid may comprise the 3' terminal region of the extension product of the second primer (and the complement thereof) and may comprise the 3' terminal region of the extension product of the second copy of the first primer (and the complement thereof). Secondary nucleic acid molecules include sequences of the template region adjacent to tail sequences. In embodiments, double-stranded nucleic acids are produced in which complementary template and tail region sequences line up. In practice, multiple copies (e.g., two or more) of the secondary nucleic acid are produced by any process whereby a nucleic acid having the general structure of the secondary nucleic acid may be generated, including by practice of non-cycling amplification methods discussed herein.

Thus, pairs of copies of the secondary nucleic acid may be provided. Further numbers of copies may then be generated, for example, by repetition of the foregoing steps and methods. For example, the full process as described above for generating a secondary nucleic acid from a primary nucleic acid may be repeated two times, in order to generate a two pairs of copies of the secondary nucleic acid; further repetitions may be performed to amplify the number of copies further, e.g., to exponentially amplify the number of copies (e.g., by powers of two).

In addition, since the secondary nucleic acid molecules include sequences of the template region adjacent to tail sequences, partially double-stranded nucleic acids may be produced in which tail region sequences hybridize and line up. Since these tail region sequences are attached to single-stranded template regions, a cross-over structure having two nucleic acid strands together held by the hybridized tail region sequences is produced. These cross-over structures may be extended by a polymerase to form extension products of both component strands. These extension products which may be referred to as "concatemer strands." Two concatemer strands may be annealed together, and may be collectively referred to as a concatemer; such concatemers may contain two or more copies of the nucleic acid template.

In some embodiments, even longer concatemers may be formed. For example, concatemers may anneal together; or two concatemer molecules may form a cross-over structure similar to those formed by the shorter molecules termed concatemer strands, as discussed above, followed by a larger concatemer molecule containing four copies of the nucleic acid template. In another example, a secondary nucleic acid and a concatemer may form a cross-over structure, followed by a larger concatemer molecule containing three copies of the nucleic acid template. In some embodiments, multiple different concatemers of multiple different lengths may be simultaneously generated.

Thus, concatemers generated according to such methods may be of any length of nucleotides. In some embodiments, concatemer molecules generated herein may be at least 30, 40, 50, 60, 70, 80, 90, 100, 150, 200, 250, 300, 400, 500, 600, 700, 800, 900, 1000, 1500, 2000, 3000, 4000, 5000, 6000, 7000, 8000, 9000, 10,000, 15,000, 20,000, or 25,000 nucleotides in length. Concatemers generated according to such methods may contain any number of copies of a nucleic acid template. In some embodiments, concatemer molecules generated herein may contain at least 2, 3, 4, 5, 6, 7, 8, 9, 10, 11, 12, 13, 14, 15, 16, 17, 18, 19, 20, 25, 30, 35, 40, 45, 50, 60, 70, 80, 90, or 100 copies of a nucleic acid template. Further examples are provided, and greater detail of these and other examples, is provided in U.S. Patent Application 61/800,606, filed Mar. 15, 2013.

Detection of Reactions

Progress of a method provided herein may be monitored in multiple different ways. In one embodiment, a reaction may be assayed for a nucleic acid amplification product (e.g. for the level of the product or the rate of its generation). In another embodiment, a reaction may be assayed for the activity of a polymerase along a nucleic acid template (e.g. for movement of a polymerase along a template strand). Thus, in some embodiments, events of a method provided herein may observed due to the accumulation of product from a method (which may be during or after completion of steps of the method), or due to detectable events occurring during the steps of a method.

The presence of amplified nucleic acids can be assayed, for example, by detection of reaction products (amplified nucleic acids or reaction by-products) or by detection of probes associated with the reaction progress.

In some embodiments, reaction products may be identified by staining the products with a dye. In some embodiments, a dye may have greater fluorescence when bound to a nucleic acid than when not bound to a nucleic acid. In some embodiments, a dye may intercalate with a double-stranded nucleic acid or it may bind to an external region of a nucleic acid. Nucleic acid dyes that may be used with methods and compositions provided herein include, for example, cyanine dyes, PicoGreen®, OliGreen®, RiboGreen®, SYBR® dyes, SYBR® Gold, SYBR® Green I, SYBR® Green II, ethidium bromide, dihydroethidium, BlueView™, TOTO® dyes, TO-PRO® dyes, POPO® dyes, YOYO® dyes, BOBO® dyes, JOJO® dyes, LOLO® dyes, SYTOX® dyes, SYTO® dyes, propidium iodide, hexidium iodide, methylene blue, DAPI, acridine orange, quinacrine, acridine dimers, 9-amino-6-chloro-2-methoxyacridine, bis-benzimide dyes, Hoechst dyes, 7-aminoactinomycin D, actinomycin D, hydroxystilbamidine, pyronin Y, Diamond™ dye, GelRed™, GelGreen™ and LDS 751.

In some embodiments, reaction products may be identified by analysis of turbidity of amplification reactions for example, where increased turbidity is correlated with formation of reaction products and reaction by-products (e.g. pyrophosphate complexed with magnesium).

In some embodiments, reaction products may be identified by separating a reaction performed according to a method herein by gel electrophoresis, followed by staining of the gel with a dye for nucleic acids. The dye may be any nucleic acid dye disclosed herein or otherwise known in the art.

In some embodiments, any method or composition known in the art for the detection of nucleic acids or processes associated with the generation of nucleic acids may be used with methods and compositions provided herein.

In some embodiments, a nucleic acid probe which contains a nucleotide sequence complementary to a portion of a nucleic acid template strand (or strand having a similar or identical sequence) and which contains one or both of a fluorescent reporter (fluorophore) and a quencher are included in a reaction provided herein.

In an example, a nucleic acid probe may contain a fluorescent reporter at its 5' or 3' terminus, and a quencher at the other terminus.

In another example, a nucleic acid probe may contain a fluorescent reporter at its 5' or 3' terminus, and it may be annealed to a nucleic acid primer containing a quencher. The nucleic acid primer containing a quencher may contain the quencher at a position in the primer such that when the nucleic acid probe is annealed to the primer, the fluorescent reporter is quenched.

In probes containing a fluorescent reporter and quencher pair, the fluorescent reporter and quencher may be selected so that the quencher can effectively quench the reporter. In some embodiments, a fluorescent reporter is paired with a quencher where the emission maximum of the fluorescent reporter is similar to the absorption maximum of the quencher. Fluorphores that may be used as the fluorescent reporter include, for example, CAL Fluor Gold, CAL Fluor Orange, Quasar 570, CAL Fluor Red 590, CAL Fluor Red 610, CAL Fluor Red 610, CAL Fluor Red 635, Quasar 670 (Biosearch Technologies), VIC, NED (Life Technologies), Cy3, Cy5, Cy5.5 (GE Healthcare Life Sciences), Oyster 556, Oyster 645 (Integrated DNA Technologies), LC red 610, LC red 610, LC red 640, LC red 670, LC red 705 (Roche Applies Science), Texas red, FAM, TET, HEX, JOE, TMR, and ROX. Quenchers that may be used include, for example, DDQ-I, DDQ-II (Eurogentec), Eclipse (Epoch Biosciences), Iowa Black FQ, Iowa Black RQ (Integrated DNA Technologies), BHQ-1, BHQ-2, BHQ-3 (Biosearch Technologies), QSY-7, QSY-21 (Molecular Probes), and Dabcyl.

In some embodiments, a method provided herein may be monitored in an apparatus containing a light source and an optical sensor. In some situations, the reaction may be positioned in the path of light from the light source, and light absorbed by the sample (e.g. in the case of a turbid reaction), scattered by the sample (e.g. in the case of a turbid reaction), or emitted by the sample (e.g. in the case of a reaction containing a fluorescent molecule) may be measured. In some embodiments, a method provided herein may be performed or monitored in a device or module therein as disclosed in U.S. patent application Ser. No. 13/769,779, filed Feb. 18, 2013, which is herein incorporated by reference in its entirety.

Detection of Nucleic Acids and Protein Markers of Infection

A sample, such as a throat swab, a nasal swab, a mouth swab (e.g., a cheek swab), a vaginal swab, saliva, blood, or other sample, may be used for more than one assay. For example, a sample may be subjected to nucleic acid testing and to testing for peptides indicative of an infection. In embodiments, a sample may be divided into two or more portions, and each portion may be subjected to a single test, or may be subjected to a plurality of tests. Nucleic acid testing may be used to identify nucleic acid molecules, or portions thereof, whose presence indicates the presence of disease-causing organisms (e.g., viruses, bacteria, and other organisms which carry such nucleic acids). Protein (or peptide) testing may be used to identify peptides or proteins, or portions thereof, whose presence indicates the presence of disease-causing organisms (e.g., organisms which express such proteins, or peptides). Protein or peptide testing may be used to identify disease-causing organisms (e.g., viruses, bacteria, and other organisms) in a sample, and may also be used to identify antibodies directed against such agents that may be present in a sample. Thus, forms of protein (or peptide) testing include testing for the presence of antibodies to targets whose presence indicates the presence of disease-causing organisms. Such nucleic acid and protein (or peptide) testing may be used to identify, or estimate, or otherwise determine at what stage an infection in a subject is at the time the sample was taken, by detecting, or determining the amounts of, or both, both nucleic acid markers indicative of a particular infection and protein (or peptide) markers indicative of the same infection (such protein markers of the same infection include antibodies to the micro-organism that causes the infection, as well as protein markers present on or in the micro-organism itself).

Nucleic acid markers of an infection include DNA and RNA molecules, and fragments thereof, unique to the infectious agent (e.g., viral nucleic acids, or bacterial nucleic acids, or other nucleic acids of any other infectious micro-organism). Peptide or protein markers of an infection include peptides or proteins unique to the infectious agent (e.g., bacterial peptides); cytokines and other peptides produced in response to the infection; and antibodies produced in response to the infection.

For example, where nucleic acid markers indicative of a particular infection are relatively numerous, while antibody markers indicative of that particular infection are relatively sparse, then the infection is a recent infection; however, where nucleic acid markers indicative of a particular infection are relatively numerous, and antibody markers indicative of that particular infection are also relatively numerous, then the infection is not a recent infection, since the subject has had the time to produce infection-specific antibodies. Where nucleic acid markers indicative of a particular infection are relatively sparse, and antibody markers indicative of that particular infection are relatively numerous, then the infection may be waning and in a late stage. Other protein markers (other than antibodies to the infectious organism), being produced by the disease-causing organism itself, such as viral coat proteins, bacterial cell wall proteins, bacterial toxins, and other non-antibody markers, typically follow a time-course more similar to that of nucleic acid markers of a particular infection and less similar to that of antibody markers of a particular infection.

A typical response in human subjects to infection by many infectious agents includes increased levels of inflammatory cytokines (including interleukin 1 (IL-1), IL-6, IL-18, tumor necrosis factor α (TNF-α), gamma interferon (IFN-γ), and others). Cytokine levels may increase rapidly upon infection.

The time-course of production of antibodies to an infectious agent (e.g., a virus, bacteria, or other infectious microorganism) varies between individual subjects and from infection to infection; such time-courses may be known or identified for different kinds of infections. In general, a few days or more are required before antibodies to an infectious agent are detectable in a subject; once detectable, the amount of antibodies detected in a subject grows, often very rapidly, and may plateau (or peak) over a period of weeks or months following infection. In addition to the type of infection, factors which may affect the plateau (or peak) levels, and the timing at which these levels are reached, include whether or not the infection is acute or chronic; the severity of the infection; other diseases or conditions affecting the subject; the nutritional status of the subject; environmental factors; and other factors.

The time-course of an acute infection may be short; for example, an acute infection may follow a time-course measured in days or weeks. For example, many viral and bacterial infections in an otherwise healthy human subject typically resolve within about a week. Levels of nucleic acid and protein markers indicative of viral, bacterial, and other infections typically rise, and then fall, during the course of the infection. Initially, upon infection, and closely following the time of infection, markers of the infectious agent (e.g., nucleic acid markers and protein markers indicative of the viral, bacterial, or other infection) will be detectable in samples obtained from a subject; the levels of such markers will rise from the time of infection, and will typically peak within a few days (for a short-lived infection) or within a few weeks (for an infection of longer duration). Antibodies to the infectious agent may be detected within a week or two following the infection, and may then further increase for several weeks (e.g., for a month or more). If the infection itself resolves and the infectious agent is cleared from the subject, the levels of antibodies will then slowly decline over a period of months.

Longer term, or chronic infections may follow a longer time-course. For example, the time-course of viral markers and antibody formation in a person infected with the human immunodeficiency virus (HIV) may follow a time-course over many months and years. Initially, HIV viral markers (e.g., the viral p24 antigen, viral nucleic acids, and other viral markers produced by the virus itself) may be present (in samples obtained from a subject) in high levels for the first few months following infection, and may peak by about 6 months after infection. In contrast, anti HIV antibodies (e.g., antibodies to gp120 or other viral antigenic epitopes) are not detectable in samples obtained from a subject for a few months following infection, but become detectable by about 3-5 months after infection, and anti-HIV antibody levels rise rapidly over the following 6 months or so, continuing to rise at a less rapid rate from about 1 year after infection to about 4 to 6 years following infection. Over this period of time (from about 1 year to about 5 years) the viral marker levels may be very low; however, in the absence of treatment, as T-cell levels (e.g., CD4 T-cells) will typically have been falling over the period of time from about 1 year to about 5 years following HIV infection, the subject may begin to suffer from systemic immune deficiency and further T-cell loss (e.g., CD-8 T-cells) about 5-6 years following HIV infection. Levels of HIV viral markers will typically rise as systemic immune deficiency becomes apparent 5-6 years following HIV infection.

The time-courses relevant to the detection of marker may also depend on the type of sample tested for the presence of the marker. For example, in some infections, the causative organism, and nucleic acid and protein markers of the organism, may be found initially in blood, or saliva, or other fluid or tissue; and may later on be found in urine or stool samples; and even later on may be detectable in tissue samples. Antibodies to such disease-causing organisms, which typically appear some time following the appearance of the organism itself in samples, may found first in blood, and then, following their appearance in blood, in saliva, urine, or stool.

Devices

The devices, systems, and assays disclosed herein may utilize techniques, devices, systems, and assays disclosed, for example, in U.S. Pat. Nos. 8,088,593; 8,380,541; U.S. patent application Ser. No. 13/769,798, filed Feb. 18, 2013; U.S. patent application Ser. No. 13/769,779, filed Feb. 18, 2013; U.S. Application Ser. No. 61/800,606, filed Mar. 15, 2013; U.S. Application Ser. No. 61/766,095, filed Feb. 18, 2013; and U.S. Patent Application 61/805,923, filed Mar. 27, 2013, all of which are incorporated by reference herein (supra).

For example, devices for use in performing assays for detecting a plurality of disease-causing agents in a single clinical sample, or in a plurality of aliquots of a single clinical sample include cartridges including some or all of reagent vessels, reaction vessels, tools and implements used in assays, and reagents used in assays. A cartridge may contain one or more of: reagent vessels; reaction vessels; cytometry cuvettes; waste containers; sample collection devices or sample collection vessels; and other vessels and materials. Such devices may include multiple vessels containing reagents for use in an assay for the detection of a plurality of markers indicative of an infectious agent, e.g., an upper respiratory infectious agent; a lower respiratory infectious agent; a sexually transmitted disease-causing agent; an agent detectable from a sample obtained from a swab (e.g., a throat swab, a nasal swab, a mouth swab (e.g., a cheek swab), a vaginal swab, or other swab); an agent detectable from a blood sample; or combinations thereof Thus, for example, a cartridge may contain a plurality of reagent vessels; a plurality of reagent vessels containing reagents for detecting a marker indicative of a disease-causing agent. Disease-causing agents may include agents which cause upper respiratory disorders, or lower respiratory disorders, or sexually transmitted diseases. A disease-causing agent may be detected in a blood sample. A disease-causing agent may be detected in a sample obtained with a swab, such as a throat swab, or a nasal swab, or a mouth swab (e.g., a cheek swab), or a vaginal swab, or other sample, or combinations thereof.

In embodiments, a device may be or comprise a cartridge configured to contain one or more reagent vessels, and one or more reaction vessels, e.g., for use in nucleic acid assays; for use in immunoassays (e.g., ELISA assays); for use in general chemistry assays (e.g., for clinical electrolytes, vitamin levels, blood component levels, and other targets); for use in cytometric assays; and for combinations thereof. In embodiments, such a device may include reagents, reaction vessels, and tools, cuvettes, and other implements for use in nucleic acid assays; for immunoassays (e.g., ELISA assays); general chemistry assays (e.g., for clinical electrolytes, vitamin levels, blood component levels, and other targets); cytometric assays; and for combinations thereof.

In embodiments, a cartridge for use in performing assays for detecting a plurality of disease-causing agents as disclosed herein may include one or more spaces or vessels for holding a swab or swabs. A single swab may be placed in a single space, or in a single vessel; in embodiments, two swabs may be placed in a single space, or single vessel. In embodiments, a plurality of swabs may be placed in a single space, or single vessel. Vessels for holding a swab, or swabs, may contain a reagent, or a diluent, or other solution for use with a swab or swabs.

A nasal swab may be useful for testing for upper respiratory diseases, and a throat swab may be useful for testing lower respiratory diseases. In embodiments, a mouth swab (e.g., a cheek swab, a tongue swab, a gum swab, or other swab taken within the mouth) may be used in addition to, or in place of, a nasal or throat swab. Nasal and throat swabs may be obtained from a single patient, and may be analyzed at the same time, or at nearly the same time. For example, a throat swab may be placed in one vessel in a cartridge, and a nasal swab may be placed in a different vessel in the cartridge, for analysis in an analysis device or analysis system. For example, a mouth swab may be placed in one vessel in a cartridge, and a nasal swab may be placed in a different vessel in the cartridge, for analysis in an analysis device or analysis system. For example, a throat swab may be placed in one vessel in a cartridge, and a mouth swab may be placed in a different vessel in the cartridge, for analysis in an analysis device or analysis system. These vessels may contain a reagent, or a diluent, or other solution for use with the swabs; such reagents may be different for the throat swab and the nasal swab. In embodiments, reagents may be different for a mouth swab than for a throat swab or nasal swab. In a further example, a throat swab and a nasal swab from a single subject may be placed in the same vessel in a device. In a further example, a mouth swab and a nasal swab from a single subject may be placed in the same vessel in a device. In a further example, a throat swab and a mouth swab from a single subject may be placed in the same vessel in a device. The vessel may contain a reagent, or a diluent, or other solution for use with these swabs. The device may be placed in an analysis device, or within an analysis system, for analysis. Such analysis devices and analysis systems may be placed at the same location as that where the sample was obtained; or such analysis devices and analysis systems may be at a different location or locations than the location where the sample was obtained.

In embodiments, a cartridge for use in performing assays for detecting a plurality of disease-causing agents as disclosed herein may include one or more spaces or vessels for holding a blood sample. In embodiments, a cartridge for use in performing assays for detecting a plurality of disease-causing agents as disclosed herein may include one or more spaces or vessels for holding a blood sample and may also include one or more spaces or vessels for holding a swab or swabs. Thus, a device, such as a cartridge, may hold a blood sample and a throat swab; may hold a blood sample and a nasal swab; and may hold a blood sample, a throat swab, and a nasal swab. In embodiments, a device, such as a cartridge, may hold a blood sample and a mouth swab; may hold a blood sample, a mouth swab, and a nasal swab; and may hold a blood sample, a mouth swab, a throat swab, and a nasal swab. Similarly, a device, such as a cartridge, may hold a blood sample and a vaginal swab; and may hold a blood sample, and one or more of a mouth swab, a throat swab, a nasal swab, and a vaginal swab.

In embodiments, a cartridge for use in performing assays for detecting a plurality of disease-causing agents as disclosed herein may include one or more spaces or vessels for holding a urine sample. In embodiments, a cartridge for use in performing assays for detecting a plurality of disease-causing agents as disclosed herein may include one or more spaces or vessels for holding a urine sample and may also include one or more spaces or vessels for holding a swab or swabs. Thus, a device, such as a cartridge, may hold a urine sample and a throat swab; may hold a urine sample and a nasal swab; may hold a urine sample, a throat swab, and a nasal swab; may hold a urine sample, a throat swab, a mouth swab, and a nasal swab; and may hold a urine sample, and one or more of a throat swab, a mouth swab, a vaginal swab, and a nasal swab.

It will be understood that such devices, such as cartridges, may hold other types of samples as well, and that any combination of types of samples may be held by such devices (e.g., cartridges). In any and all such cases, the sample or samples may be analyzed in a sample analysis device or a sample analysis system.

A cartridge may include a sample, and may include reagents for use in processing or testing a sample, disposables for use in processing or testing a sample, or other materials. Following placement of a cartridge on, or insertion of a cartridge into, a sample processing device or system, one or more components of the cartridge may be brought into fluid communication with other components of the sample processing device. For example, if a sample is collected at a cartridge, the sample may be transferred to other portions of the sample processing device. Similarly, if one or more reagents are provided on a cartridge, the reagents may be transferred to other portions of the sample processing device, or other components of the sample processing device may be brought to the reagents. In some embodiments, the reagents or components of a cartridge may remain on-board the cartridge. In some embodiments, no fluidics are included that require tubing or that require maintenance (e.g., manual or automated maintenance).

A sample or reagent may be transferred to a device, such as a sample processing device. A sample or reagent may be transferred within a device. Such transfer of sample or reagent may be accomplished without providing a continuous fluid pathway from cartridge to device. Such transfer of sample or reagent may be accomplished without providing a continuous fluid pathway within a device. In embodiments, such transfer of sample or reagent may be accomplished by a sample handling system (e.g., a pipette); for example, a sample, reagent, or aliquot thereof may be aspirated into an open-tipped transfer component, such as a pipette tip, which may be operably connected to a sample handling system which transfers the tip, with the sample, reagent, or aliquot thereof contained within the tip, to a location on or within the sample processing device. The sample, reagent, or aliquot thereof can be deposited at a location on or within the sample processing device. Sample and reagent, or multiple reagents, may be mixed using a sample handling system in a similar manner. One or more components of the cartridge may be transferred in an automated fashion to other portions of the sample processing device, and vice versa.

Figure 20A:
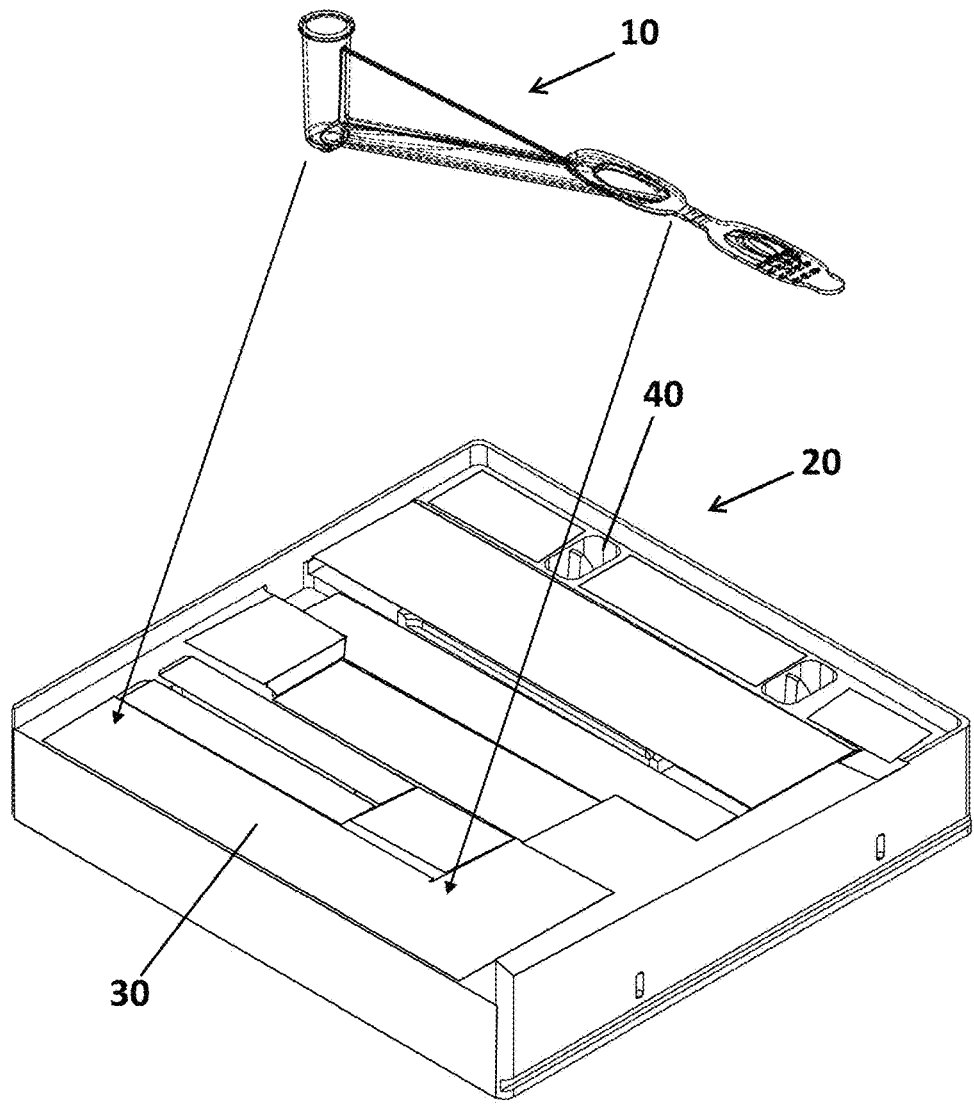
FIG. 20A shows an exemplary vessel for holding a swab (a swab vessel) and an exemplary cartridge (which includes cavities and wells for reagents and vessels, and is configured to hold reagent vessels, reaction vessels, and other vessels and implements). Arrows leading away from the swab vessel indicate how the swab vessel may be placed into a receptacle in the cartridge.
Figure 20B:
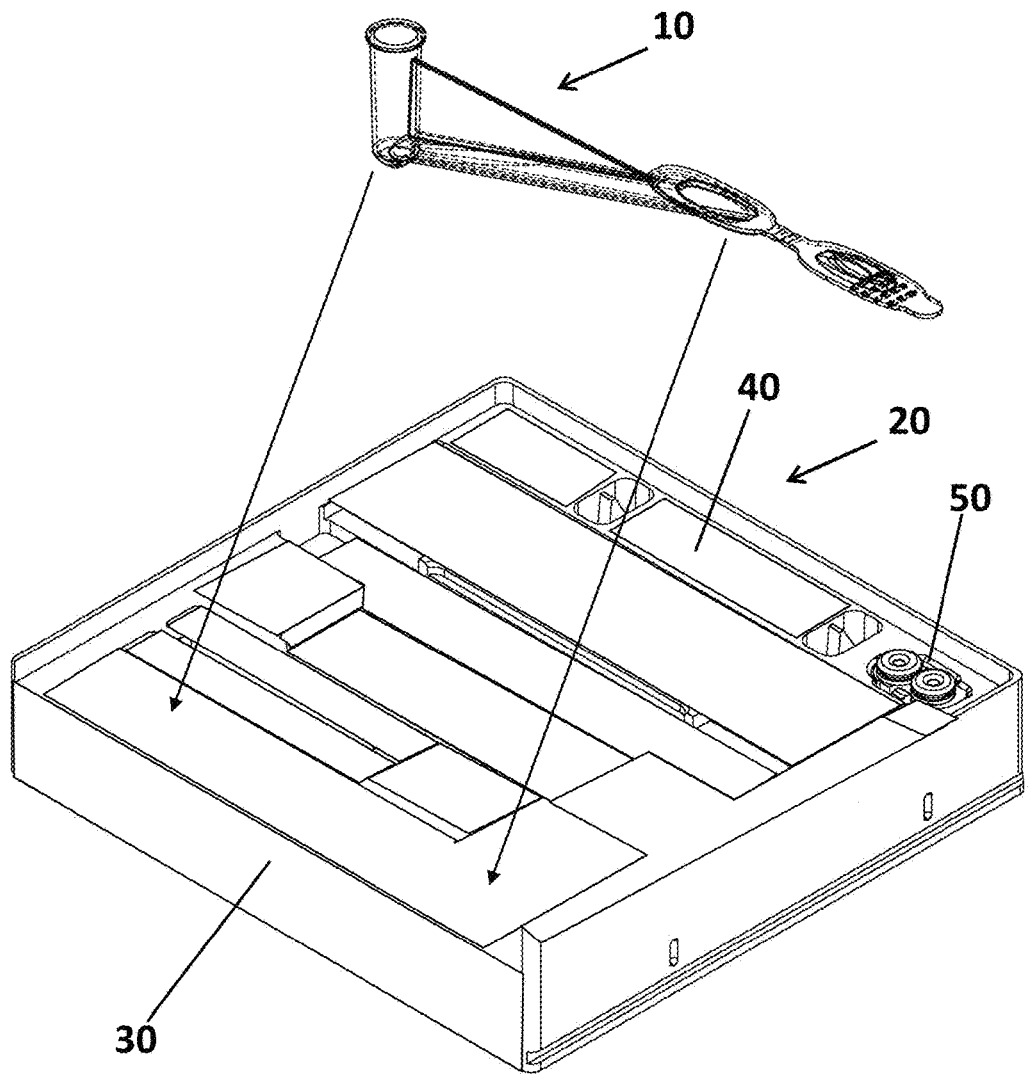
FIG. 20B shows an exemplary swab vessel (configured for holding a swab) and an exemplary cartridge (which includes cavities and wells for reagents and vessels, and is configured to hold reagent vessels, reaction vessels, and other vessels and implements). In addition to the cavities and wells configured to hold reagent vessels, reaction vessels, and other vessels and implements as shown in the embodiment of FIG. 20A, the exemplary cartridge shown in FIG. 20B includes cavities and wells suitable for holding other sample vessels, e.g., blood or urine sample vessels, in addition to swab vessels. Arrows leading away from the swab vessel indicate how the swab vessel may be placed into a receptacle in the cartridge.
Figure 20C:
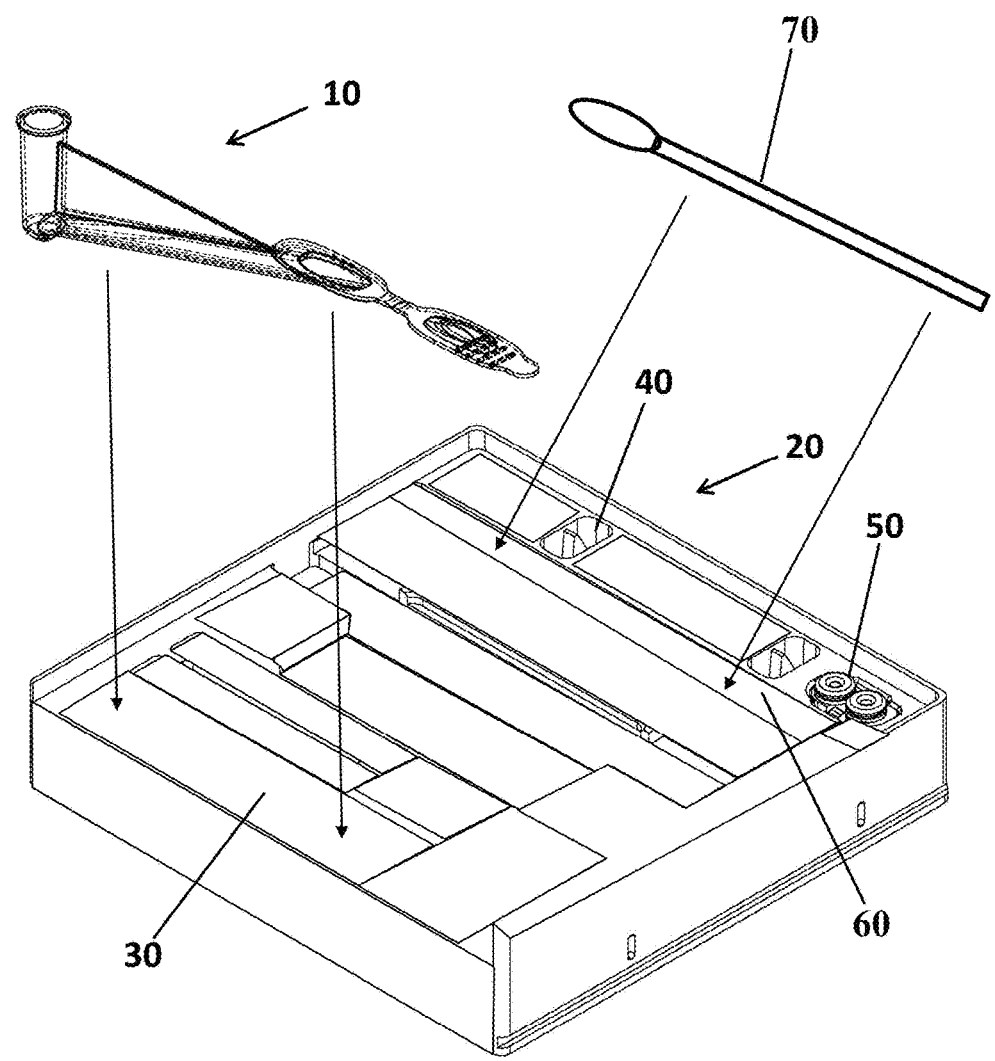
FIG. 20C shows an exemplary swab vessel, and an exemplary cartridge which includes cavities and wells for holding a swab and a swab vessel, as well as cavities and wells configured to hold reagent vessels, reaction vessels, and other vessels and implements (which may optionally include other sample vessels, e.g., blood or urine sample vessels). Arrows leading away from the swab indicate how the swab may be placed into a swab receptacle in the cartridge. Arrows leading away from the swab vessel indicate how the swab vessel may be placed into a swab vessel receptacle in the cartridge.

As shown in FIG. 20A, FIG. 20B, and FIG. 20C, a vessel for holding a swab may be loaded onto a cartridge, where it may be retained until needed for analysis; the cartridge may be loaded onto an analysis device or analysis system, thereby loading the swab (and any other samples or sample containers on the cartridge as well). As shown in FIG. 20A, a vessel for holding a swab (a swab vessel 10) may be loaded onto a cartridge 20 by placement into a receptacle 30. The cartridge 20 as shown also includes cavities and wells 40 for receiving and holding reagents and vessels. A swab vessel 10 may contain a swab in place within the swab vessel 10, or may be loaded onto a cartridge without a swab in place within the swab vessel 10.

As shown in FIG. 20B, a vessel for holding a swab (a swab vessel 10) may be loaded onto a cartridge 20 by placement into a receptacle 30. The cartridge 20 as shown also includes cavities and wells 40 for receiving and holding reagents and vessels. In the embodiment shown in FIG. 20B, the cartridge 20 also includes a sample collection vessel 50, which may hold, e.g., blood, urine, or other sample. The arrows leading away from the swab vessel 10 indicate how the swab vessel 10 may be placed into a receptacle 30 in the cartridge 20.

As shown in FIG. 20C, a vessel for holding a swab (a swab vessel 10) may be loaded onto a cartridge 20 by placement into a receptacle 30. The cartridge 20 as shown also includes cavities and wells 40 for receiving and holding reagents and vessels. As shown in the embodiment of FIG. 20C, the cartridge 20 includes a swab receptacle 60 configured to hold a swab 70. In embodiments (e.g., in the embodiment illustrated in FIG. 20C) a cartridge 20 having a swab receptacle 60 may optionally include a sample collection vessel 50, which may hold, e.g., blood, urine, or other sample. Such a swab 70 may be held in swab receptacle 60 prior to its use in collecting a sample. In embodiments, a swab 70 may be placed within a swab vessel 10 after collection of a sample with swab 70. In the embodiment shown in FIG. 20C, swab vessel 10 may be loaded onto a cartridge without a swab in place within the swab vessel 10 prior to use of swab 70, and swab vessel 10 may be replaced in a receptacle 30, holding swab 70 within swab vessel 10 after collection of a sample by swab 70.

Figure 21:
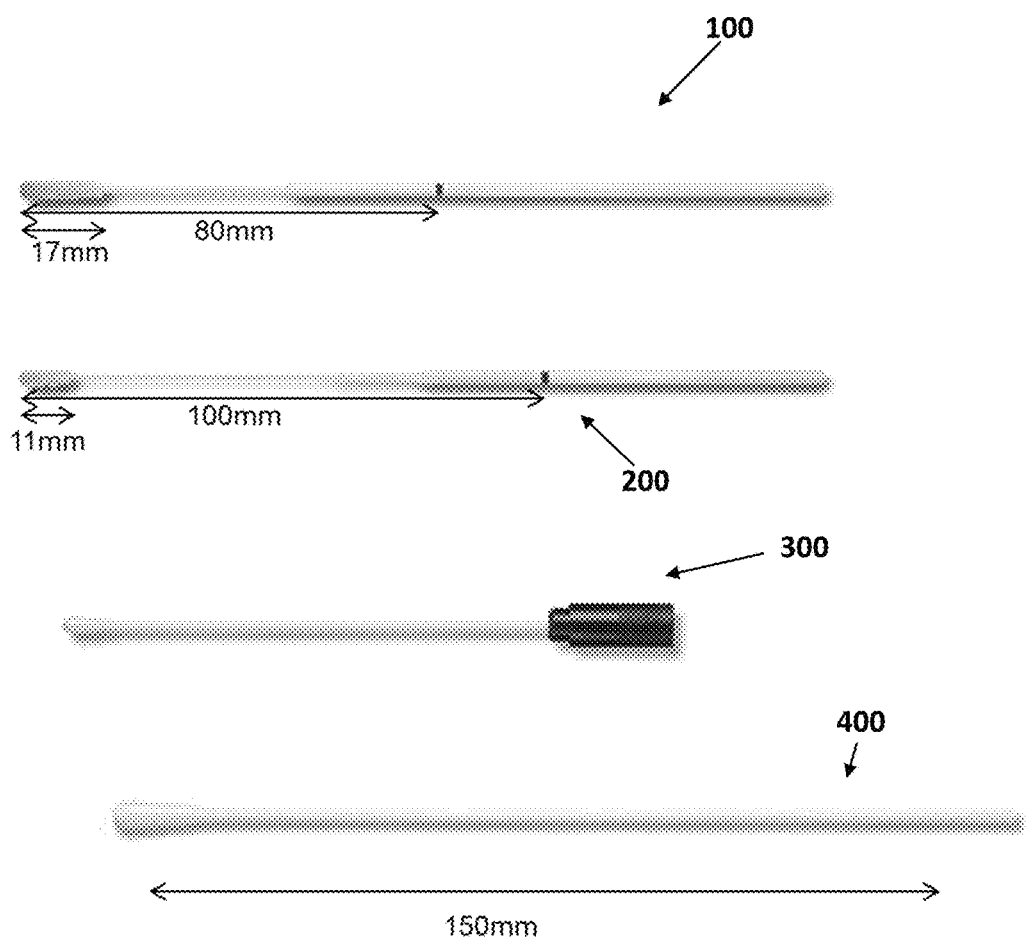
FIG. 21 shows examples of swabs which may be used to obtain samples from the throat, nasal passages, cheeks, or other body locations of subjects.

Swabs may be any suitable swab for collection of a sample. Several examples of swabs suitable for use in sample collection are shown in FIG. 21. Swabs with flocked tips (swab 100, and the shorter swab 200, suitable for pediatric use), or those also suitable for use in establishing cultures of material obtained by swabbing a body orifice, a body cavity or surface of a subject (swab 300), cotton-tipped swabs (swab 400), and other swabs may be used to collect a sample from a patient for use with the methods, systems, and devices disclosed herein. For example, samples may be obtained by swabbing a nasal cavity, a throat, a mouth, a vagina, or other orifice, body cavity, or location on or within a subject.

Systems

An analysis system, which may include an analysis device, such as a sample processing device, may have a fluid handling system (also termed herein a sample handling system). A fluid handling system may perform, or may aid in performing, transport, dilution, extraction, aliquotting, mixing, and other actions with a fluid, such as a sample. In some embodiments, a fluid handling system may be contained within a device housing. A fluid handling system may permit the collection, delivery, processing and/or transport of a fluid, dissolution of dry reagents, mixing of liquid and/or dry reagents with a liquid, as well as collection, delivery, processing and/or transport of non-fluidic components, samples, or materials. The fluid may be a sample, a reagent, diluent, wash, dye, or any other fluid that may be used by the device, and may include, but not limited to, homogenous fluids, different liquids, emulsions, suspensions, and other fluids. A fluid handling system, including without limitation a pipette, may also be used to transport vessels (with or without fluid contained therein) around the device. The fluid handling system may dispense or aspirate a fluid. The sample may include one or more particulate or solid matter floating within a fluid.

In embodiments, a fluid handling system may comprise a pipette, pipette tip, syringe, capillary, or other component. The fluid handling system may have portion with an interior surface and an exterior surface and an open end. The fluid handling system may comprise a pipette, which may include a pipette body and a pipette nozzle, and may comprise a pipette tip. A pipette tip may or may not be removable from a pipette nozzle. In embodiments, a fluid handling system may use a pipette mated with a pipette tip; a pipette tip may be disposable. A tip may form a fluid-tight seal when mated with a pipette. A pipette tip may be used once, twice, or more times. In embodiments, a fluid handling system may use a pipette or similar device, with or without a pipette tip, to aspirate, dispense, mix, transport, or otherwise handle the fluid. The fluid may be dispensed from the fluid handling system when desired. The fluid may be contained within a pipette tip prior to being dispensed, e.g., from an orifice in the pipette tip. In embodiments, or instances during use, all of the fluid may be dispensed; in other embodiments, or instances during use, a portion of the fluid within a tip may be dispensed. A pipette may selectively aspirate a fluid. The pipette may aspirate a selected amount of fluid. The pipette may be capable of actuating stirring mechanisms to mix the fluid within the tip or within a vessel. The pipette may incorporate tips or vessels creating continuous flow loops for mixing, including of materials or reagents that are in non-liquid form. A pipette tip may also facilitate mixture by metered delivery of multiple fluids simultaneously or in sequence, such as in 2-part substrate reactions.

A fluid handling system may include one or more fluidically isolated or hydraulically independent units. For example, the fluid handling system may include one, two, or more pipette tips. The pipette tips may be configured to accept and confine a fluid. The tips may be fluidically isolated from or hydraulically independent of one another. The fluid contained within each tip may be fluidically isolated or hydraulically independent from one fluids in other tips and from other fluids within the device. The fluidically isolated or hydraulically independent units may be movable relative to other portions of the device and/or one another. The fluidically isolated or hydraulically independent units may be individually movable. A fluid handling system may comprise one or more base or support. A base or support may support one or more pipette or pipette units.

A base or support may connect one or more pipettes of the fluid handling system to one another.

A sample processing system, which may include a sample processing device, may be configured to perform processing steps or actions on a sample obtained from a subject. Sample processing may include sample preparation, including, e.g., sample dilution, division of a sample into aliquots, extraction, contact with a reagent, filtration, separation, centrifugation, or other preparatory or processing action or step. A sample processing device may be configured to perform one or more sample preparation action or step on the sample. Optionally, a sample may be prepared for a chemical reaction and/or physical processing step. A sample preparation action or step may include one or more of the following: centrifugation, separation, filtration, dilution, enriching, purification, precipitation, incubation, pipetting, transport, chromatography, cell lysis, cytometry, pulverization, grinding, activation, ultrasonication, micro column processing, processing with magnetic beads, processing with nanoparticles, or other sample preparation action or steps. For example, sample preparation may include one or more step to separate blood into serum and/or particulate fractions, or to separate any other sample into various components. Sample preparation may include one or more step to dilute and/or concentrate a sample, such as a clinical sample or biological sample, e.g., of blood, urine, sputum, material obtained from a nasal swab, a throat swab, a cheek swab, or other sample, or other clinical or biological samples. Sample preparation may include adding an anti-coagulant or other ingredients to a sample. Sample preparation may also include purification of a sample. In embodiments, all sample processing, preparation, or assay actions or steps are performed by a single device. In embodiments, all sample processing, preparation, or assay actions or steps are performed within a housing of a single device. In embodiments, most sample processing, preparation, or assay actions or steps are performed by a single device, and may be performed within a housing of a single device. In embodiments, many sample processing, preparation, or assay actions or steps are performed by a single device, and may be performed within a housing of a single device. In embodiments, sample processing, preparation, or assay actions or steps may be performed by more than one device.

A sample processing system, which may include a sample processing device, may be configured to run one or more assay on a sample, and to obtain data from the sample. An assay may include one or more physical or chemical treatments, and may include running one or more chemical or physical reactions. A sample processing device may be configured to perform one, two or more assays on a small sample of bodily fluid. One or more chemical reaction may take place on a sample having a volume, as described elsewhere herein. For example one or more chemical reaction may take place in a pill having less than femtoliter volumes. In an instance, the sample collection unit is configured to receive a volume of the bodily fluid sample equivalent to a single drop or less of blood or interstitial fluid. In embodiments, the volume of a sample may be a small volume, where a small volume may be a volume that is less than about 1000 µL, or less than about 500 µL, or less than about 250 µL, or less than about 150 µL, or less than about 100 µL, or less than about 75 µL, or less than about 50 µL, or less than about 40 µL, or less than about 20 µL, or less than about 10 µL, or other small volume. In embodiments, all sample assay actions or steps are performed on a single sample. In embodiments, all sample assay actions or steps are performed by a single device. In embodiments, all sample assay actions or steps are performed within a housing of a single device. In embodiments, most sample assay actions or steps are performed by a single device, and may be performed within a housing of a single device. In embodiments, many sample assay actions or steps are performed by a single device, and may be performed within a housing of a single device. In embodiments, sample processing, preparation, or assay actions or steps may be performed by more than one device.

A sample processing system, which may include a sample processing device, may be configured to perform a plurality of assays on a sample. For example, a sample processing device may be configured to detect, or to identify, or to measure pathogen-identifying material in a sample. In embodiments, a sample processing device may be configured to perform a plurality of assays on a single sample. In embodiments, a sample processing device may be configured to perform a plurality of assays on a single sample, where the sample is a small sample. For example, a small sample may have a sample volume that is a small volume of less than about 1000 µL, or less than about 500 µL, or less than about 250 µL, or less than about 150 µL, or less than about 100 µL, or less than about 75 µL, or less than about 50 µL, or less than about 40 µL, or less than about 20 µL, or less than about 10 µL, or other small volume. A sample processing device may be capable of performing multiplexed assays on a single sample. A plurality of assays may be run simultaneously; may be run sequentially; or some assays may be run simultaneously while others are run sequentially. One or more control assays and/or calibrators (e.g., including a configuration with a control of a calibrator for the assay/tests) can also be incorporated into the device; control assays and assay on calibrators may be performed simultaneously with assays performed on a sample, or may be performed before or after assays performed on a sample, or any combination thereof. In embodiments, all sample assay actions or steps are performed by a single device. In embodiments, all of a plurality of assay actions or steps are performed within a housing of a single device. In embodiments, most sample assay actions or steps, of a plurality of assays, are performed by a single device, and may be performed within a housing of a single device. In embodiments, many sample assay actions or steps, of a plurality of assays, are performed by a single device, and may be performed within a housing of a single device. In embodiments, sample processing, preparation, or assay actions or steps may be performed by more than one device.

In embodiments, all of a plurality of assays may be performed in a short time period. In embodiments, such a short time period comprises less than about three hours, or less than about two hours, or less than about one hour, or less than about 40 minutes, or less than about 30 minutes, or less than about 25 minutes, or less than about 20 minutes, or less than about 15 minutes, or less than about 10 minutes, or less than about 5 minutes, or less than about 4 minutes, or less than about 3 minutes, or less than about 2 minutes, or less than about 1 minute, or other short time period.

In embodiments of the methods, devices, and systems disclosed herein, systems may include one or more assay stations, where, for example, a sample and a reagent may be mixed. In embodiments of the methods, devices, and systems disclosed herein, systems may include one or more detection stations, where, for example, a sample, or a label attached to a target in a sample, or other signal indicative of the presence of a target analyte in a sample, may be detected. In embodiments of the methods, devices, and systems disclosed herein, one or more assay stations may also serve as a detection station. For example, where an assay reacts a reagent or reagents with an analyte within a vessel, the vessel serves as an assay station; where the vessel is transparent to a signal produced by the reaction, and where the vessel is adjacent a detector effective that the signal (and thus the presence or concentration of the analyte) may be detected, the vessel also serves as a detection station. For example, some nucleic acid analysis methods and systems provide a heating block (or other temperature-controlling element) and a detector at, or near to, a position in which a vessel containing sample and reagents is disposed during a reaction, and during detection of the results of the reaction. In such an embodiment, a vessel is not moved from the location of the reaction to a different location for detection of the results of the reaction, so the vessel (and the location and accompanying devices and operative elements) serves as both an assay station and a detection station. In further embodiments, a vessel is moved from a location where a reaction occurs, or a sample (or sample-containing) solution is moved from the assay vessel, to a different location or vessel where detection occurs. In such an embodiment, where a vessel (or solution) is moved from the location of the reaction to a different location for detection of the results of the reaction, the vessel (and the location and accompanying assay devices and operative elements) serves as an assay station, and a different location (and devices or elements) serves as a detection station.

Systems for detecting the presence of one or more of a plurality of markers indicative of an infectious disease in a small-volume clinical sample include, for example, a) a sample handling system; b) a detection station comprising an optical sensor; c) a fluidically isolated sample collection unit configured to retain a clinical sample; d) an assay station comprising at least a first and a second fluidically isolated assay unit, wherein the first unit comprises a first reagent and the second unit comprises a second reagent; and e) a controller, wherein the controller comprises a local memory and is operatively coupled to the sample handling system and the detection station. Such systems may be configured to perform assays with one or both of the first and second assay units; wherein the local memory of the controller comprises a protocol comprising instructions for: i) directing the sample handling system to transfer a portion of the clinical sample to the first assay unit and to the second assay unit; and ii) directing the sample handling system to transfer the first assay unit and the second unit assay unit to the detection station. In further embodiments, an assay station in such systems may include at least a first, second, and third fluidically isolated assay unit, wherein the first unit comprises a first reagent, the second unit comprises a second reagent, and the third unit comprises a third reagent. In further embodiments, an assay station in such systems may include at least a first, second, third, and fourth fluidically isolated assay unit, wherein the first unit comprises a first reagent, the second unit comprises a second reagent, the third unit comprises a third reagent, and the fourth unit comprises a fourth reagent. It will be understood that embodiments of such systems may include more than four assay units; or other numbers of assay units.

In embodiments, assays are performed with any one or more of the first, second, and third assay units; or with any one or more of the first, second, third, and fourth assay units, wherein the local memory of the controller comprises a protocol comprising instructions for: i) directing the sample handling system to transfer a portion of the clinical sample to the first assay unit, the second assay unit, and, where applicable, the third assay unit and/or fourth assay units; and ii) directing the sample handling system to transfer the first assay unit, the second assay unit, and, where appropriate, the third assay unit and/or the fourth assay unit to the detection station.

Further systems for detecting the presence of one or more of a plurality of markers indicative of an infectious disease in a small-volume clinical sample include a) a sample handling system; b) a detection station comprising an optical sensor; c) a fluid handling system configured to transport fluids between components of said system, wherein said transport of fluids comprises transport of isolated aliquots of fluid; d) a fluidically isolated sample collection unit configured to retain a clinical sample; e) an assay station comprising at least a first, second, and third fluidically isolated assay unit, wherein the first unit comprises a first reagent, the second unit comprises a second reagent, and the third unit comprises a third reagent; and f) a controller, wherein the controller comprises a local memory and is operatively coupled to the sample handling system and the detection station. Such systems may be configured to perform assays with any one or more of the first, second, and third assay units; wherein the local memory of the controller comprises a protocol comprising instructions for: i) directing the sample handling system to transfer a portion of the clinical sample to the first assay unit, the second assay unit and the third assay unit; and ii) directing the sample handling system to transfer the first assay unit, the second assay unit, and the third assay unit to the detection station. It will be understood that embodiments of such systems may include only two assay units; or may include four assay units; or other numbers of assay units.

Clinical sample processing systems for use in performing assays as disclosed herein may include a) a sample handling system; b) a detection station comprising an optical sensor; c) a fluidically isolated sample collection unit configured to retain a clinical sample; d) an assay station comprising at least a first, second, and third fluidically isolated assay unit, wherein the first unit comprises an antibody, the second unit comprises an oligonucleotide, and the third unit comprises a chromogen or a dye or other label; and e) a controller, wherein the controller is operatively coupled to the sample handling system, wherein the sample handling system is configured to transfer a portion of the clinical sample from the sample collection unit to each of the first assay unit, the second assay unit, and the third assay unit, and the device is configured to perform an immunoassay, a nucleic acid assay, and a general chemistry assay comprising a chromogen.

Such systems may be point-of service (POS) systems. These systems may be contained within a housing. A system located at a POS location may be configured for use in analyzing a sample at the POS location. These systems may be POS systems configured to perform a plurality of assays on a single small volume sample, or on aliquots thereof.

EXAMPLE 1

Testing for and Detecting Nucleic Acid Markers of Disease and Disease-Causing Agents Disease-causing agents such as viruses, bacteria, yeast, fungi, and other micro-organisms have identifying nucleic acids and proteins, among other identifying characteristics which may serve as markers. Markers indicative of a disease, or of a disease-causing agent, such as a respiratory disease, or a form of influenza, or a sexually transmitted disease, or other disease, include nucleic acid markers.

As shown in the figures, markers for many diseases may be tested for, and may be detected, using nucleic acid assays as disclosed herein. All of the disease-causing agents tested for in the tests shown in FIG. 1A were detected within 40 minutes, with most of the agents detected within about 30 minutes. Detection times for copy numbers of 100 copies per microliter (c/µl) were shorter than for lower copy numbers (10 c/µl). The detection time for samples having 100 copies per µL are shown in FIG. 1B; most were near or less than 20 minutes, with many detection times of about 15 minutes or less.

FIG. 1A provides a graphic summary of the durations of time from the initiation of nucleic acid assay until detection of the presence of a target nucleic acid in a sample for a range of markers and for two different concentration ranges of the markers (10 c/µl and 100 c/µl, where "c/µl" means copies per microliter (µL)). The 10 c/µl results are shown to the left of the 100 c/µl results for each disease type (influenza (Flu), respiratory, and sexually transmitted disease (STD)) shown in the figure. The times are labeled "LOD" ("length of delay"). The vertical axis is shown in units of relative fluorescence (relative fluorescence units, RFU), in thousands.

Figure 1B:
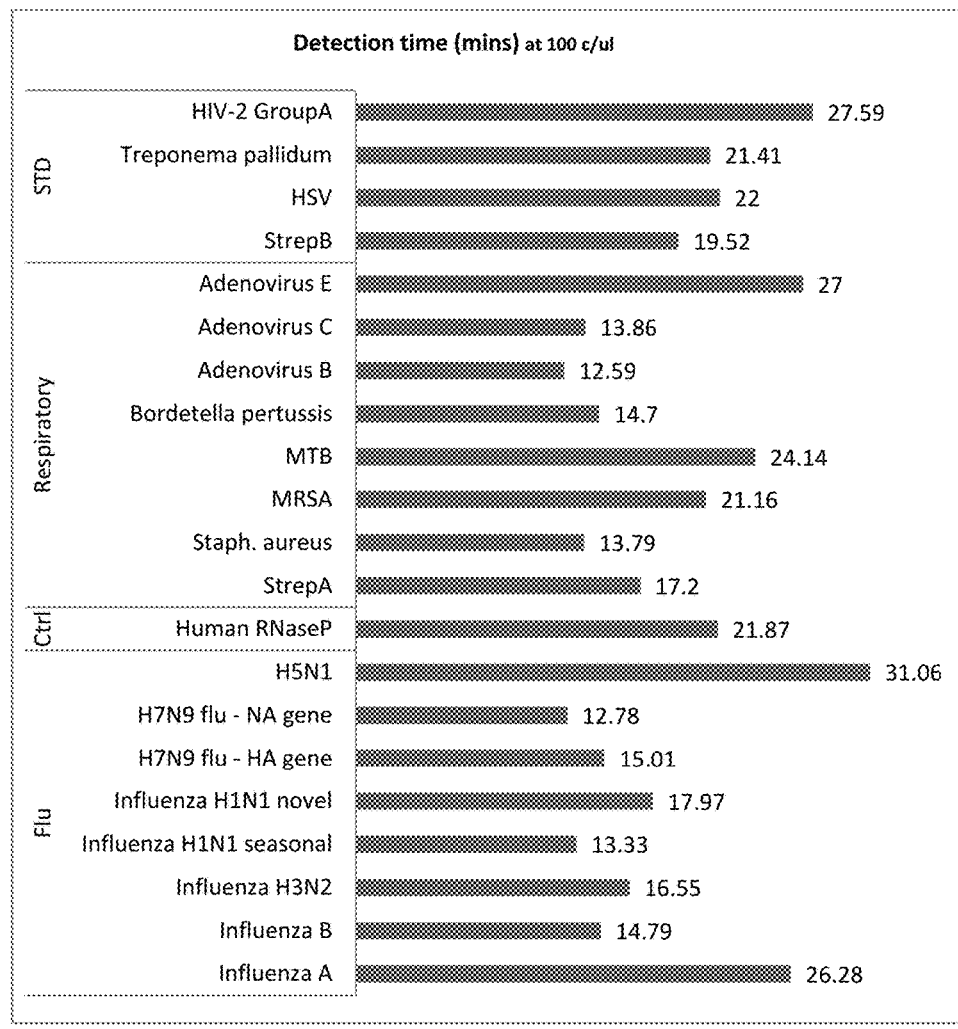
FIG. 1B provides a bar chart showing the durations of time from the initiation of nucleic acid assay until detection of the presence of a target nucleic acid in a sample for the indicated markers for various diseases (at 100 c/µl).

FIG. 1B provides a bar chart showing the durations of time from the initiation of nucleic acid assay until detection of the presence of a target nucleic acid in a sample for the indicated markers for various diseases (at 100 c/µl).

Figure 1C:
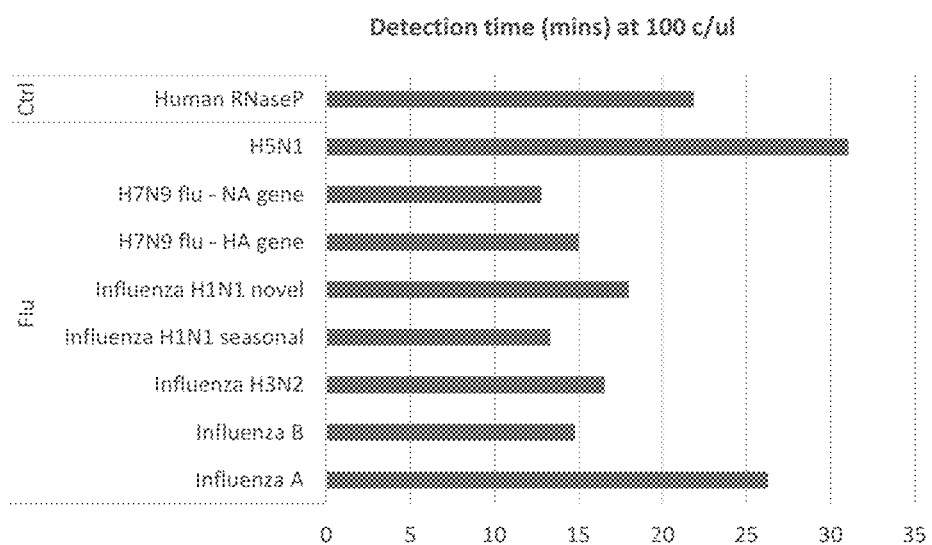
FIG. 1C provides a bar chart showing the durations of time from the initiation of nucleic acid assay until detection of the presence of a target nucleic acid in a sample for the indicated markers for several influenza strains and identifying targets (at 100 c/µl).
Figure 1D:
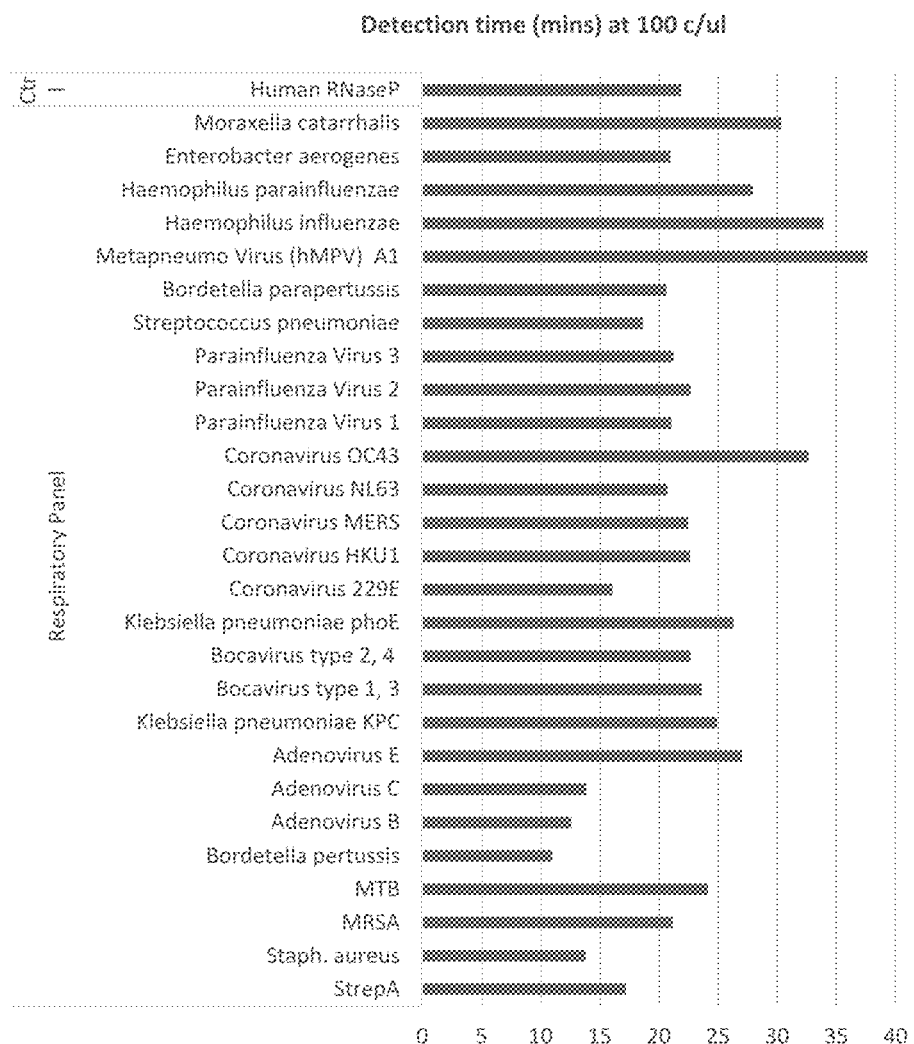
FIG. 1D provides a bar chart showing the durations of time from the initiation of nucleic acid assay until detection of the presence of a target nucleic acid in a sample for the indicated markers of several respiratory diseases (at 100 c/µl).
Figure 1E:
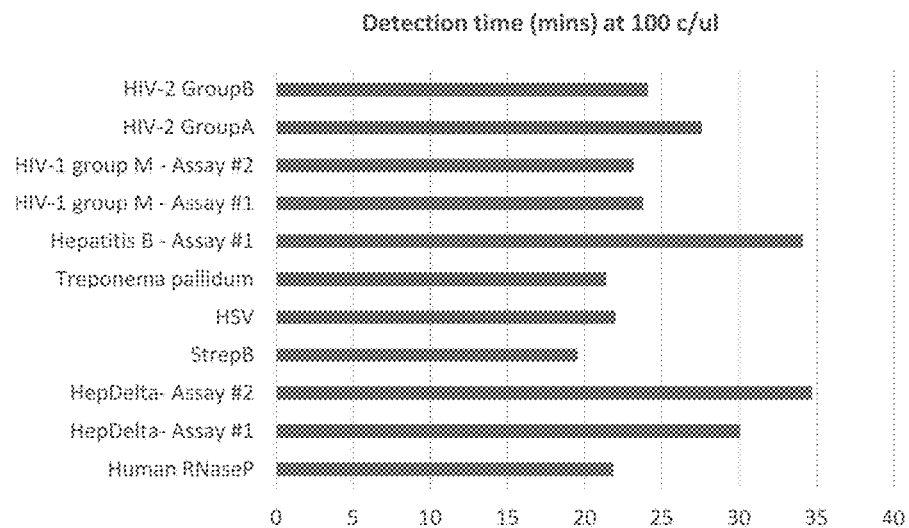
FIG. 1E provides a bar chart showing the durations of time from the initiation of nucleic acid assay until detection of the presence of a target nucleic acid in a sample for the indicated markers for several sexually transmitted diseases (at 100 c/µl).
Figure 1F:
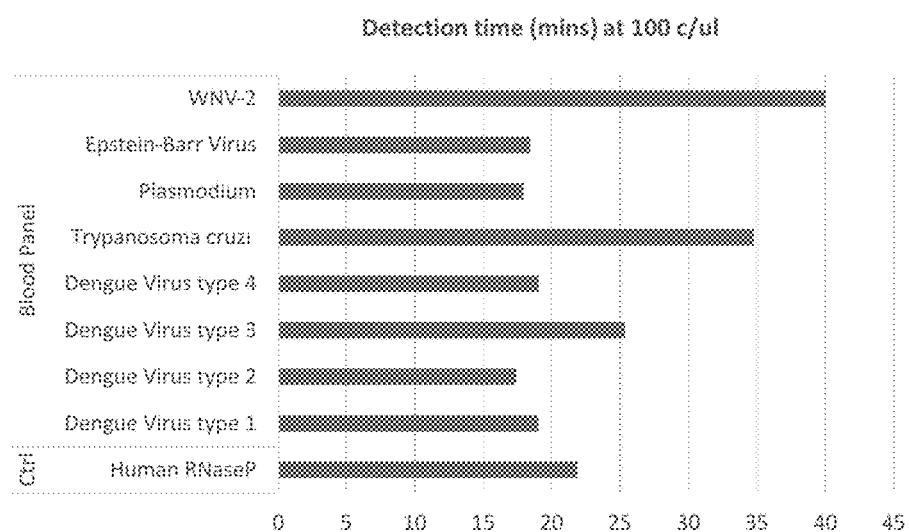
FIG. 1F provides a bar chart showing the durations of time from the initiation of nucleic acid assay until detection of the presence of a target nucleic acid in a sample for the indicated markers for several diseases that can be detected in blood (at 100 c/µl).

Further information regarding detection time for various diseases, grouped by general location of the infection, or type of disease, or samples by which the diseases may be detected are presented in FIGS. 1C through 1F (all at 100 c/µl). FIG. 1C shows the durations of time from the initiation of nucleic acid assay until detection for several influenza strains and identifying targets. FIG. 1D shows the durations of time from the initiation of nucleic acid assay until detection for several respiratory diseases. FIG. 1E shows the durations of time from the initiation of nucleic acid assay until detection for several sexually transmitted diseases. FIG. 1F shows the durations of time from the initiation of nucleic acid assay until detection for several diseases that can be detected in blood.

Complementary information is presented in Table 2A indicating the numbers of copies per µl that are detectable with these assays for several diseases.

TABLE 2A

| | | |
|---|---|---|
| 1 | *Trypanosoma cruzi* | <0.01 c/uL |
| 2 | *Plasmodium* | <0.1 c/uL |
| 3 | *Bordetella pertussis* | <4 c/uL |
| 4 | Influenza B | <10 c/uL |
| 5 | Influenza H3N2 | <10 c/uL |
| 6 | Influenza H1N1 seasonal | <10 c/uL |
| 7 | Influenza H1N1 novel | <10 c/uL |
| 8 | H7N9 flu - HA gene | <10 c/uL |
| 9 | H7N9 flu - NA gene | <10 c/uL |
| 10 | Human RNaseP | <10 c/uL |
| 11 | StrepA | <10 c/uL |
| 12 | *Staph. aureus* | <10 c/uL |
| 13 | MRSA | <10 c/uL |
| 14 | Adenovirus B | <10 c/uL |
| 15 | Adenovirus C | <10 c/uL |
| 16 | Adenovirus E | <10 c/uL |
| 17 | *Klebsiella pneumoniae* KPC | <10 c/uL |
| 18 | Bocavirus type 2, 4 | <10 c/uL |
| 19 | Coronavirus 229E | <10 c/uL |
| 20 | Coronavirus NL63 | <10 c/uL |
| 21 | *Streptococcus pneumoniae* | <10 c/uL |
| 22 | *Bordetella parapertussis* | <10 c/uL |
| 23 | *Haemophilus parainfluenzae* | <10 c/uL |
| 24 | *Enterobacter aerogenes* | <10 c/uL |
| 25 | *Moraxella catarrhalis* | <10 c/uL |
| 26 | StrepB | <10 c/uL |

TABLE 2A-continued

| | | |
|---|---|---|
| 27 | HSV | <10 c/uL |
| 28 | *Treponema pallidum* | <10 c/uL |
| 29 | Hepatitis B - Assay #1 | <10 c/uL |
| 30 | HIV-1 group M - Assay #1 | <10 c/uL |
| 31 | HIV-1 group M - Assay #2 | <10 c/uL |
| 32 | HIV-2 GroupA | <10 c/uL |
| 33 | Dengue Virus type 1 | <10 c/uL |
| 34 | Dengue Virus type 2 | <10 c/uL |
| 35 | Dengue Virus type 3 | <10 c/uL |
| 36 | Dengue Virus type 4 | <10 c/uL |
| 37 | Epstein-Barr Virus | <10 c/uL |
| 38 | Influenza A | <100 c/uL |
| 39 | H5N1 | <100 c/uL |
| 40 | MTB | <100 c/uL |
| 41 | Bocavirus type 1, 3 | <100 c/uL |
| 42 | *Klebsiella pneumoniae* phoE | <100 c/uL |
| 43 | Coronavirus HKU1 | <100 c/uL |
| 44 | Coronavirus MERS | <100 c/uL |
| 45 | Coronavirus OC43 | <100 c/uL |
| 46 | Parainfluenza Virus 1 | <100 c/uL |
| 47 | Parainfluenza Virus 2 | <100 c/uL |
| 48 | Parainfluenza Virus 3 | <100 c/uL |
| 49 | Metapneumo Virus (hMPV) A1 | <100 c/uL |
| 50 | *Haemophilus influenzae* | <100 c/uL |
| 51 | HepDelta- Assay #1 | <100 c/uL |
| 52 | HepDelta- Assay #2 | <100 c/uL |
| 53 | HIV-2 GroupB | <100 c/uL |
| 54 | WNV-2 | <100 c/uL |

In the above Tables and elsewhere herein, "NA" indicates neuraminidase; "HA" indicates hemagglutinin; "*Klebsiella* pneumonia KPC" indicates *Klebsiella* pneumonia carbapenemase; the "phoE" of "*Klebsiella* pneumonia phoE" indicates phosphate transport porin; "MRSA" indicates Methicillin-resistant *Staphylococcus aureus*; "Metapneumo Virus (hMPV)" indicates human Metapneumo Virus; "HepDelta" indicates Hepatitis Delta; "WNV" indicates West Nile Virus; "Pan Inf A" and "Pan Inf B" indicate assays generic for all strains of the indicated influenza; and "HAI" indicates hospital acquired infection.

The average detection time for these 54 diseases (at 100 c/µl or less) was less than 23 minutes (22.77 minute average). A smaller subset of 35 diseases measured at 10 c/µl or less had an average detection time of less than 30 minutes (29.11 minute average). These assays, including assays for these diseases, are suitable for validation for use in Clinical Laboratories Improvement Act (CLIA) laboratories. For example, such assays for several forms of influenza (pandemic influenza A, pandemic influenza B, H1N1-Novel, H1N1-Seasonal, and H3N2 influenza) have been performed through CLIA Validation.

Figure 2A:
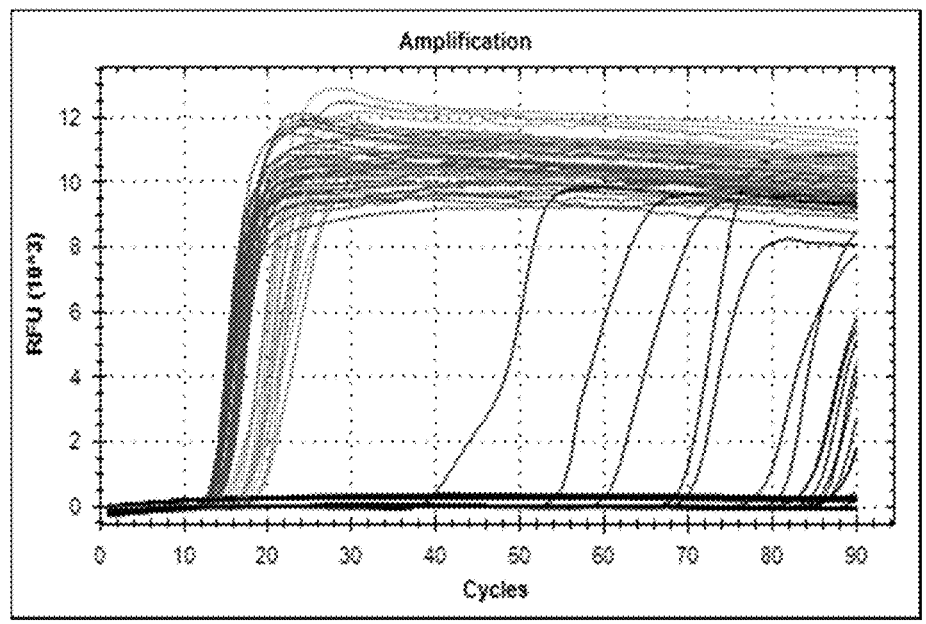
FIG. 2A shows amplification over time, showing detection of influenza A (seasonal H1N1 strain) marker at times well before any significant amounts of amplification of non-target nucleic acid message occurred. The horizontal axis is denominated in "cycles" although no cycling of temperature was used; each unit of "cycles" is approximately one minute, so that the numbers of the horizontal axis may be read in terms of minutes. The vertical axis is shown in units of relative fluorescence (relative fluorescence units, RFU), in thousands.
Figure 2B:
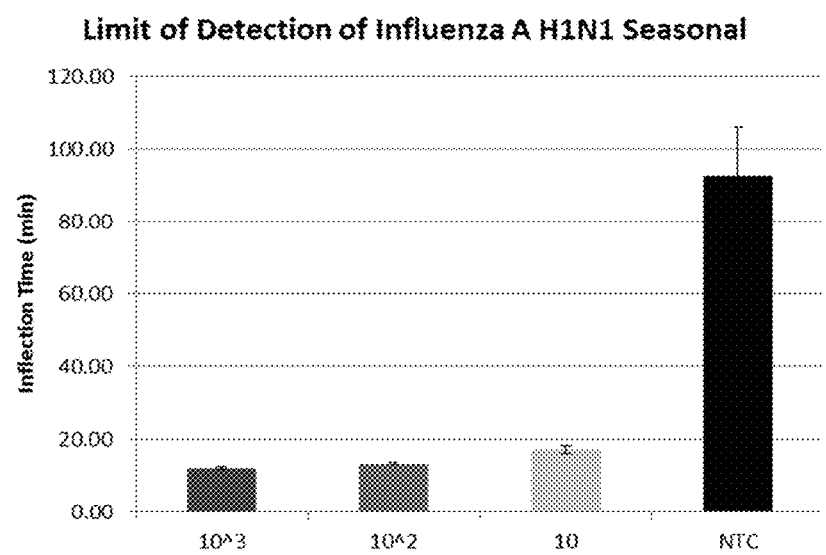
FIG. 2B shows the limit of detection of influenza A (seasonal H1N1 strain) in a sample. The height of the bars indicates the time until the copy number shows an inflection (rises significantly above the background level), with the horizontal axis indicating the initial numbers of copies of influenza A (seasonal H1N1 strain) message; "NTC" indicates "no template control" (no added copies of the target marker).
Figure 3A:
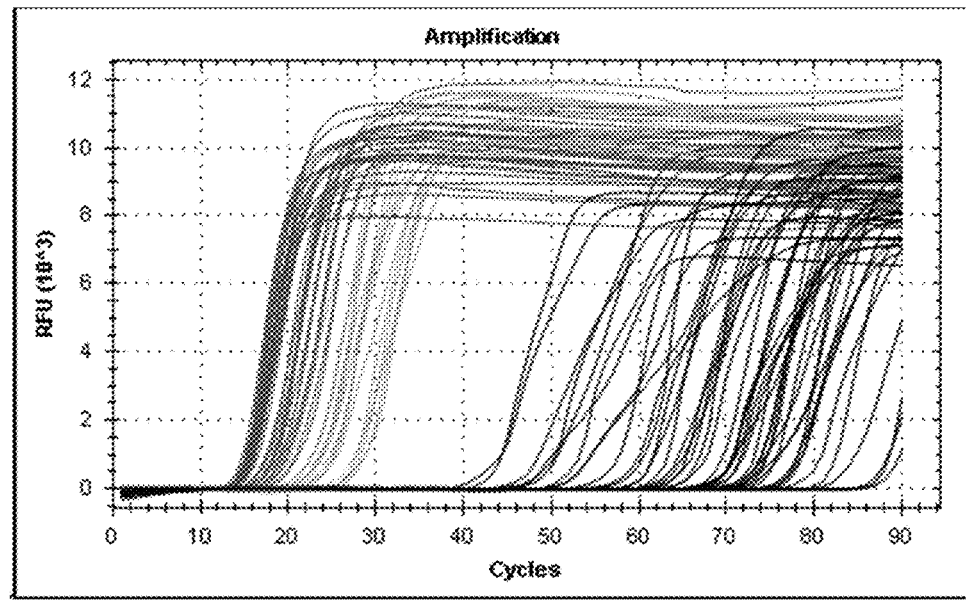
FIG. 3A shows amplification over time, showing detection of influenza A (novel H1N1 strain) marker at times well before any significant amounts of amplification of non-target nucleic acid message occurred. The horizontal axis is denominated in "cycles" although no cycling of temperature was used; each unit of "cycles" is approximately one minute, so that the numbers of the horizontal axis may be read in terms of minutes. The vertical axis is shown in units of relative fluorescence (relative fluorescence units, RFU), in thousands.
Figure 3B:
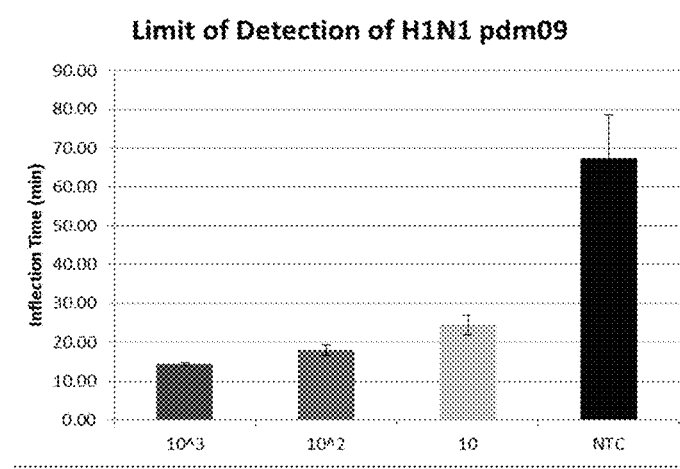
FIG. 3B shows the limit of detection of influenza A (novel H1N1 strain) in a sample. The height of the bars indicates the time until the copy number shows an inflection (rises significantly above the background level), with the horizontal axis indicating the initial numbers of copies of influenza A (novel H1N1 strain) message; "NTC" indicates "no template control" (no added copies of the target marker).
Figure 4A:
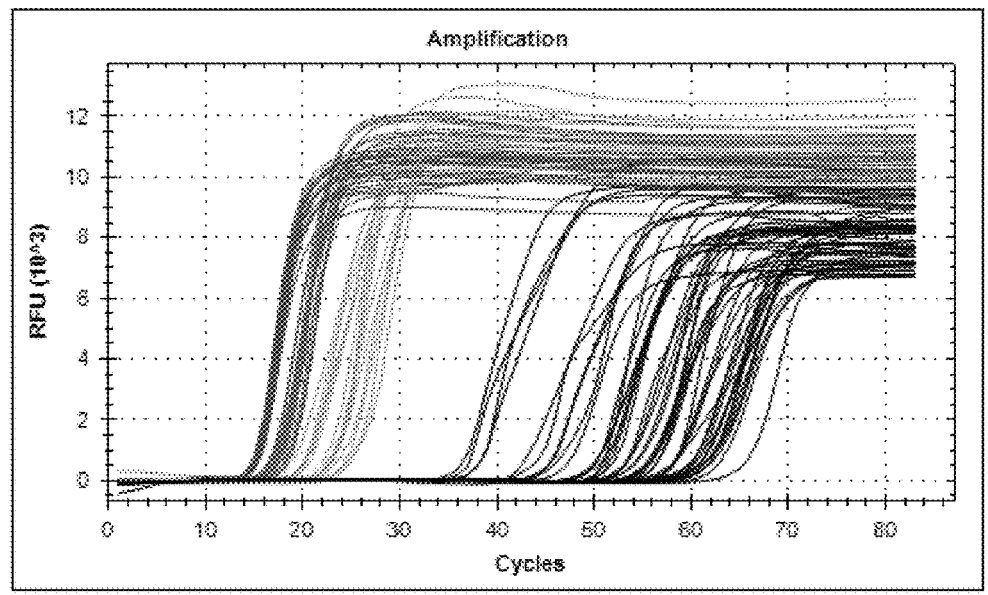
FIG. 4A shows amplification over time, showing detection of influenza A (H3N2 strain) marker at times well before any significant amounts of amplification of non-target nucleic acid message occurred. The horizontal axis is denominated in "cycles" although no cycling of temperature was used; each unit of "cycles" is approximately one minute, so that the numbers of the horizontal axis may be read in terms of minutes. The vertical axis is shown in units of relative fluorescence (relative fluorescence units, RFU), in thousands.
Figure 4B:
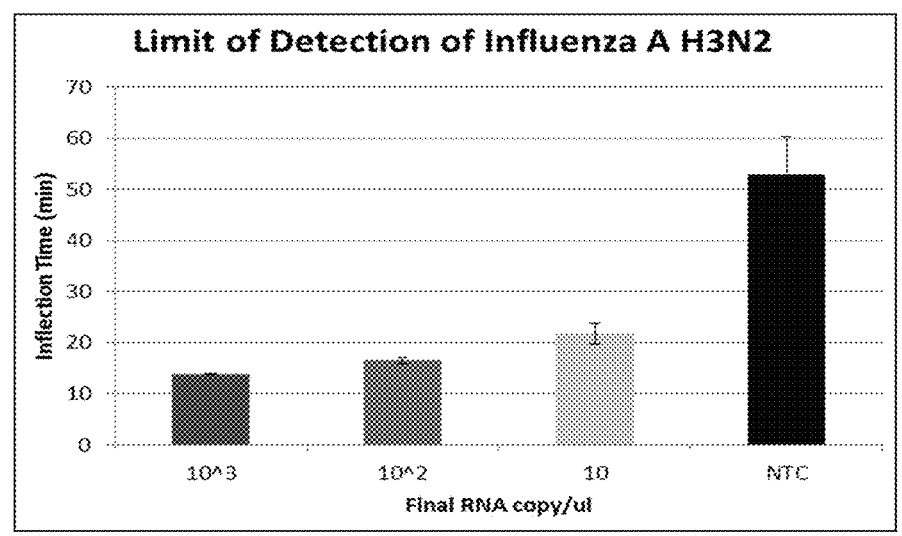
FIG. 4B shows the limit of detection of influenza A (H3N2 strain) in a sample. The height of the bars indicates the time until the copy number shows an inflection (rises significantly above the background level), with the horizontal axis indicating the initial numbers of copies of influenza A (H3N2 strain) message; "NTC" indicates "no template control" (no added copies of the target marker).
Figure 5A:
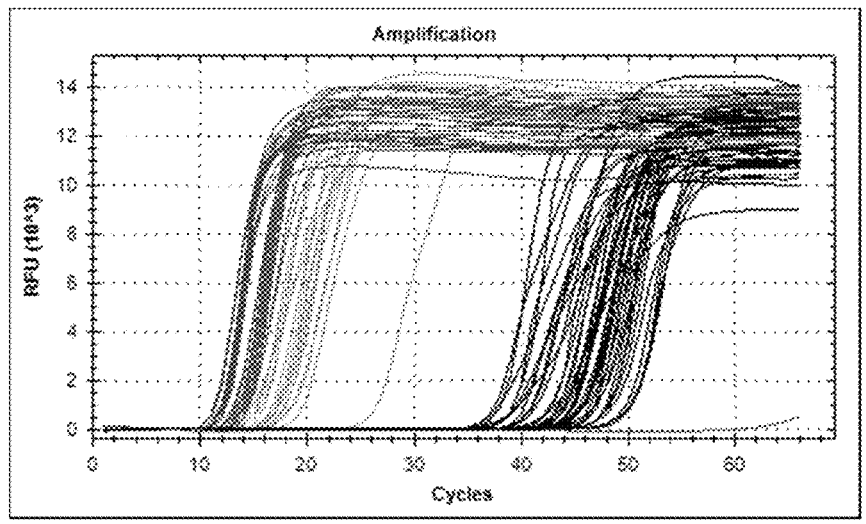
FIG. 5A shows amplification over time, showing detection of influenza A (H7N9 strain) marker at times well before any significant amounts of amplification of non-target nucleic acid message occurred. The horizontal axis is denominated in "cycles" although no cycling of temperature was used; each unit of "cycles" is approximately one minute, so that the numbers of the horizontal axis may be read in terms of minutes. The vertical axis is shown in units of relative fluorescence (relative fluorescence units, RFU), in thousands.
Figure 5B:
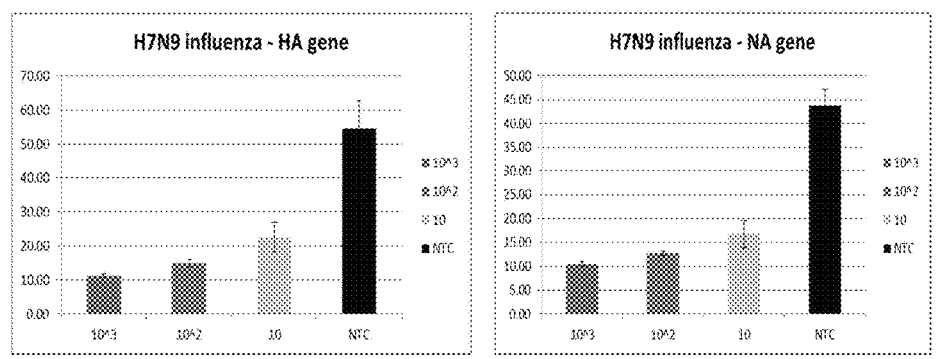
FIG. 5B shows the limit of detection of influenza A (H7N9 strain) in a sample. The height of the bars indicates the time until the copy number shows an inflection (rises significantly above the background level), with the horizontal axis indicating the initial numbers of copies of influenza A (H7N9 strain) message; "NTC" indicates "no template control" (no added copies of the target marker).
Figure 6A:
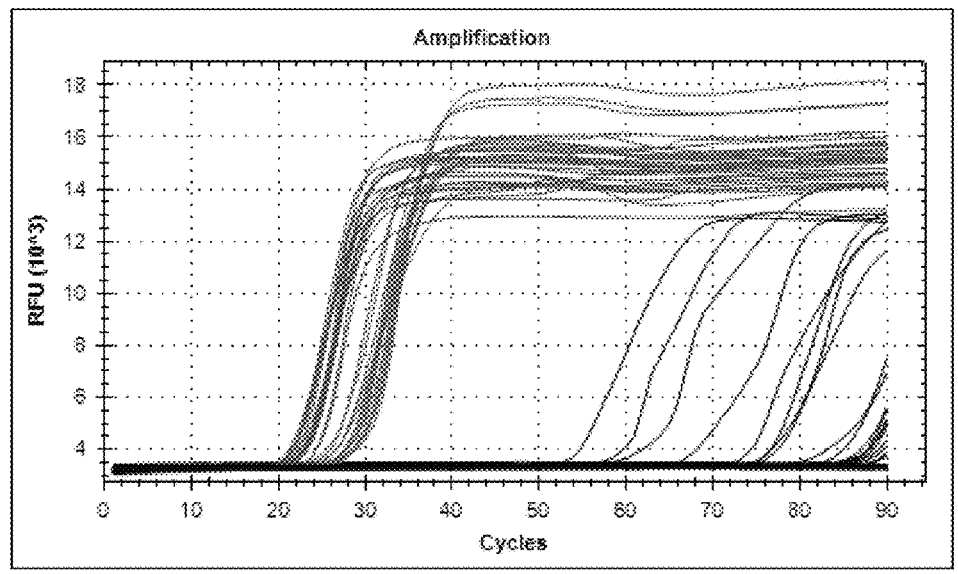
FIG. 6A shows amplification over time, showing detection of influenza A (H5N1 strain) marker at times well before any significant amounts of amplification of non-target nucleic acid message occurred. The horizontal axis is denominated in "cycles" although no cycling of temperature was used; each unit of "cycles" is approximately one minute, so that the numbers of the horizontal axis may be read in terms of minutes. The vertical axis is shown in units of relative fluorescence (relative fluorescence units, RFU), in thousands.
Figure 6B:
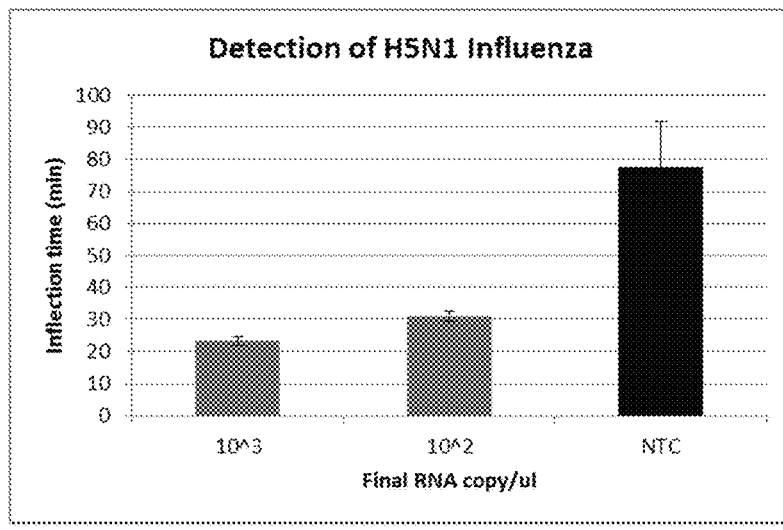
FIG. 6B shows the limit of detection of influenza A (H5N1 strain) in a sample. The height of the bars indicates the time until the copy number shows an inflection (rises significantly above the background level), with the horizontal axis indicating the initial numbers of copies of influenza A (H5N1 strain) message; "NTC" indicates "no template control" (no added copies of the target marker).
Figure 7A:
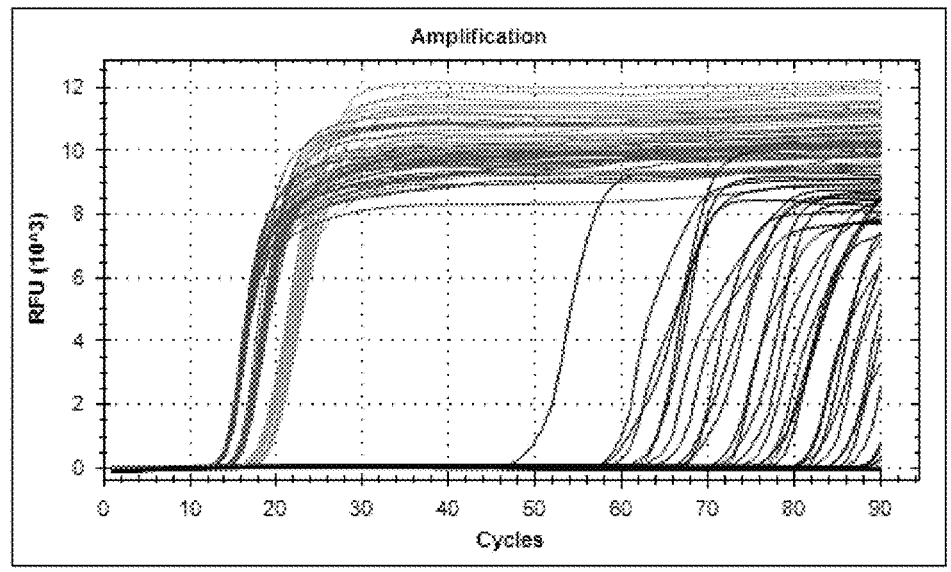
FIG. 7A shows amplification over time, showing detection of influenza B marker at times well before any significant amounts of amplification of non-target nucleic acid message occurred. The horizontal axis is denominated in "cycles" although no cycling of temperature was used; each unit of "cycles" is approximately one minute, so that the numbers of the horizontal axis may be read in terms of minutes. The vertical axis is shown in units of relative fluorescence (relative fluorescence units, RFU), in thousands.
Figure 7B:
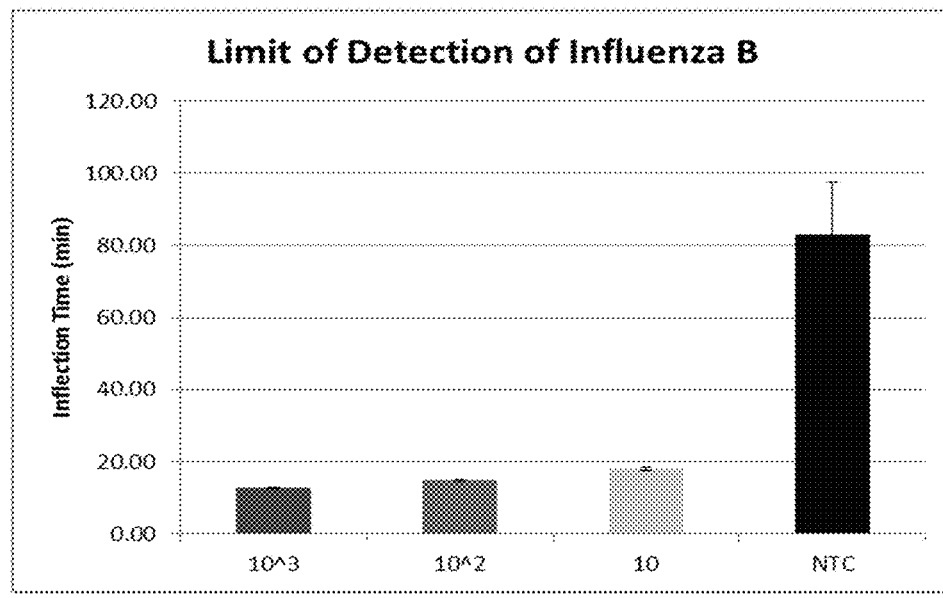
FIG. 7B shows the limit of detection of influenza B in a sample. The height of the bars indicates the time until the copy number shows an inflection (rises significantly above the background level), with the horizontal axis indicating the initial numbers of copies of influenza B message; "NTC" indicates "no template control" (no added copies of the target marker).
Figure 8A:
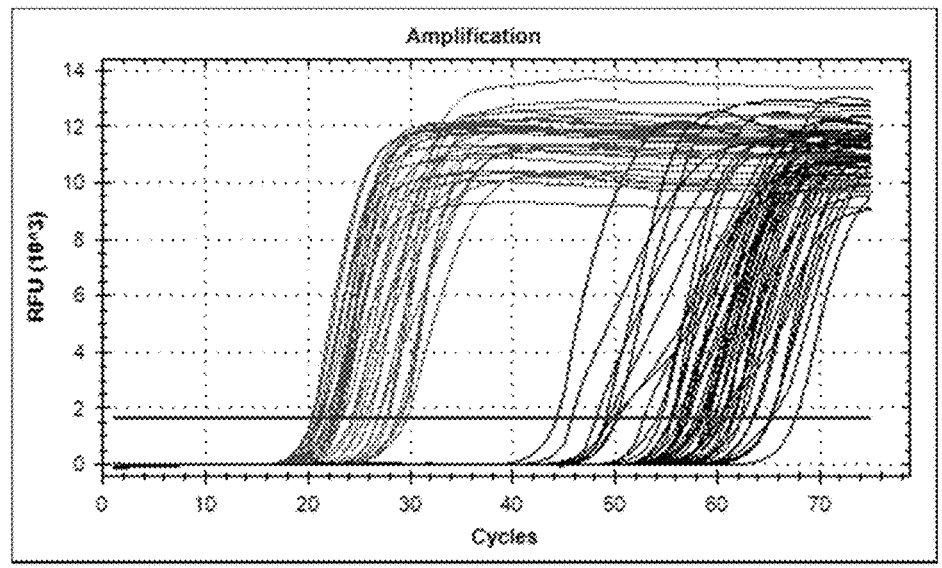
FIG. 8A shows amplification over time, showing detection of influenza Matrix Protein marker at times well before any significant amounts of amplification of non-target nucleic acid message occurred. The horizontal axis is denominated in "cycles" although no cycling of temperature was used; each unit of "cycles" is approximately one minute, so that the numbers of the horizontal axis may be read in terms of minutes. The vertical axis is shown in units of relative fluorescence (relative fluorescence units, RFU), in thousands.
Figure 8B:
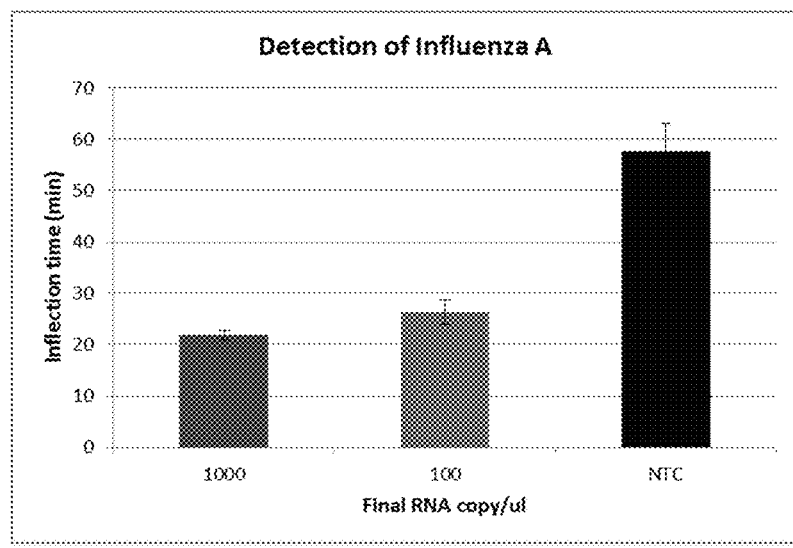
FIG. 8B shows the limit of detection of influenza Matrix Protein marker in a sample. The height of the bars indicates the time until the copy number shows an inflection (rises significantly above the background level), with the horizontal axis indicating the initial numbers of copies of influenza Matrix Protein message; "NTC" indicates "no template control" (no added copies of the target marker).
Figure 9A:
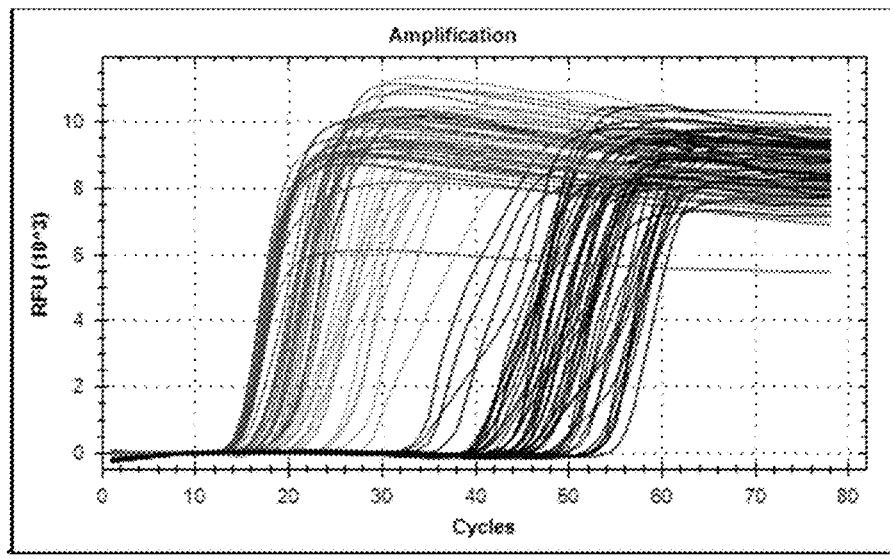
FIG. 9A shows amplification over time, showing detection of a tuberculosis marker (Myobacterium tuberculosis) at times well before any significant amounts of amplification of non-target nucleic acid message occurred. The horizontal axis is denominated in "cycles" although no cycling of temperature was used; each unit of "cycles" is approximately one minute, so that the numbers of the horizontal axis may be read in terms of minutes. The vertical axis is shown in units of relative fluorescence (relative fluorescence units, RFU), in thousands.
Figure 9B:
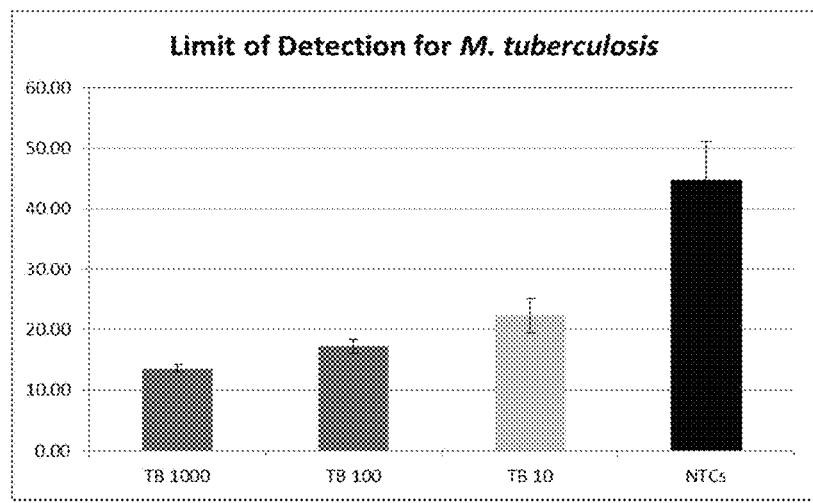
FIG. 9B shows the limit of detection of tuberculosis in a sample. The height of the bars indicates the time until the copy number shows an inflection (rises significantly above the background level), with the numbers "TB 1000" indicating 1000 copies of tuberculosis marker message, "TB 100" indicating 100 copies of tuberculosis marker message, and "TB 10" indicating 10 copies of tuberculosis marker message; "NTCs" indicates "no template controls" (no added copies of the target marker).
Figure 10A:
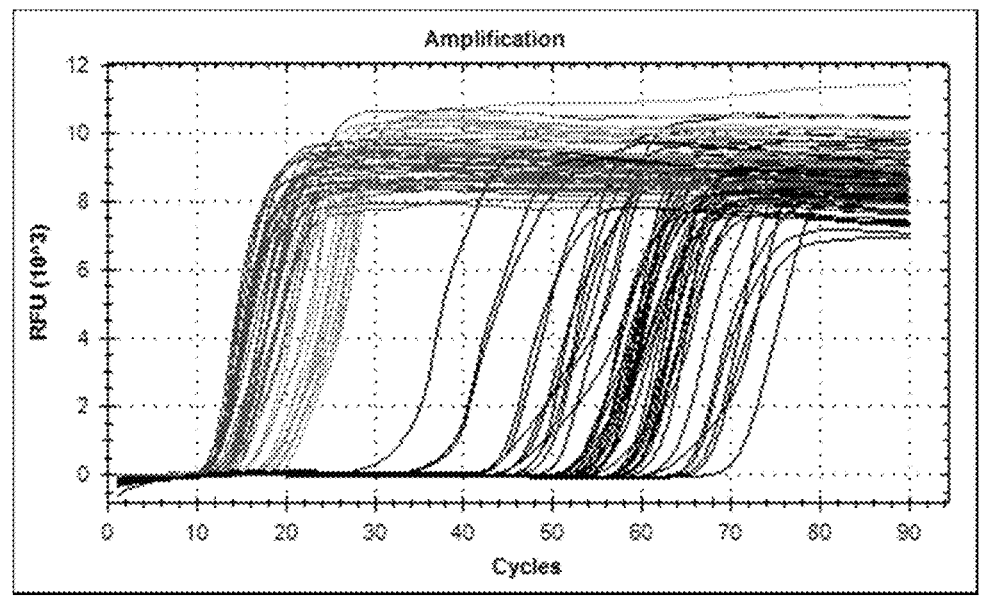
FIG. 10A shows amplification over time, showing detection of a staphyloccus marker (Staphylococcus aureus) at times well before any significant amounts of amplification of non-target nucleic acid message occurred. The horizontal axis is denominated in "cycles" although no cycling of temperature was used; each unit of "cycles" is approximately one minute, so that the numbers of the horizontal axis may be read in terms of minutes. The vertical axis is shown in units of relative fluorescence (relative fluorescence units, RFU), in thousands.
Figure 10B:
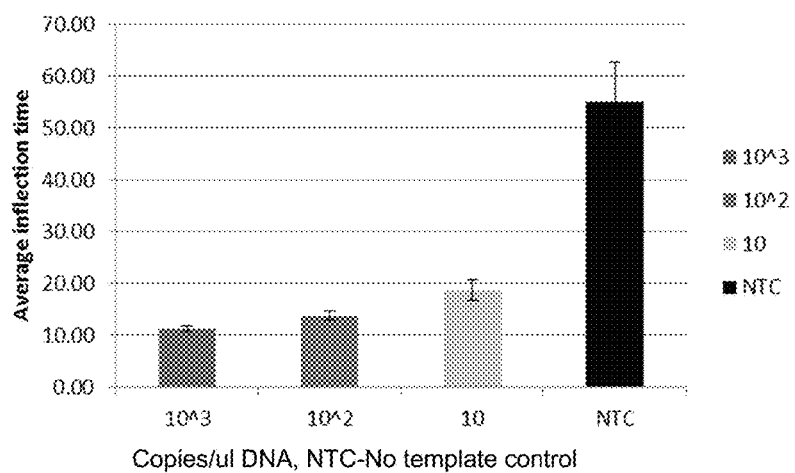
FIG. 10B shows the limit of detection of *Staphylococcus aureus* in a sample. The height of the bars indicates the time until the copy number shows an inflection (rises significantly above the background level), with the horizontal axis indicating numbers of copies of *Staphylococcus aureus* message; "NTC" indicates "no template control" (no added copies of the target marker).
Figure 11A:
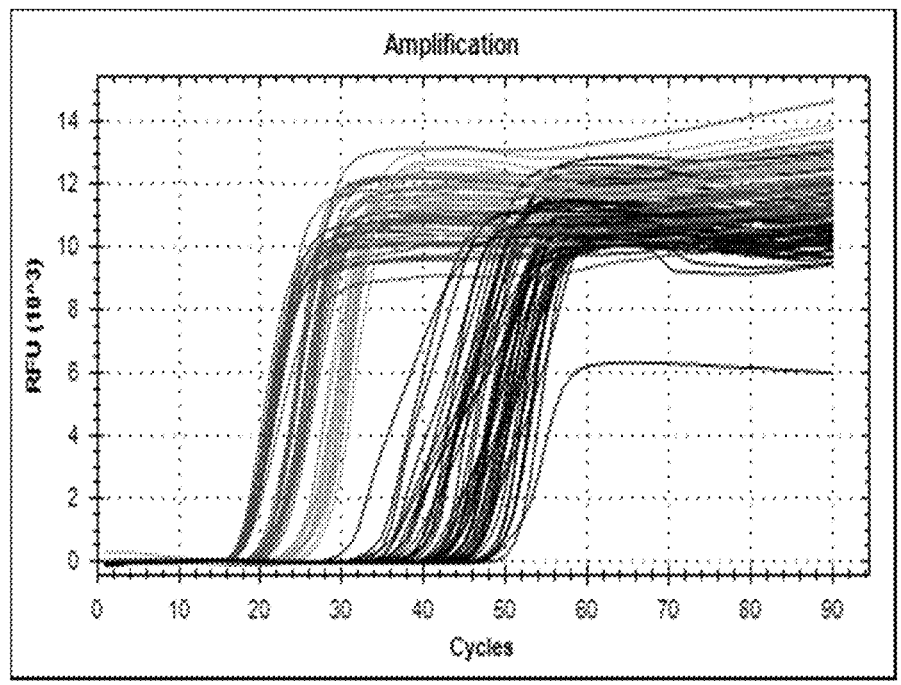
FIG. 11A shows amplification over time, showing detection of a staphyloccus marker (Methicillin-Resistant *Staphylococcus aureus*—MRSA) at times well before any significant amounts of amplification of non-target nucleic acid message occurred. The horizontal axis is denominated in "cycles" although no cycling of temperature was used; each unit of "cycles" is approximately one minute, so that the numbers of the horizontal axis may be read in terms of minutes. The vertical axis is shown in units of relative fluorescence (relative fluorescence units, RFU), in thousands.
Figure 11B:
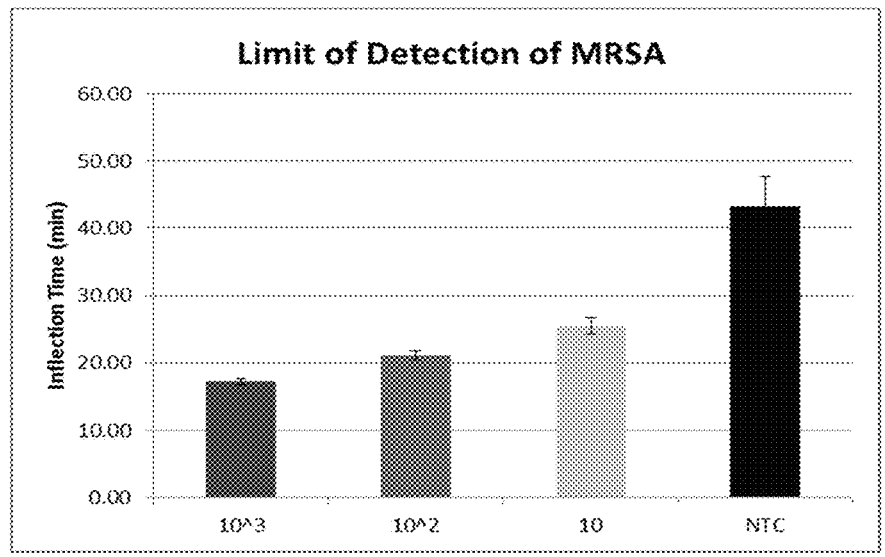
FIG. 11B shows the limit of detection of MRSA *Staphylococcus aureus* in a sample. The height of the bars indicates the time until the copy number shows an inflection (rises significantly above the background level), with the horizontal axis indicating numbers of copies of MRSA *Staphylococcus aureus* message; "NTC" indicates "no template control" (no added copies of the target marker).
Figure 12A:
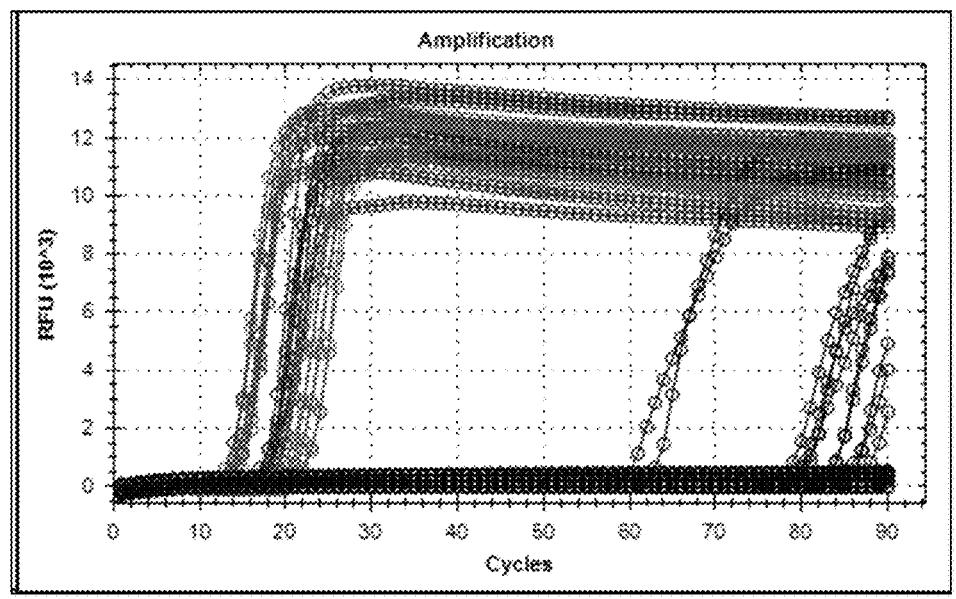
FIG. 12A shows amplification over time, showing detection of a streptococcus marker (Streptococcus Group A) at times well before any significant amounts of amplification of non-target nucleic acid message occurred. The horizontal axis is denominated in "cycles" although no cycling of temperature was used; each unit of "cycles" is approximately one minute, so that the numbers of the horizontal axis may be read in terms of minutes. The vertical axis is shown in units of relative fluorescence (relative fluorescence units, RFU), in thousands.
Figure 12B:
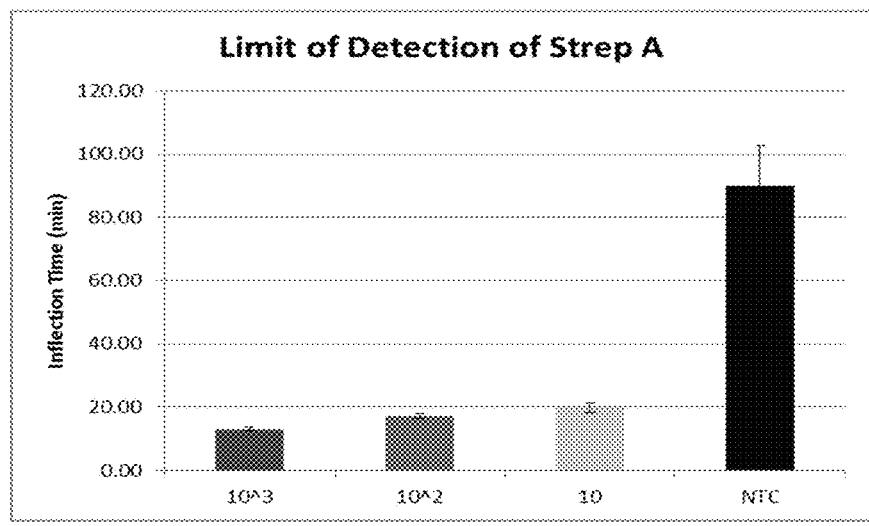
FIG. 12B shows the limit of detection of *Streptococcus* Group A in a sample. The height of the bars indicates the time until the copy number shows an inflection (rises significantly above the background level), with the horizontal axis indicating numbers of copies of *Streptococcus* Group A message; "NTC" indicates "no template control" (no added copies of the target marker).
Figure 13A:
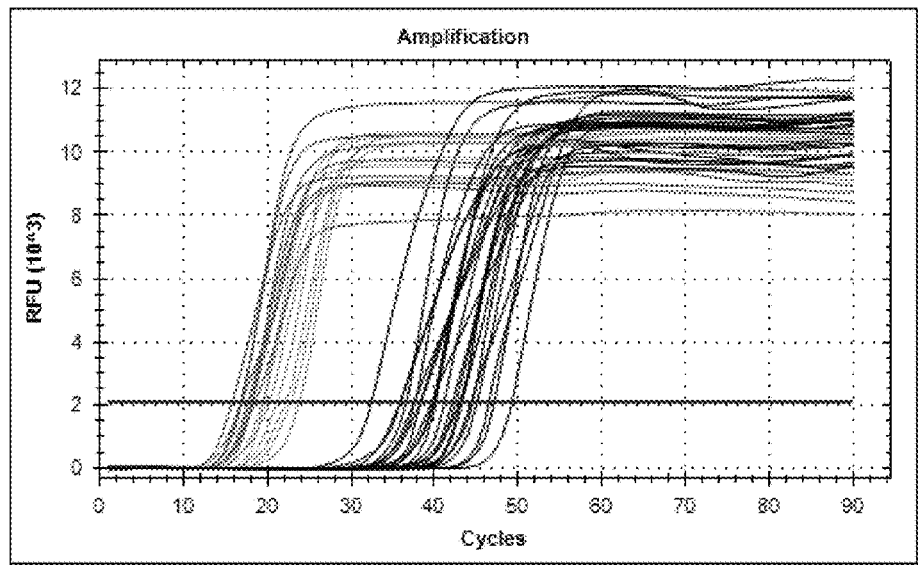
FIG. 13A shows amplification over time, showing detection of a *Bordetella pertussis* marker at times well before any significant amounts of amplification of non-target nucleic acid message occurred. The horizontal axis is denominated in "cycles" although no cycling of temperature was used; each unit of "cycles" is approximately one minute, so that the numbers of the horizontal axis may be read in terms of minutes. The vertical axis is shown in units of relative fluorescence (relative fluorescence units, RFU), in thousands.
Figure 13B:
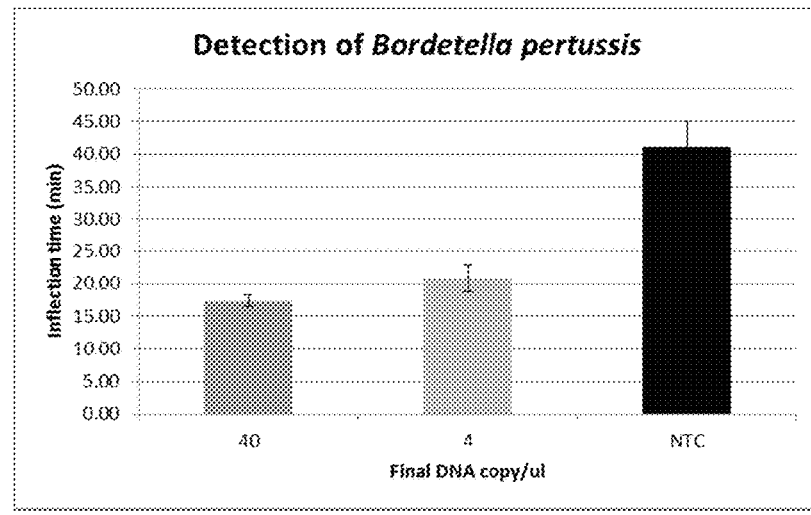
FIG. 13B shows detection of *Bordetella pertussis* in a sample. The height of the bars indicates the time until the copy number shows an inflection (rises significantly above the background level), with the horizontal axis indicating numbers of copies of *Bordetella pertussis* message (as final DNA copy per $\mu L$); "NTC" indicates "no template control" (no added copies of the target marker).
Figure 14A:
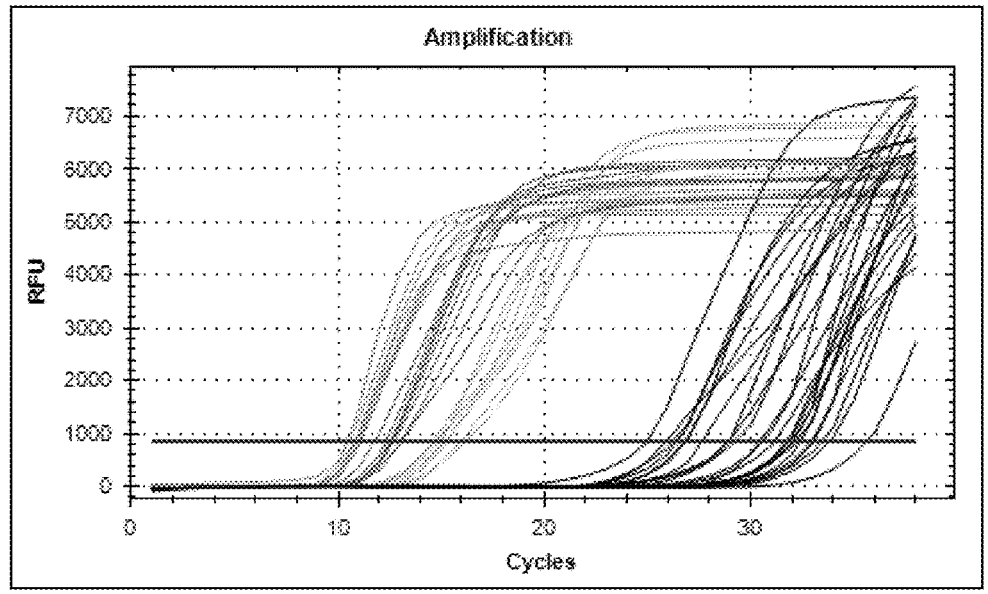
FIG. 14A shows amplification over time, showing detection of an adenovirus B marker at times well before any significant amounts of amplification of non-target nucleic acid message occurred. The horizontal axis is denominated in "cycles" although no cycling of temperature was used; each unit of "cycles" is approximately one minute, so that the numbers of the horizontal axis may be read in terms of minutes. The vertical axis is shown in units of relative fluorescence (relative fluorescence units, RFU), in thousands.
Figure 14B:
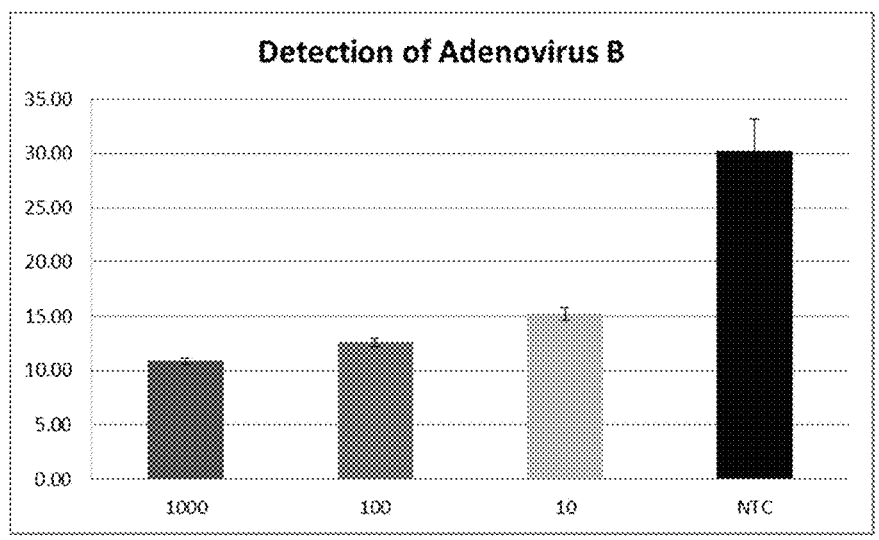
FIG. 14B shows the limit of detection of Adenovirus B in a sample. The height of the bars indicates the time until the copy number shows an inflection (rises significantly above the background level), with the horizontal axis indicating numbers of copies of Adenovirus B message; "NTC" indicates "no template control" (no added copies of the target marker).
Figure 15A:
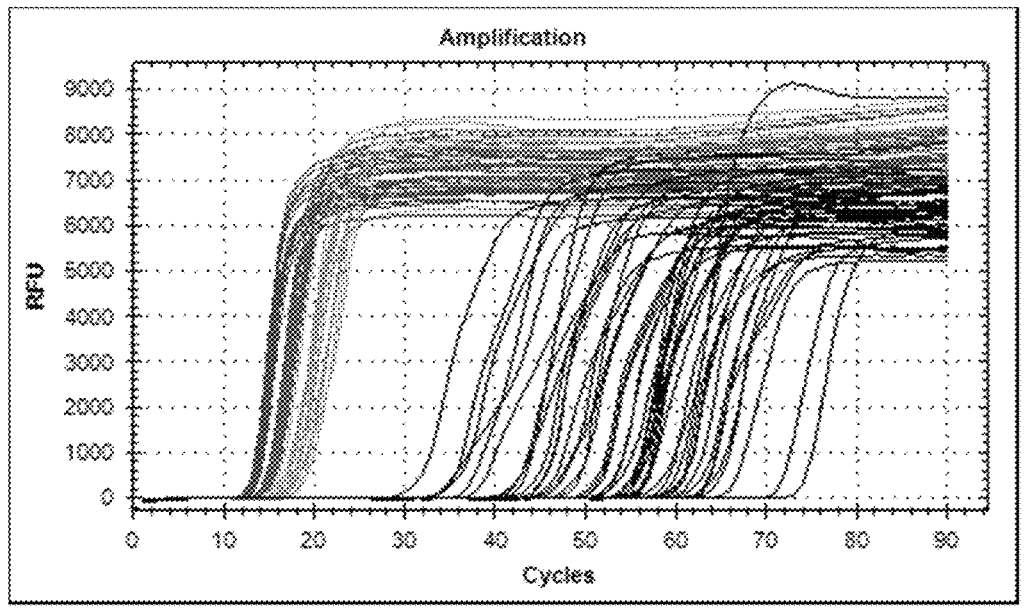
FIG. 15A shows amplification over time, showing detection of an adenovirus C marker at times well before any significant amounts of amplification of non-target nucleic acid message occurred. The horizontal axis is denominated in "cycles" although no cycling of temperature was used; each unit of "cycles" is approximately one minute, so that the numbers of the horizontal axis may be read in terms of minutes. The vertical axis is shown in units of relative fluorescence (relative fluorescence units, RFU), in thousands.
Figure 15B:
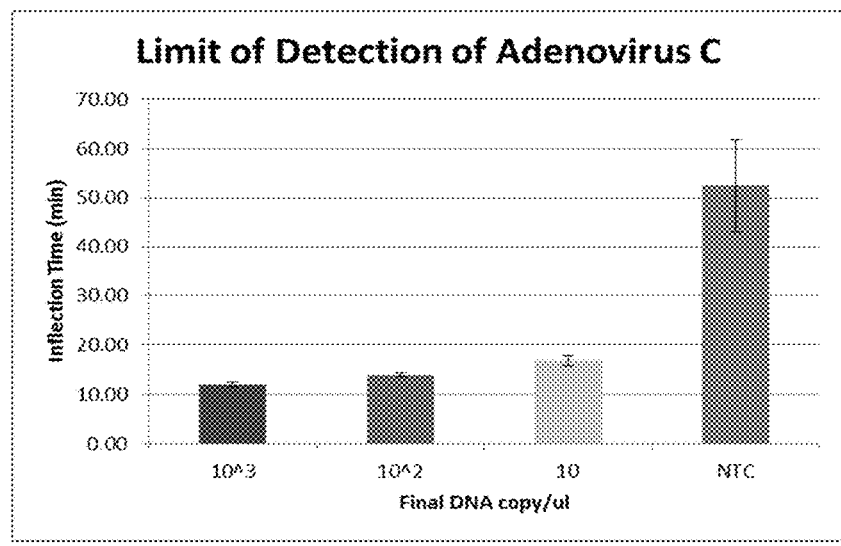
FIG. 15B shows the limit of detection of Adenovirus C in a sample. The height of the bars indicates the time until the copy number shows an inflection (rises significantly above the background level), with the horizontal axis indicating numbers of copies of Adenovirus C message; "NTC" indicates "no template control" (no added copies of the target marker).
Figure 16A:
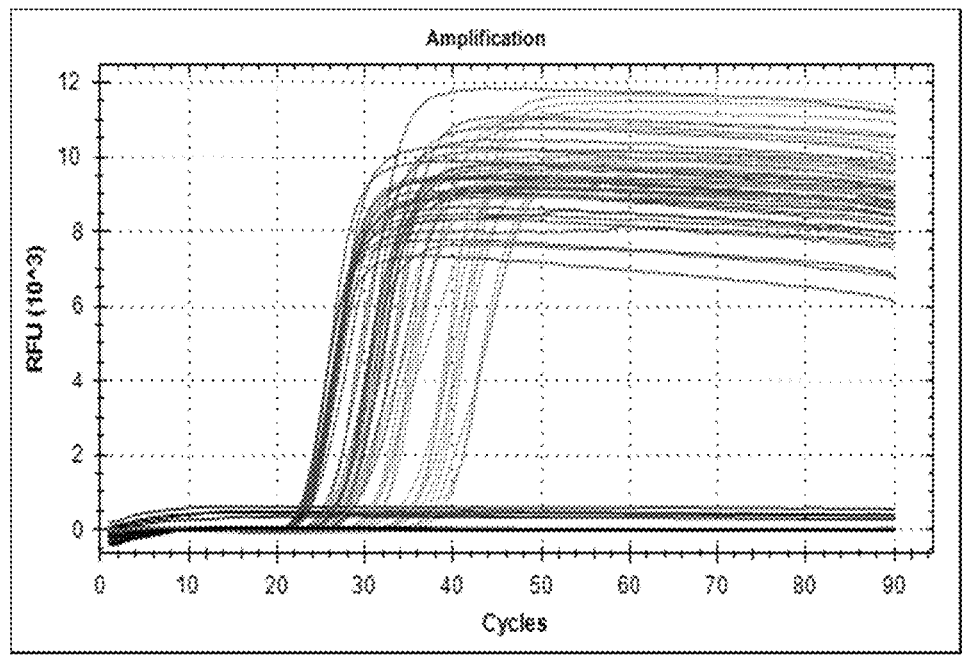
FIG. 16A shows amplification over time, showing detection of an adenovirus E marker at times well before any significant amounts of amplification of non-target nucleic acid message occurred. The horizontal axis is denominated in "cycles" although no cycling of temperature was used; each unit of "cycles" is approximately one minute, so that the numbers of the horizontal axis may be read in terms of minutes. The vertical axis is shown in units of relative fluorescence (relative fluorescence units, RFU), in thousands.
Figure 16B:
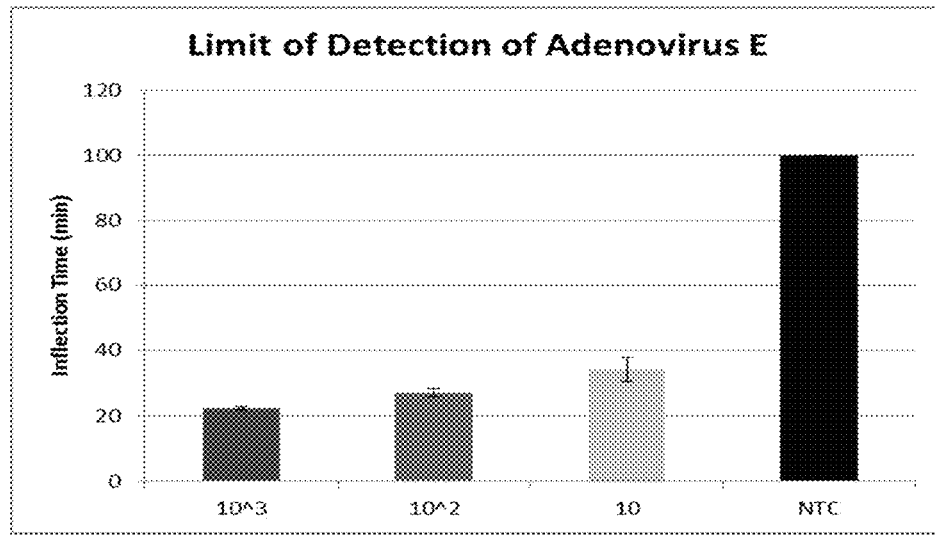
FIG. 16B shows the limit of detection of Adenovirus E in a sample. The height of the bars indicates the time until the copy number shows an inflection (rises significantly above the background level), with the horizontal axis indicating numbers of copies of Adenovirus E message; "NTC" indicates "no template control" (no added copies of the target marker).
Figure 17A:
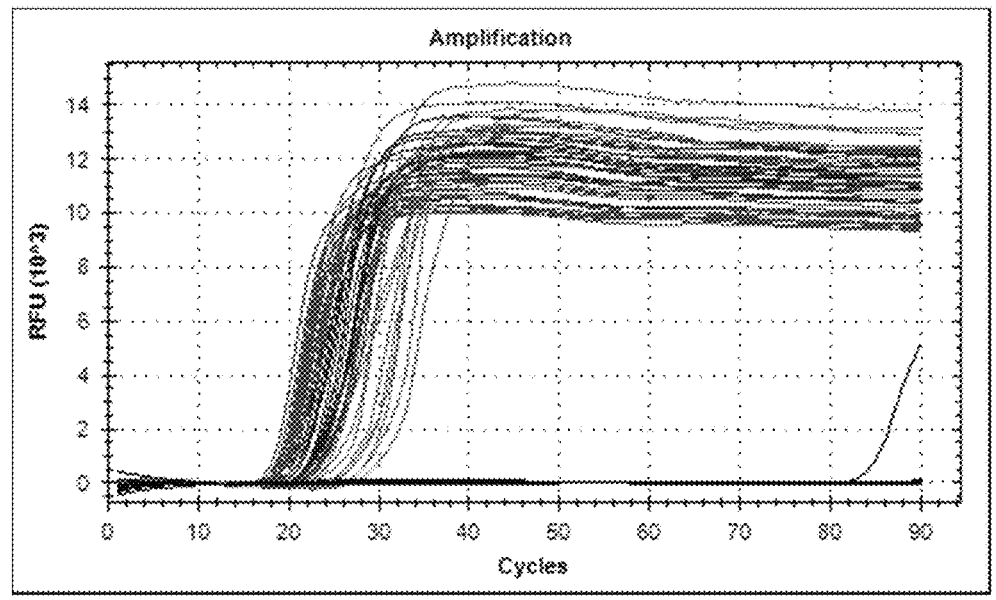
FIG. 17A shows amplification over time, showing detection of a Herpes Simplex Virus (HSV) marker at times well before any significant amounts of amplification of non-target nucleic acid message occurred. The horizontal axis is denominated in "cycles" although no cycling of temperature was used; each unit of "cycles" is approximately one minute, so that the numbers of the horizontal axis may be read in terms of minutes. The vertical axis is shown in units of relative fluorescence (relative fluorescence units, RFU), in thousands.
Figure 17B:
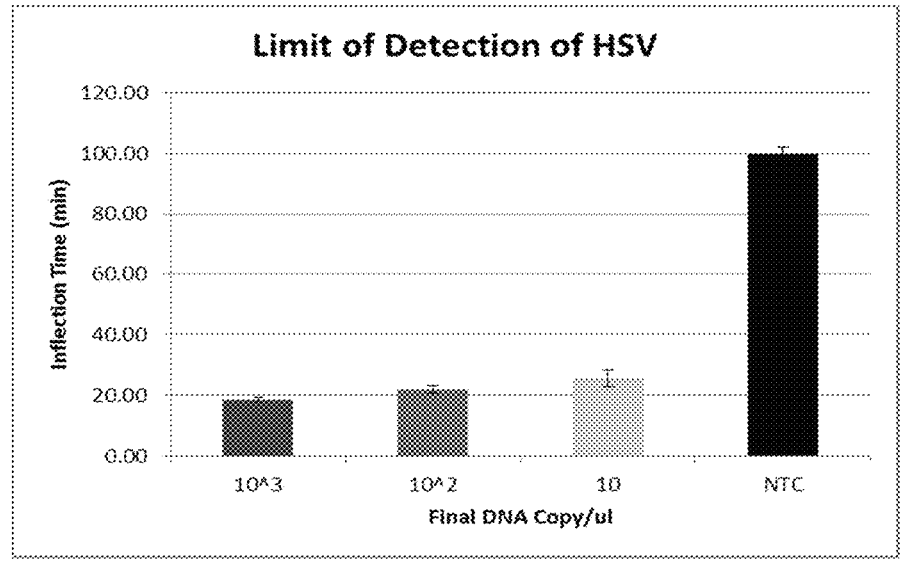
FIG. 17B shows the limit of detection of Herpes Simplex Virus (HSV) in a sample. The height of the bars indicates the time until the copy number shows an inflection (rises significantly above the background level), with the horizontal axis indicating numbers of copies of HSV message; "NTC" indicates "no template control" (no added copies of the target marker).
Figure 18A:
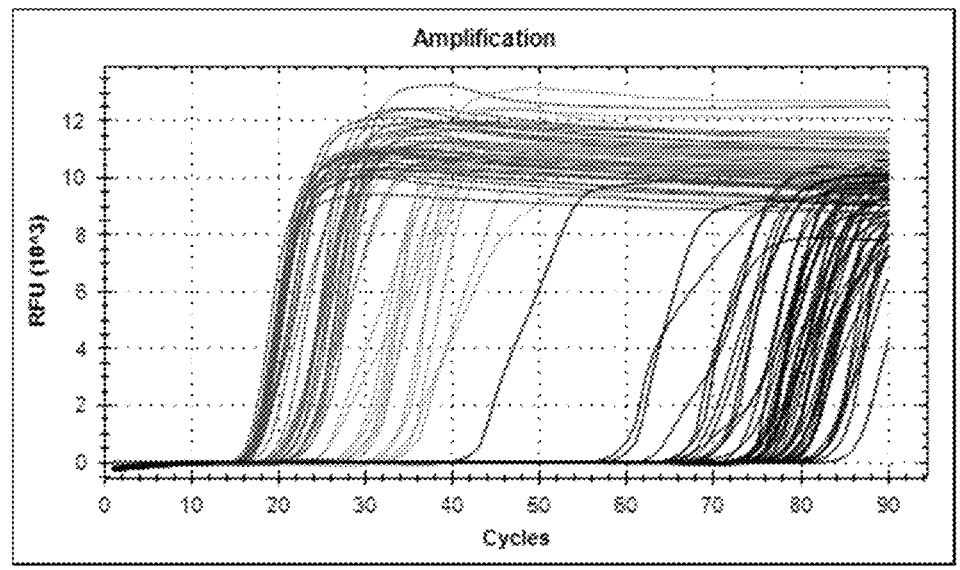
FIG. 18A shows amplification over time, showing detection of a *Treponema pallidum* marker at times well before any significant amounts of amplification of non-target nucleic acid message occurred. The horizontal axis is denominated in "cycles" although no cycling of temperature was used; each unit of "cycles" is approximately one minute, so that the numbers of the horizontal axis may be read in terms of minutes. The vertical axis is shown in units of relative fluorescence (relative fluorescence units, RFU), in thousands.
Figure 18B:
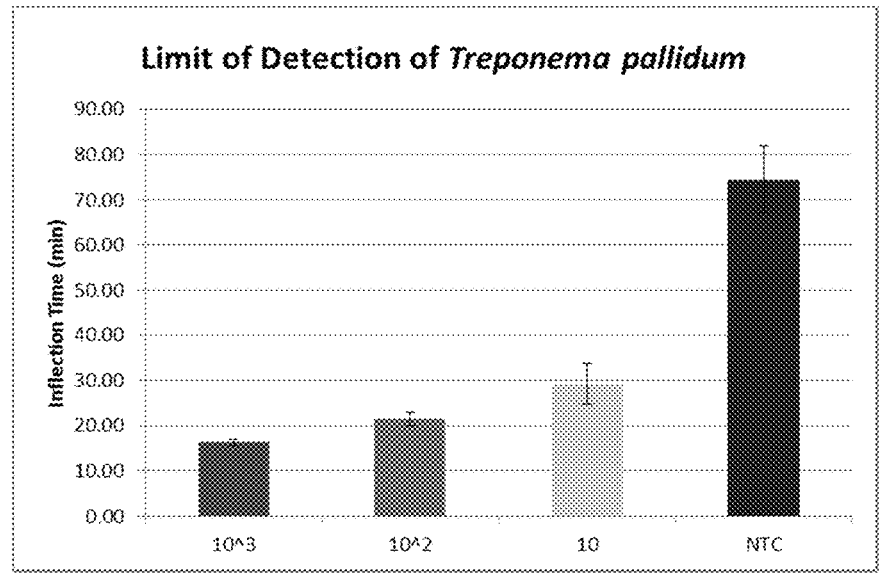
FIG. 18B shows the limit of detection of *Treponema pallidum* in a sample. The height of the bars indicates the time until the copy number shows an inflection (rises significantly above the background level), with the horizontal axis indicating numbers of copies of *Treponema pallidum* message; "NTC" indicates "no template control" (no added copies of the target marker).

These results were obtained by nucleic acid assays as described below and in U.S. Patent Application 61/800,606, filed Mar. 15, 2013. For example, the following results demonstrate testing for, and detection of, nucleic acid markers indicative of a variety of infectious diseases in a short period of time. As shown in the figures, many markers may be tested for, and may be detected. FIG. 2 shows results for detection of markers for influenza A (seasonal H1N1 strain). FIG. 3 shows results for detection of markers for influenza A (novel H1N1 strain). FIG. 4 shows results for detection of markers for influenza A (H3N2 strain). FIG. 5 shows results for detection of markers for influenza A (H7N9 strain). FIG. 6 shows results for detection of markers for influenza A (H5N1 strain). FIG. 7 shows results for detection of markers for influenza B. FIG. 8 shows results for detection of markers for influenza Matrix Protein. FIG. 9 shows results for markers for tuberculosis (Myobacterium tuberculosis). FIG. 10 shows results for markers for *staphylocccus* (*Staphylococcus aureus*). FIG. 11 shows results for markers for Methicilin-Resistant *Staphylococcus aureus* (MRSA). FIG. 12 shows results for markers for streptocccus (*Streptococcus* Group A). FIG. 13 shows results for markers for *Bordetella pertussis*. FIG. 14 shows results for markers for adenovirus B. FIG. 15 shows results for markers for adenovirus C. FIG. 16 shows results for markers for adenovirus E. FIG. 17 shows results for markers for Herpes Simplex Virus (HSV). FIG. 18 shows results for markers for *Treponema pallidum*.

Samples obtained from subjects, including small samples from subjects, may be tested for other diseases in addition to the diseases listed in the figures and in Table 2A. For example, some other diseases which may be tested for by these methods are listed in Table 2B. The column labeled "Panel" indicates the type of disease (where HAI indicates Hospital Acquired Infection, and STD indicates sexually transmitted disease).

TABLE 2B

| # | Assay | Panel |
|---|---|---|
| 1 | *Acinetobacter baumannii* | HAI |
| 2 | *Bordetella parapertussis* | Respiratory |
| 3 | *Chlamydophila pneumoniae* | Respiratory |
| 4 | RSV A | Respiratory |
| 5 | *Enterobacter aerogenes* | HAI |
| 6 | Hepatitis C | STD |
| 7 | *Enterobacter cloacae* | HAI |
| 8 | *H. influenzae* blaTEM | HAI |
| 9 | *Legionella pneumophila* | HAI |
| 10 | *Serratia marcescens* | HAI |
| 11 | Metapneumovirus B | Respiratory |
| 12 | *Pseudomonas aeruginosa* | HAI |
| 13 | Parainfluenza 4a | Respiratory |
| 14 | Parainfluenza 4b | Respiratory |
| 15 | West Nile Virus 1 | Respiratory |
| 16 | Penicillin-resistant *S. pneumo* | Respiratory |
| 17 | HIV-1 group O | STD |
| 18 | *H. influenzae* blaROB | HAI |
| 19 | RSV B | Respiratory |
| 20 | Rhinovirus A | Respiratory |
| 21 | Rhinovirus B | Respiratory |
| 22 | Rhinovirus C | Respiratory |

The systems, methods, and devices disclosed herein may be used to test for, and to detect, the presence of markers indicative of one or more of the infectious agents listed above; such testing, and such detecting, may be performed on a single clinical sample, or on a plurality of aliquots of a single clinical sample. Such a single clinical sample may be a single small-volume clinical sample. Such testing, and detecting, may be performed at a POS location; the systems, devices and methods may be POS systems, device, and methods. For example, the clinical sample may be collected at the POS location, and may be analyzed in a device at the POS location. As shown in the results illustrated in the Figures, the analysis of the small-volume clinical sample may be completed in a short period of time.

Thus, the following are some of the disease-causing agents may be tested for, and may be detected, according to the methods, and by the systems and devices, as disclosed herein.

TABLE 3

Disease-Causing Agents and Markers Therefor

Influenza A Matrix protein
Influenza H3N2
Influenza H1N1 seasonal
Influenza H1N1 novel TABLE 3-continued Disease-Causing Agents and Markers Therefor Influenza B
*Streptococcus pyogenes* (A)
*Mycobacterium Tuberculosis*
*Staphylococcus aureus* (MR)
*Staphylococcus aureus* (RS)
*Bordetella pertussis* (whooping cough)
*Streptococcus agalactiae* (B)
Influenza H5N1
Influenza H7N9
Adenovirus B
Adenovirus C
Adenovirus E
Hepatitis b
Hepatitis c
Hepatitis delta
*Treponema pallidum*
HSV-1, HSV-2
HIV-1
HIV-2
Human RNaseP (sample prep control)
Dengue 1
Dengue 2
Dengue 3
Dengue 4
Malaria
West Nile Virus
*Trypanosoma cruzi* (Chagas)
*Klebsiella pneumoniae* (Enterobacteriaceae spp)
*Klebsiella pneumoniae* carbapenemase (KPC)
Epstein Barr Virus (mono)
Rhinovirus
Parainfluenza virus (1)
Parainfluenza virus (2)
Parainfluenza virus (3)
Parainfluenza virus (4a)
Parainfluenza virus (4b)
Respiratory syncytial virus (RSV) A
Respiratory syncytial virus (RSV) B
Coronavirus 229E
Coronavirus HKU1
Coronavirus OC43
Coronavirus NL63
Novel Coronavirus
Bocavirus
human metapneumovirus (HMPV)
*Streptococcus pneumoniae* (penic R)
*Streptococcus pneumoniae* (S)
*Mycoplasma pneumoniae*
*Chlamydia pneumoniae*
*Bordetella parpertussis*
*Haemophilus influenzae* (ampic R)
*Haemophilus influenzae* (ampic S)
*Moraxella catarrhalis*
*Pseudomonas* spp (*aeruginosa*)
*Haemophilus parainfluenzae*
*Enterobacter cloacae* (Enterobacteriaceae spp)
*Enterobacter aerogenes* (Enterobacteriaceae spp)
*Serratia marcescens* (Enterobacteriaceae spp)
*Acinetobacter baumanii*
*Legionella* spp
*Escherichia coli*
Candida
*Chlamydia trachomatis*
HPV
*Neisseria gonorrhoeae*
*Trichomonas* (vagin)

The disease-causing agents listed in Table 3 may be tested for, and may be detected, by the methods, and using the systems and devices disclosed herein. For example, markers for the disease-causing agents listed in Table 3 may be tested for, and may be detected, by the methods, and using the systems and devices disclosed herein. Such markers may include, for example, nucleic acid markers. In addition, such markers may include saccharide markers, or other markers, such as, e.g., protein markers. Methods of testing for, and of detecting, protein markers are discussed in the following example.

EXAMPLE 2

Detection of Influenza Virus from 2 μL of Prepared Sample

Figure 19A:
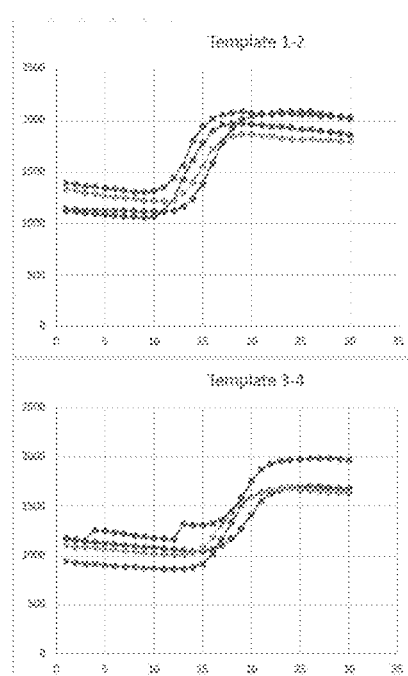
FIG. 19A shows amplification over time, the rise in relative fluorescence at about 15 to 20 minutes indicating the presence of an Influenza H1N1 seasonal marker. The horizontal axis is in "minutes; the vertical axis is shown in units of relative fluorescence (relative fluorescence units, RFU).

Detection of nucleic acid from 2 μL of sample taken from cultured cells infected with seasonal influenza virus (H1N1) is shown in FIGS. 19A (sample) and 19B (control). Nucleic acid obtained from the cell cultures was prepared using the Chemagic magnetic separator module I with DWP 24 XL adapters and reagents from the Chemagic Viral DNA/RNA Kit (No. CMG-1089; No. CMG-1082 is similar) from Chemagen (PerkinElmer chemagen Technologie Gmbh, Baesweller, Germany)). This method uses magnetic bead separation to isolate RNA and DNA from a sample. Chemagen reagents and disposables were used in preparing the samples.

H1N1 influenza RNA was obtained from cultured infected MDCK cells. Briefly, cell culture samples were prepared by dispensing approximately 1 mL of sample solution into a well containing lysis buffer, poly(A) RNA reagent, and proteinase K solutions with gentle mixing. The wells were covered and heated at 55° C. for ten minutes. Following this ten minute incubation, binding buffer was added to the wells containing the lysed sample solution. This mixed solution was then processed by the Chemagic magnetic separator module I. Nucleic acids were released by vortexing (rotation of probes) in the buffer and then bound to the magnetic beads, which were immobilized by a magnet during wash steps. The nucleic acids freed in the sample bound to the beads and were retained during wash steps; following the wash steps, the nucleic acids were eluted into elution buffer (10 mM TRIS-HCl, pH 8.0).

Following this sample preparation, the prepared sample was placed in a container held in a cartridge, and the cartridge was loaded on an automatic sample analysis device (such cartridges, devices, and their uses are described, for example, in U.S. Pat. Nos. 8,088,593; 8,380,541; U.S. patent application Ser. No. 13/769,798, filed Feb. 18, 2013; U.S. patent application Ser. No. 13/769,779, filed Feb. 18, 2013; U.S. patent application Ser. No. 13/769,820, filed Feb. 18, 2013; PCT/US2012/57155, filed Sep. 25, 2012; U.S. patent application Ser. No. 13/244,949, filed Sep. 26, 2011; U.S. Application Ser. No. 61/800,606, filed Mar. 15, 2013; U.S. Application Ser. No. 61/766,095, filed Feb. 18, 2013; and U.S. Application Ser. No. 61/673,245, filed Jul. 18, 2012; U.S. Patent Application 61/805,923, filed Mar. 27, 2013, hereby incorporated by reference in their entireties).

A 2 μL aliquot of the prepared sample solution was placed in a vessel containing 20 μL of MasterMix (containing buffer, betaine, dNTPs, forward (RLX1222) and reverse (RLX1223) probes, Syto 59 Red dye), and mixed with 3 μL of enzyme preparation (containing *B. stearothermophilus* DNA polymerase (Bst), Avian Myeloblastosis Virus Reverse Transcriptase (AmvRT), NEB4 buffer (New England Biolabs Cat. No. B7004S), and water) in a reaction vessel in the automatic sample analysis device. Primers specific for H1N1 influenza virus were included in the mixture in the reaction vessel. The combination of sample, MasterMix, template, and enzyme preparation was incubated at 56° C. in the reaction vessel according to the methods discussed above, and fluorescence was measured every minute for 30 minutes (fluorescence was from SYTO 59 dye). The fluorescence was read as relative fluorescence.

FIG. 19A shows amplification over time, the rise in relative fluorescence at about 15 to 20 minutes indicating the presence of an Influenza H1N1 seasonal marker. The horizontal axis is in "minutes; the vertical axis is shown in units of relative fluorescence (relative fluorescence units, RFU).

Figure 19B:
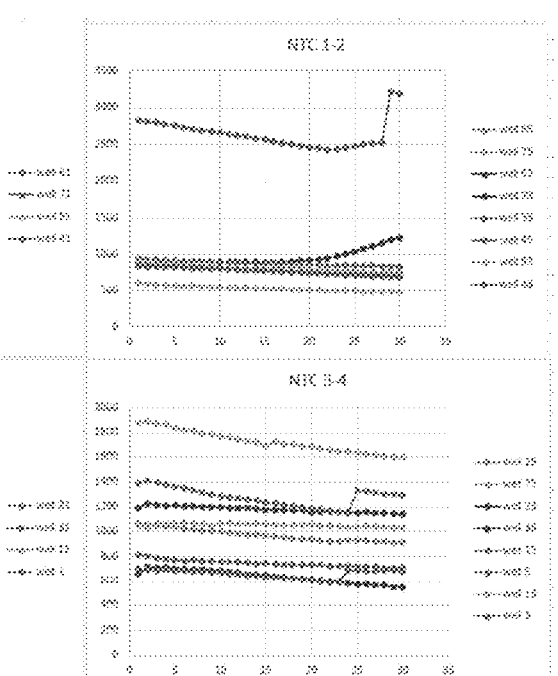
FIG. 19B shows amplification of "no template control" (no added copies of the target marker; NTC). Note that most experiments showed no amplification; the three runs that show late increases in relative fluorescence did so at about 25 minutes or later. The horizontal axis is in "minutes; the vertical axis is shown in units of relative fluorescence (relative fluorescence units, RFU).

FIG. 19B shows amplification of "no template control" (no added copies of the target marker; NTC). Note that most experiments showed no amplification; the three runs that show late increases in relative fluorescence did so at about 25 minutes or later. The horizontal axis is in "minutes; the vertical axis is shown in units of relative fluorescence (relative fluorescence units, RFU).

The results from FIGS. 19A and 19B show that viral nucleic acid can be detected from small volume samples (e.g., 2μL of sample) within a short amount of time (e.g., about 15 to 20 minutes or less).

EXAMPLE 3

Detection of Influenza Virus Proteins by ELISA

Detection of proteins indicative of Influenza A infection and proteins indicative of Influenza B infection was accomplished using devices and systems as described, for example, in U.S. Pat. Nos. 8,088,593; 8,380,541; U.S. patent application Ser. No. 13/769,798, filed Feb. 18, 2013; U.S. patent application Ser. No. 13/769,779, filed Feb. 18, 2013; U.S. patent application Ser. No. 13/769,820, filed Feb. 18, 2013; PCT/US2012/57155, filed Sep. 25, 2012; U.S. patent application Ser. No. 13/244,949, filed Sep. 26, 2011; U.S. Application Ser. No. 61/800,606, filed Mar. 15, 2013; U.S. Application Ser. No. 61/766,095, filed Feb. 18, 2013; and U.S. Application Ser. No. 61/673,245, filed Sep. 26, 2011; U.S. Patent Application 61/805,923, filed Mar. 27, 2013 (references that were previously listed and incorporated by reference in their entireties in text above). Unless otherwise stated below (e.g., with regard to results obtained with commercial systems for comparison) such devices and systems were used to obtain the data presented below.

Assay Design and Purpose: The assays for Influenza A and Influenza B were designed to provide qualitative detection of Influenza A or Influenza B nucleoprotein antigens in a sample obtained with a nasal swab. These assays are useful in the diagnosis of Influenza A viral infections or Influenza B viral infections in a subject from whom the sample was obtained. The assay was a sandwich assay, in which anti-Influenza A or B antibodies were immobilized on a substrate (the interior of a translucent or transparent pipette tip), and sample, alkaline phosphatase (ALP)-conjugated anti-Influenza A or B antibody, and ALP substrate added to produce chemiluminescence proportional to the amount of Influenza antigen in the sample. The assay results were compared to those of a commercial test (the Remel X/pect Influenza A & B; Remel Products, Lenexa, Kans., USA, a division of Thermo Fisher Scientific, Inc.).

Materials and Methods: The interior of a custom polymer pipette tip served as the surface for this sandwich ELISA assay. The pipette tips were typically made from polystyrene or polypropylene, although other polymers or plastic materials are also suitable. The pipette tip interiors were coated with avidin. The capture surface for the sandwich ELISA was prepared by coating biotin-labeled anti-Influenza A antibody or biotin-labeled anti-Influenza B antibody onto the avidin-coated interior surfaces of the pipettes.

Capture and detection antibodies were obtained from United States Biological Corporation (Salem, Mass., USA) or SouthernBiotech (SouthernBiotechnology Associates, Inc., Birmingham, Ala., USA); capture antibodies were conjugated with biotin using a biotin labeling kit, and detection antibodies were conjugated with ALP using a ALP labeling kit, both from Dojindo Molecular Technologies, Inc. (Rockville, Md., USA). Buffers were obtained from Sigma Aldrich Corporation (St. Louis, Mo., USA).

Samples were obtained from the nasal passages of subjects using nasal swabs. Nasal swabs containing sample material were then subjected to an extraction process. ALP-labeled anti-influenza A or ALP-labeled anti-influenza B antibodies were then mixed with the extracted sample material. This mixture was then incubated with the capture surface for 5 minutes. After the incubation, the capture surface was washed and ALP substrate was incubated on the surface for 5 minutes; the resulting chemiluminescence intensity was then read, with results reported in Relative Light Units (RLU).

Buffers: TRIS-buffered Saline consisted of 138 mM NaCl, 2.7 mM KCl, and 0.05 M tris(hydroxymethyl)aminomethane (TRIS), pH 8.

The extraction buffer was 0.5% Tween 20, 0.1% sodium azide in 20 mM sodium phosphate buffer (pH 7.6).

The blocking buffer was 3% BSA blocking buffer, consisting of TRIS-buffered Saline, 3% BSA, 0.05% $NaN_3$, at pH 8.

The alkaline phosphatase (AP) stabilizer was prepared by adding 0.1 mM zinc chloride and 5 mM magnesium chloride to the 3% BSA blocking buffer.

The wash buffer was TRIS-buffered Saline, 0.05% Tween 20, 0.05% $NaN_3$, at pH 8.

Influenza A and Influenza B Antibody Screen: Various permutations of pairs of Influenza A or Influenza B antibodies, consisting of paired capture antibodies (CAbs) and detection antibodies (DAbs), were tested on microtitre plates in order to identify the best-performing pairs. A volume of 50 µl of sample was added to 400 µl of extraction buffer for these experiments. The conditions included 5 µg/mL of CAb and 100 ng/mL (final concentration) of DAb in blocking buffer. Positive and negative controls were from kits obtained from either Microbix Biosystems, Inc. (Mississauga, Ontario, Canada) or the Virusys Corporation (Taneytown, Md., USA). The best pairs from the microtitre plate screening experiments were then evaluated on the devices and systems disclosed herein, as discussed in the following paragraphs.

Capture Surface Titration: The capture surface was titrated at the following concentrations: 10 µg/ml, 5 µg/ml, and 1 µg/ml. Controls from the Virusys kit and Microbix kit were used for this screening. The background control was a blocking buffer blank with no added sample. The DAb was maintained at a concentration of 100 ng/ml (final concentration in blocking buffer). The optimal CAb concentration was determined to be 5 µg/ml for both Influenza A and Influenza B.

Alkaline Phosphatase Stabilizer: Two alkaline phosphatase stabilizers were tested for use as DAb diluents. In these experiments, 50 µl of sample was added to 500 µl of extraction buffer. The CAb concentration was 5 µg/ml while the DAb concentration was maintained at 100 ng/ml (final concentration after the protocol run). Both the custom AP stabilizer solution (ingredients listed above) and the commercial Stabilzyme® AP conjugate stabilizer (SurModics, Inc., Eden Prairie, Minn., USA) worked well. The custom AP stabilizer was used in subsequent experiments.

Detection Antibody Titration: The AP-conjugated DAbs were titrated in the AP stabilizer solution. The best modulation between the positive and negative controls was observed at 50 ng/ml final concentration. The Influenza A positive controls were obtained from Microbix Biosystems, Inc. and ZeptoMetrix Corporation (Buffalo, N.Y., USA), and the Influenza B positive controls were obtained from Microbix Biosystems, Inc. and Virusys Corporation.

Specificity Tests—Influenza A: Specificity and cross reactivity studies were performed in extraction buffer using the sample processing and analysis devices and systems as disclosed herein. Controls for testing for potential cross-reactants were obtained from Microbix Biosystems, Inc. The potential cross-reactants tested were Respiratory Syncytial Virus, *Mycoplasma pneumonia*, Adenovirus, Parainfluenza A-III, Parainfluenza A-II and Parainfluenza A-I. CAb concentration was 5 µg/ml while DAb concentration was 100 ng/ml (final concentration after protocol run). No cross-reactivity was detected in these experiments. Different strains of Influenza A and Influenza B were also tested to determine the Influenza A specificity in the assay. Both Zeptometrix and Microbix controls (which are prediluted controls) were used for this test. Positive Influenza A control swabs from the Remel Xpect Flu kit were also used. A sample volume of 200 µl was mixed with 200 µl of extraction buffer and tested for these prediluted samples. Swabs were processed using 400 µl of extraction buffer for these experiments. In the following tables, relative light unit (RLU) measurements were made in triplicate; "CV %" is calculated by dividing the standard deviation of the three measurements by the mean of the three measurements and multiplying by 100.

TABLE 4

Specificity Tests - Influenza A

| Sample Type | Sample | Mean RLU | CV % |
|---|---|---|---|
| Microbix POS CTL | Influenza A | 127832 | 25.7 |
| Zeptometrix-POS CTL | Influenza A | 24235 | 10.3 |
| Swab-Remel (FDA) | Influenza A | 269726 | 11.2 |
| Zeptometrix-Influenza A Strain | Brisbane/59/07 | 202118 | 10.8 |
| Zeptometrix-Influenza A Strain | Brisbane/10/07 | 60655 | 14.2 |
| Zeptometrix-Influenza A Strain | Perth/16/2009 | 36571 | 14.0 |
| Zeptometrix-Influenza A Strain | Solomon Islands/03/2006 | 91428 | 11.8 |
| Virusys | 250 ng/ml of Influenza A | 439907 | 16.3 |
|  | Mean Positive | 156559 |  |
| Microbix | Respiratory Syncytial Virus | 1744 | 21.3 |
| Microbix | *Mycoplasma pneumoniae* | 1798 | 23.2 |
| Microbix | Adenovirus | 1954 | 24.7 |
| Microbix | Parainfluenza A-III | 2162 | 22.0 |
| Microbix | Parainfluenza A-II | 2110 | 25.2 |
| Microbix | Parainfluenza A -I | 2108 | 20.3 |
| Microbix NEG CTL | Influenza A/B Negative | 2072 | 28.0 |
| Zeptometrix-Influenza B Strain | Lee/40 | 2042 | 16.6 |
| Zeptometrix-Influenza B Strain | Florida/02/2006 | 2806 | 16.4 |
| Zeptometrix-Influenza B Strain | Brisbane/33/2008 | 2849 | 15.7 |
| Zeptometrix-Influenza B Strain | Panama/45/90 | 2536 | 26.9 |

Specificity Tests—Influenza B: Specificity and cross reactivity studies were performed in extraction buffer using the sample processing and analysis devices and systems as disclosed herein. CAb concentration was 5 µg/ml while DAb concentration was 100 ng/ml (final concentration after protocol run). No cross-reactivity was detected in these experiments.

TABLE 5

Specificity Tests - Influenza B

| Type | Sample | Mean RLU | CV % |
|---|---|---|---|
| Microbix CTL | Influenza B Pos | 120127 | 11.7 |
| Virusys CTL | Influenza B Pos | 95127 | 12.1 |
|  | Mean Positive | 107627 |  |
| Negative CTL | Negative Influenza B Virusys CTL | 1965 | 18.3 |
| Cross Reactant | Parainfluenza 1 | 1257 | 19.3 |
| Cross Reactant | Parainfluenza 2 | 1509 | 19.3 |
| Cross Reactant | Parainfluenza 3 | 1496 | 5.4 |
| Cross Reactant | Adenovirus | 1169 | 23.8 |
| Cross Reactant | *M. Pneumoniae* | 1979 | 6.5 |
| Cross Reactant | Respiratory Syncytial Virus | 1313 | 25.1 |
| Cross Reactant | *Corynebacterium diptheriae* | 3081 | 22.0 |
| Cross Reactant | *Streptococcus pyrogenes* | 4388 | 24.8 |
| Cross Reactant | *Streptococcus pneumoniae* | 6902 | 25.5 |
| Cross Reactant | CMV | 534 | 11.5 |
| Cross Reactant | *N. meningitis* | 3455 | 14.8 |
| Cross Reactant | Epstein Barr Virus | 1938 | 8.2 |
| Cross Reactant | Measles | 1710 | 23.6 |
| Cross Reactant | Mumps | 2423 | 10.0 |
| Cross Reactant | *E. coli* | 2291 | 9.2 |
|  | Mean RLU of cross reactants | 2363 |  |
|  | Modulation | 45.5 |  |

Clinical Evaluation of the Influenza a Assay: The performance of the Influenza A assay using the sample processing and analysis devices and systems as disclosed herein was compared to the results obtained with the Remel FDA kit. CAb concentration was 5 µg/ml while DAb concentration was maintained at 50 ng/ml (final concentration after the protocol was run). For the National Institute for Biological Standards and Control (NIBSC, Hertfordshire, UK) influenza strains, 50 µl of sample was added to the swab, and the swab was then treated like a sample swab. For the Zeptometrix panel controls (prediluted samples), 200 µl of sample was mixed with 200 µl of extraction buffer. Sample swabs were placed in 500 µl of extraction buffer and incubated for 3-5 minutes. This extracted sample was then analyzed using the devices and systems as disclosed herein. Swabs and samples were processed on the Remel FDA kit as directed in the kit instructions.

In the following tables, the "antibody index" (Ab Index) was used to determine whether or not target influenza antigens were detected in a sample. The Ab Index was calculated by dividing the mean RLU by the cutoff value (calculated from the normal samples). The cutoff value was set equal to the mean (normals) plus 4.5× standard deviation (normals). An Ab Index of less than one indicates that a sample was a normal sample (negative: no target influenza antigens were detected in the sample); an Ab Index of greater than one indicates that a sample was a positive sample (positive: target influenza antigens were detected in the sample). The column labeled "Remel FDA" presents the results of the Remel FDA kit on the indicated samples as either positive (+): influenza A detected, negative (−): influenza A not detected, or "NT": not tested.

TABLE 6

Clinical Evaluation - Influenza A

| Type | ID# |  | Ab Index | Remel FDA |
|---|---|---|---|---|
| Normal Clinicals | 1 |  | 0.02 | − |
|  | 6 |  | 0.02 | − |
|  | 7 |  | 0.02 | − |
|  | 8 |  | 0.02 | − |
|  | 10 |  | 0.02 | − |
|  | 11 |  | 0.01 | − |
|  | 12 |  | 0.02 | − |
|  | 13 |  | 0.01 | − |
|  | 15 |  | 0.02 | − |
|  | 16 |  | 0.04 | − |
|  | 17 |  | 0.02 | − |
|  | 18 |  | 0.02 | − |
|  | 2 |  | 0.32 | − |
|  | 3 |  | 0.23 | − |
|  | 4 |  | 0.20 | − |
|  | 9 |  | 0.05 | − |
|  | 14 |  | 0.29 | − |
|  | 19 |  | 0.95 | − |
| REMEL | FDA Swab |  | 2.66 | + |
| Zeptometrix CTLS | Influenza A POS |  | 1.27 | + |
| Zeptometrix Influenza A | Brisbane/10/07 |  | 2.58 | + |
| Zeptometrix Influenza A | Solomon Islands/03/2006 |  | 3.25 | + |
| Zeptometrix Influenza A | New Caledonia/20/99 |  | 2.57 | + |
| Zeptometrix Influenza A | Brisbane/59/07 |  | 5.16 | + |
| NIBSC STANDARDS FLU B Strains | Panama 45/90 |  | 0.06 | NT |
|  | Influenza Antigen B-Johannesburg |  | 0.06 | NT |
|  | Influenza Antigen B-Guangdong |  | 0.08 | NT |
|  | Influenza Antigen B/Yamanashi/166/98. |  | 0.11 | NT |
|  | Influenza Antigen B/Malaysia/2506/2004 |  | 0.02 | NT |
|  | Influenza Antigen B/Harbin/7/94 |  | 0.06 | NT |
|  | B:/Florida 4/2006 |  | 0.04 | NT |

TABLE 6-continued

Clinical Evaluation - Influenza A

| Type | ID# | Ab Index | Remel FDA |
|---|---|---|---|
| NIBSC STANDARDS FLU A Strains | Influenza Antigen A/California/7/2009-H1N1 | 6.88 | NT |
| | Influenza Antigen A/HongKong/1073/99 (H9N2) | 8.56 | NT |
| | Influenza Antigen A/Cambodia/RO405050/2007 (H5N1) | 6.02 | NT |
| | Influenza Antigen A/mallard/England/727/2006 (H2N3) | 5.70 | NT |
| | Influenza Antigen A/New York/107/2003 (H7N2) (NIBRG-109) | 7.26 | NT |
| | Influenza Antigen A/New York/55/2004 (H3N2) (NYMC X-157) | 6.54 | NT |

The results of these Influenza A clinical evaluation experiments showed that all samples with Influenza A antigens tested positive for Influenza A, while normal samples and samples with Influenza B antigens did not test positive for Influenza A; these results were in agreement with the results obtained with Remel FDA kit.

Clinical Evaluation of the Influenza B Assay: The performance of the Influenza B assay using the sample processing and analysis devices and systems as disclosed herein was compared to the Remel FDA kit. CAb concentration was 5 μg/ml while DAb concentration was maintained at 50 ng/ml (final concentration after the protocol was run). For the NIBSC influenza strains, 50 μl of sample was added to the swab, and the swab was then treated like a sample swab. For the Zeptometrix panel controls (prediluted samples), 200 μl of sample was mixed with 200 μl of extraction buffer. Swabs were placed in 500 μl of extraction buffer and incubated for 3-5 minutes. This extracted sample was then analyzed using the devices and systems as disclosed herein. Swabs and samples were processed on the Remel FDA kit as directed in the kit instructions. As discussed above, the cutoff value was set equal to the mean (normals) plus 4.5× standard deviation (normals), and the Ab Index was calculated by dividing the mean RLU by the cutoff value. The column labeled "Remel FDA" presents the results of the Remel FDA kit on the indicated samples as either positive (+): influenza B detected, or negative (−): influenza B not detected.

TABLE 7

Clinical Evaluation - Influenza B

| Type | ID# | Ab Index | Remel FDA |
|---|---|---|---|
| Normal Clinicals | 1 | 0.02 | − |
| | 6 | 0.03 | − |
| | 7 | 0.02 | − |
| | 8 | 0.02 | − |
| | 10 | 0.04 | − |
| | 11 | 0.02 | − |
| | 12 | 0.03 | − |
| | 13 | 0.01 | − |
| | 15 | 0.02 | − |
| | 16 | 0.06 | − |
| | 17 | 0.02 | − |
| | 18 | 0.03 | − |
| | 2 | 0.11 | − |
| | 3 | 0.03 | − |
| | 4 | 0.04 | − |
| | 9 | 0.05 | − |
| | 14 | 0.36 | − |
| | 19 | 0.79 | − |
| REMEL | FDA Pos B Swab | 10.78 | + |
| Zeptometric QC panel | Influenza A POS | 0.02 | − |
| Influenza A | Brisbane/10/07 | 0.03 | − |
| Influenza A | Solomon Islands/03/2006 | 0.01 | − |
| Influenza A | New Caledonia/20/99 | 0.02 | − |
| Influenza A | Brisbane/59/07 | 0.03 | − |
| NIBSC STANDARDS | Panama 45/90 | 14.38 | + |
| | Influenza Antigen B-Johannesburg | 2.58 | + |
| | Influenza Antigen B-Guangdong | 21.28 | + |
| | Influenza Antigen B/Yamanashi/166/98. | 6.05 | + |
| | Influenza Antigen B/Malaysia/2506/2004 | 7.53 | + |
| | Influenza Antigen B/Harbin/7/94 | 18.21 | + |
| | B:/Florida 4/2006 | 19.27 | + |
| | Influenza Antigen A/California/7/2009-H1N1 | 0.36 | − |
| | Influenza Antigen A/HongKong/1073/99 (H9N2) | 0.50 | − |
| | Influenza Antigen A/Cambodia/RO405050/2007 (H5N1) | 0.61 | − |
| | Influenza Antigen A/mallard/England/727/2006 (H2N3) | 0.50 | − |
| | Influenza Antigen A/New York/107/2003 (H7N2) (NIBRG-109) | 0.39 | − |
| | Influenza Antigen A/New York/55/2004 (H3N2) (NYMC X-157) | 0.12 | − |
| Zeptometrix Panel | | | |
| Influenza B | Lee/40 | 11.31 | + |
| Influenza B | Florida/02/2006 | 2.57 | + |

TABLE 7-continued

Clinical Evaluation - Influenza B

| Type | ID# | Ab Index | Remel FDA |
|---|---|---|---|
| Influenza B | Brisbane/33/2008 | 12.36 | + |
| Influenza B | Panama/45/90 | 5.93 | + |
| Influenza B | Panama/45/90 | 4.64 | + |

The results of these Influenza B clinical evaluation experiments showed that all samples with Influenza B antigens tested positive for Influenza B, while normal samples and samples with Influenza A antigens did not test positive for Influenza B; these results were in agreement with the results obtained with Remel FDA kit.

EXAMPLE 4

Further examples of markers indicative of infectious disease which may be detected, identified, and analyzed by methods, systems and devices disclosed herein are shown in FIGS. 22-32. For example, FIG. 22 lists further markers for diseases which are named in the figure, and which are grouped together as, e.g. nosocomial diseases (listed under the heading "Nosocomial Panel (HAI)"); respiratory diseases (listed under the heading "Respiratory Panel"); sexually transmitted diseases (listed under the heading "STD Panel (lesion swabs)" and "STD Panel (blood)", where the parenthetical expressions "lesion swabs" and "blood" indicate the source and method of obtaining the sample); infectious diseases (listed under the heading "Infectious Disease Panel"); gastrointestinal diseases (listed under the heading "Gastrointestinal Panel"); and urinary tract diseases (listed under the heading "Urinary Tract Infection Panel"). FIG. 22 also lists controls and additional assays, as indicated by the labels "Controls" and "Additional Assays".

Figures 23A, 23B:
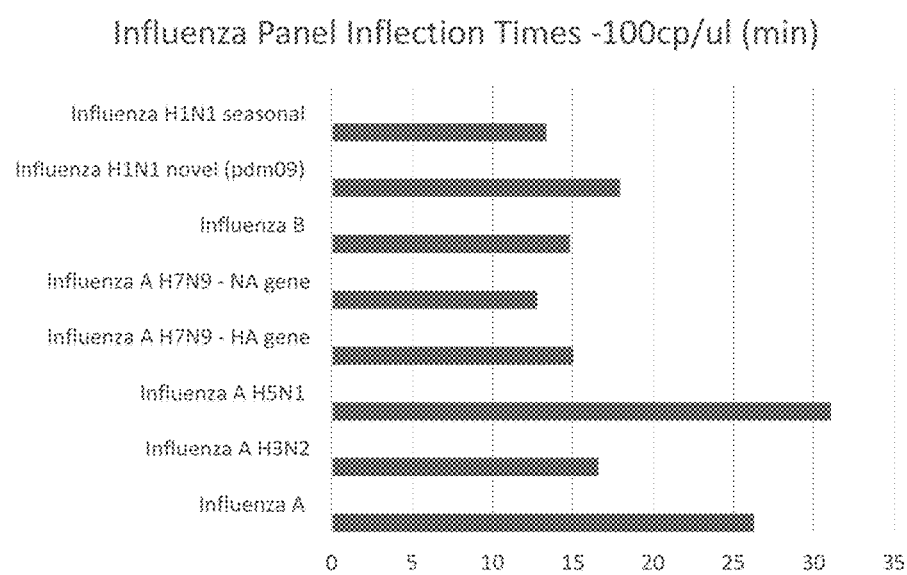
FIG. 23A shows various influenza panels naming influenza types which may be identified by the methods and devices discussed herein.
FIG. 23B shows inflection times for several influenza types which may be identified by the methods and devices discussed herein.

FIG. 23A shows an influenza panel naming several influenza types which may be identified by the methods and devices discussed herein. This figure refers to detection of various types of influenza by nucleic acid detection methods discussed herein. In this, and subsequent figures, and elsewhere in the application, "LOD" indicates "limit of detection." The influenza types may be detected at levels indicated in the figure; for example, influenza A may be detected by the methods, devices and systems disclosed herein when present in a sample at less than 100 copies per microliter (c/uL, where copies refers to copies of the target nucleic acid sequence indicative of influenza A). As indicated in FIG. 23A, other influenza types, such as influenza B and influenza H1N1 (seasonal) can be detected at levels of less than 10 copies per microliter.

FIG. 23B shows inflection times for several influenza types which may be identified by the methods and devices discussed herein. Target influenza nucleic acids indicative of the named influenza types were tested at 100 copies per microliter, and the time (from initiation of the nucleic acid detection assay) in minutes until detection is displayed (as detected by the inflection of the RFU output as shown, e.g., in previous figures).

FIG. 24A shows various respiratory disease panels naming respiratory disease types which may be identified by the methods and devices discussed herein. The limit of detection (LOD) is indicated for each respiratory disease in the right-most column of the figure; LODs were either 10 copies per microliter (c/uL) or 100 c/uL.

Figure 24B:
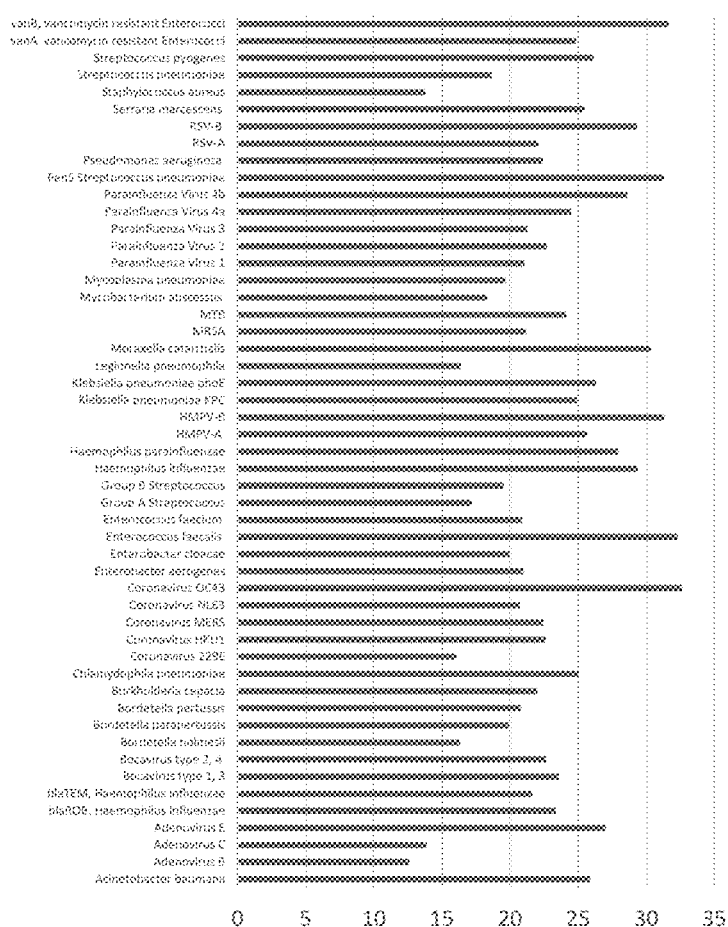
FIG. 24B shows inflection times for upper and lower respiratory tract disease types which may be identified by the methods and devices discussed herein.

FIG. 24B shows inflection times for upper and lower respiratory tract disease types which may be identified by the methods and devices discussed herein. Target respiratory disease nucleic acids indicative of the named respiratory diseases were tested at 100 copies per microliter, and the time (from initiation of the nucleic acid detection assay) in minutes until detection is displayed (as detected by the inflection of the RFU output as shown, e.g., in previous figures).

FIG. 25A shows various hospital acquired infectious diseases (indicated by the acronym "HAI") naming diseases which may be identified by the methods and devices discussed herein. The limit of detection (LOD) is indicated for each HAI disease in the right-most column of the figure; all LODs were 10 copies per microliter (c/uL).

Figure 25B:
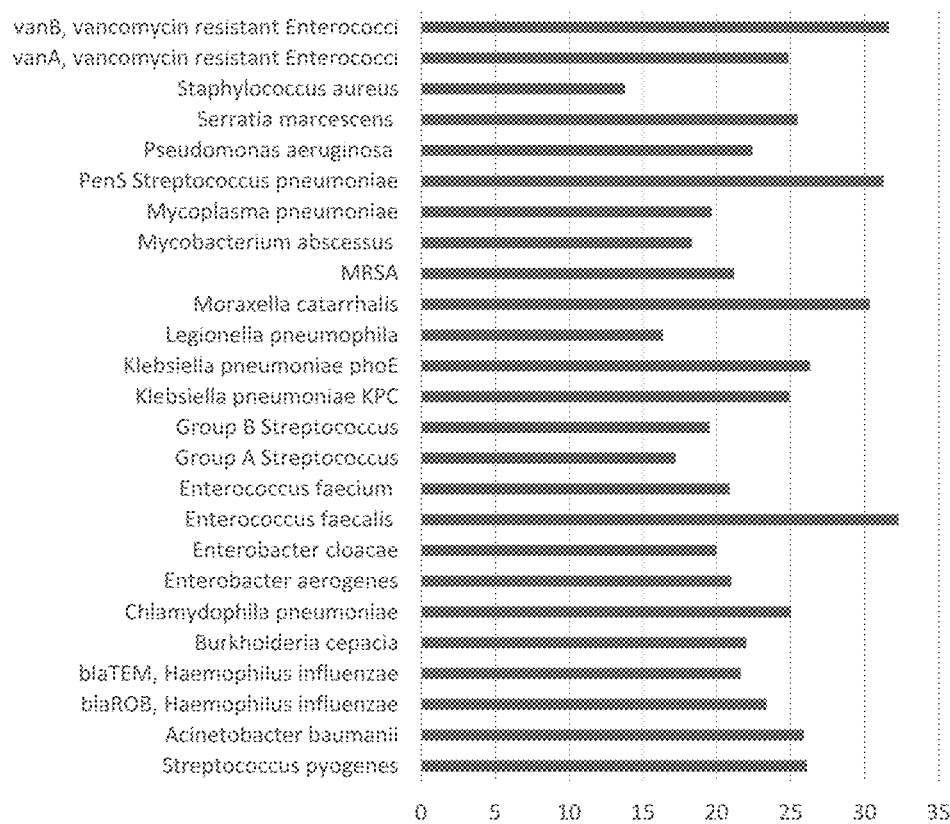
FIG. 25B shows inflection times for various hospital acquired infectious disease panels naming respiratory disease types which may be identified by the methods and devices discussed herein.

FIG. 25B shows inflection times for various hospital acquired infectious disease panels naming respiratory disease types which may be identified by the methods and devices discussed herein. Target nucleic acids indicative of the named HAI diseases were tested at 100 copies per microliter, and the time (from initiation of the nucleic acid detection assay) in minutes until detection is displayed (as detected by the inflection of the RFU output).

Figure 26:
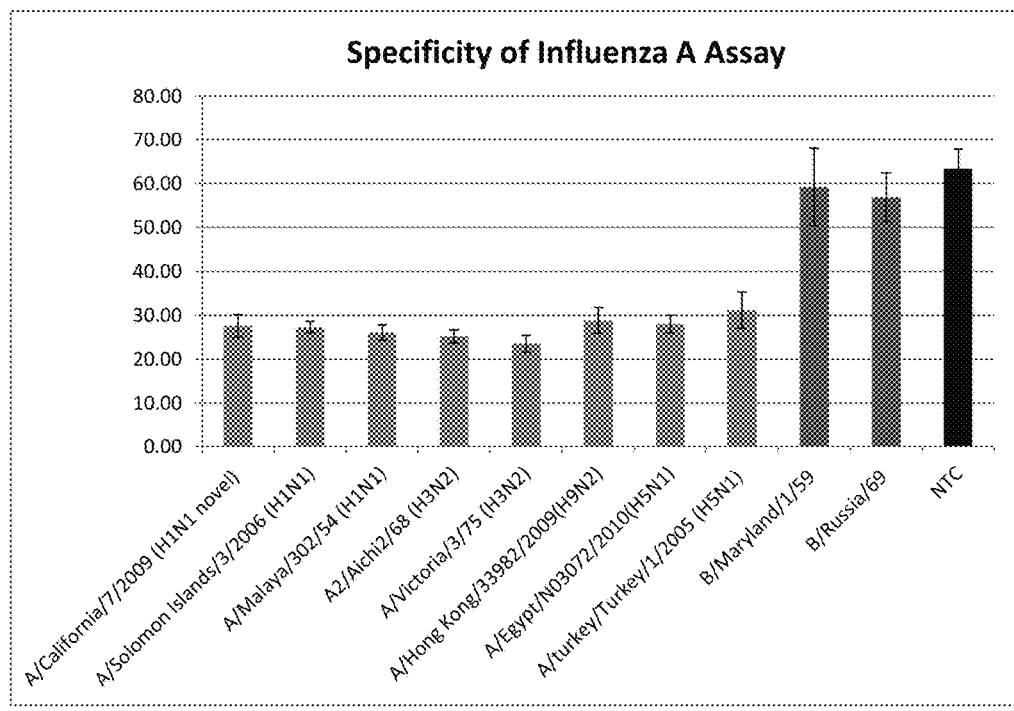
FIG. 26 shows results of an assay for influenza A that is designed to be inclusive for all Influenza A subtypes. The results are specific.

FIG. 26 shows results of a nucleic acid assay as described herein (see also the descriptions of these methods, e.g., in U.S. Patent Applications 61/800,606; 61/908,027; 62/001,050; and Ser. No. 14/214,850) for influenza A matrix protein that is designed to be inclusive for all Influenza A subtypes. The results are specific. Note that the inflection times for the "no template control" (NTC) as well as for the influenza B targets were significantly greater than (and readily distinguishable from) the inflection times for the influenza A targets.

Figure 27:
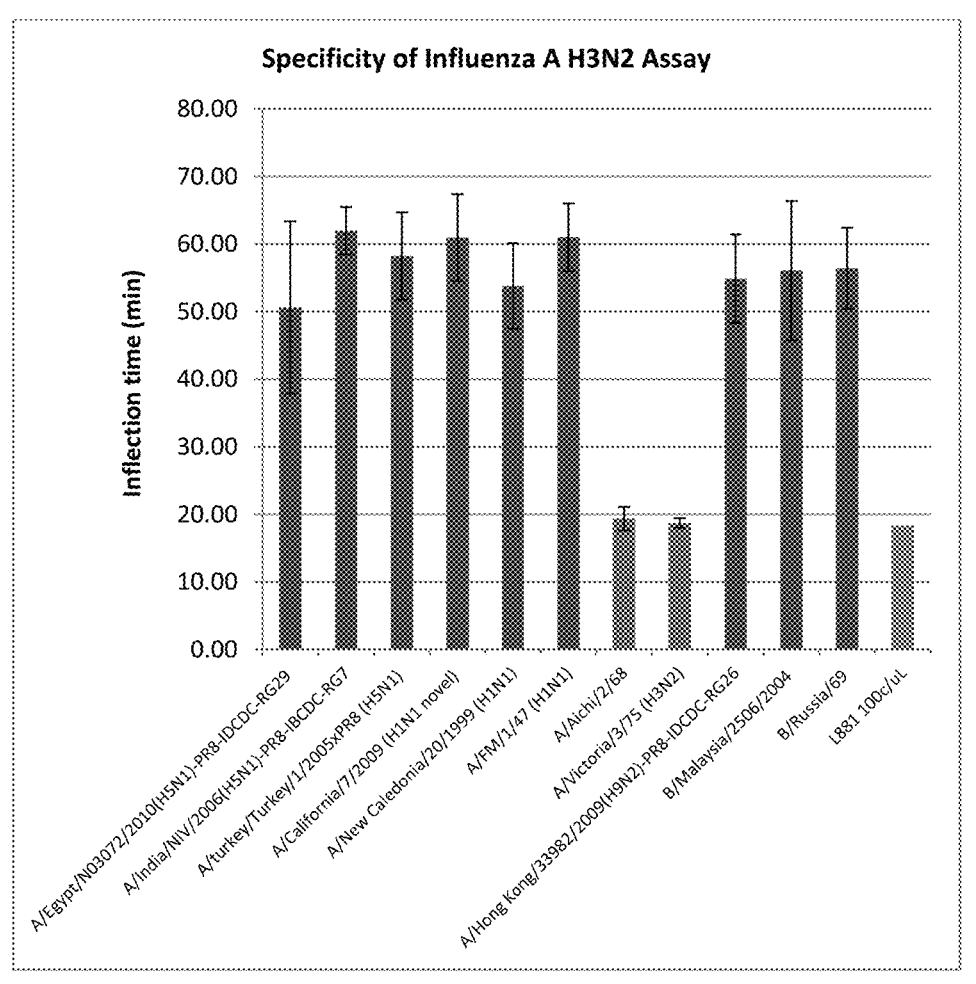

FIG. 27 shows that the nucleic acid assays described herein (see also the descriptions of these methods, e.g., in U.S. Patent Applications 61/800,606; 61/908,027; 62/001,050; and Ser. No. 14/214,850) are specific for the target H2N2 influenza type. The results are specific. Note that the inflection times for the H3N2 influenza A targets A/Aichi/2/68, A/Victoria/3/75, and L881 were significantly shorter than (and readily distinguishable from) the inflection times for the non-H3N2 influenzas.

Figure 28:
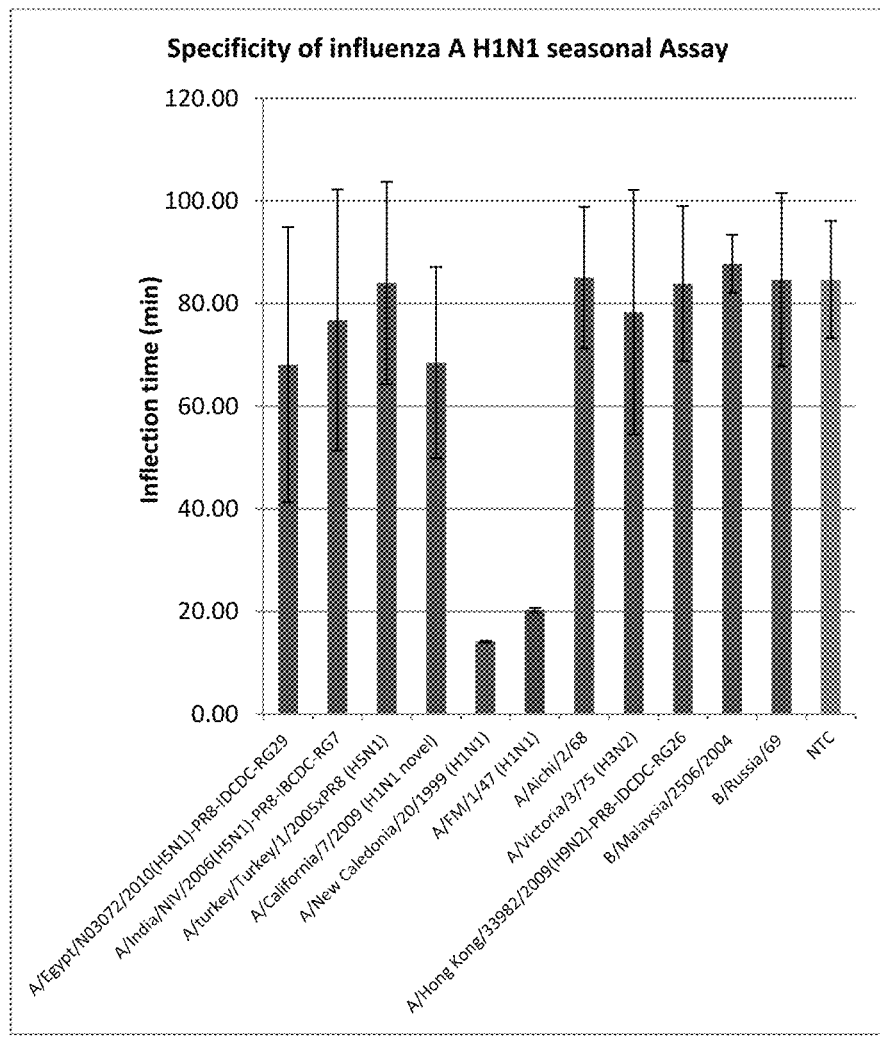
FIG. 28 shows the specificity of the nucleic acid assays for the target H1N1 seasonal influenza type.

FIG. 28 shows that the nucleic acid assays as described herein (see also the descriptions of these methods, e.g., in U.S. Patent Applications 61/800,606; 61/908,027; 62/001,050; and Ser. No. 14/214,850) are specific for the target H1N1 seasonal influenza type. Note that the inflection times for the H1N1 (seasonal) influenza A targets were significantly shorter than (and readily distinguishable from) the inflection times for the other influenzas and for the no template control (NTC).

FIG. 29 shows potential interfering substances for the nucleic acid assays as applied to the sexually transmitted disease (STD) panel, and concentrations which these interfering substances were tested for interference with the assays. None of the indicated concentrations of the potentially interfering substances interfered with the nucleic acid assays.

FIG. 30 shows potential interfering substances for the nucleic acid assays as applied to the sexually transmitted disease (STD) urine panel, and concentrations which these interfering substances were tested for interference with the assays. None of the indicated concentrations of the potentially interfering substances interfered with the nucleic acid assays.

FIG. 31 shows potential interfering substances for the nucleic acid assays as applied to the blood panel, and concentrations which these interfering substances were tested for interference with the assays. None of the indicated concentrations of the potentially interfering substances interfered with the nucleic acid assays.

While the above is a complete description of the preferred embodiment as described herein, it is possible to use various alternatives, modifications and equivalents. Therefore, the scope of the present invention should be determined not with reference to the above description but should, instead, be determined with reference to the appended claims, along with their full scope of equivalents. Any feature, whether preferred or not, may be combined with any other feature, whether preferred or not. The appended claims are not to be interpreted as including means-plus-function limitations, unless such a limitation is explicitly ecited in a given claim using the phrase "means for." It should be understood that as used in the description herein and throughout the claims that follow, the meaning of "a," "an," and "the" includes plural reference unless the context clearly dictates otherwise. Also, as used in the description herein and throughout the claims that follow, the meaning of "in" includes "in" and "on" unless the context clearly dictates otherwise. Finally, as used in the description herein and throughout the claims that follow, the meanings of "and" and "or" include both the conjunctive and disjunctive and may be used interchangeably unless the context expressly dictates otherwise. Thus, in contexts where the terms "and" or "or" are used, usage of such conjunctions do not exclude an "and/or" meaning unless the context expressly dictates otherwise.

This document contains material subject to copyright protection. The copyright owner (Applicant herein) has no objection to the facsimile reproduction by anyone of the patent document or the patent disclosure, as they appear in the US Patent and Trademark Office patent file or records, but otherwise reserves all copyright rights whatsoever. The following notice shall apply: Copyright 2013-2014 Theranos, Inc.

What is claimed is:

1. A method of detecting the presence of at least three disease markers comprising:
    a) introducing a sample and a swab sample obtained by a swab into an automatic sample processing device, wherein said automatic sample processing device is configured to perform nucleic acid assays, immunoassays, and cytometric assays,
    wherein said sample is contained in a cartridge containing all reagents required for the performance of said nucleic acid assays, immunoassays, and cytometric assays, said cartridge being configured to hold the sample and the swab sample,
    wherein said automatic sample processing device comprises:
        i) a sample handling system;
        ii) at least one detector; and
        iii) a cytometry station comprising an imaging aevice ana a stage for receiving a microscopy cuvette;
    b) transferring a portion of the sample to a nucleic acid assay unit, an immunoassay assay unit, and the microscopy cuvette with the aid of the sample handling system;
    c) performing an assay selected from one of a nucleic acid assay and an immunoassay, for the detection of at least one disease marker in the sample, or an aliquot thereof;
    d) obtaining an image of the sample, or an aliquot thereof, with said cytometry station for detecting the presence of at least one disease marker in the sample, or in an aliquot thereof; and
    e) performing another assay selected from one of a nucleic acid assay and an immunoassay, for the detection of at least another disease marker in the swab sample, or an aliquot thereof.

2. The method of claim 1, wherein the method is a point-of service (POS) method performed at a POS location.

3. The method of claim 1, wherein said assays are performed in less than about 40 minutes.

4. The method of claim 1, wherein said detecting the presence of at least three disease markers in the sample, or an aliquot or aliquots thereof comprises detecting at least one disease marker using a cytometry station, and detecting at least two disease markers using a detector.

5. The method of claim 1, comprising detecting the presence of a nucleic acid disease marker, a protein disease marker, and a cell morphology disease marker in the sample, or in an aliquot or aliquots thereof.

6. The method of claim 1, wherein said nucleic acid assay comprises isothermal nucleic acid amplification methods comprising non-cycling nucleic acid amplification methods,
    wherein said non-cycling nucleic acid amplification methods comprise contacting at least a portion of a sample with a first primer and a second primer, wherein:
    said first primer comprises a first tail region and a first template-binding region, wherein said first template-binding region is complementary to at least a first portion of said target nucleic acid, and
    said second primer comprises a second tail region and a second template-binding region, wherein said second template-binding region is complementary to at least a second portion of said target nucleic acid,
    wherein at least portions of said first and second tail regions are complementary to each other; and
    wherein said first and second tail regions of said first primer and of said second primer each comprise a) a 5' terminal nucleotide of the primer, b) an innermost nucleotide, wherein the innermost nucleotide is downstream from the 5' terminal nucleotide, and c) a middle section comprising one or more nucleotides between the 5' terminal nucleotide and the innermost nucleotide.

7. The method of claim 1, wherein at least one disease marker is a marker for inflammation, and at least one disease marker is a marker for a disease-causing agent.

8. The method of claim 1, wherein at least one disease marker is a marker for a disease selected from influenza, a respiratory disease, a sexually transmitted disease, and another infectious disease.

9. The method of claim 1, further comprising a sample obtained from a subject using a swab.

10. The method of claim 1, wherein at least one disease marker is a marker indicative of a sexually transmitted disease selected from a disease caused by herpes simplex-1 virus (HSV-1), herpes simplex-2 virus (HSV-2), human immunodeficiency virus (HIV), HIV-2 Group A, HIV-2

Group B, HIV-1 Group M, Hepatitis B, Hepatitis Delta, herpes simplex virus (HSV), streptococcus B, and treponema pallidum.

11. The method of claim 1, wherein transferring a portion of said sample comprises transferring the sample, or an aliquot thereof, by a fluid handling system comprising a pipette.

12. The method of claim 1, wherein performing an assay comprises centrifugation of the sample, or an aliquot thereof.

13. The method of claim 1, wherein performing an assay comprises separation of a blood sample into fractions to provide a serum fraction of the blood sample.

14. The method of claim 1, wherein performing an assay comprises dilution of the sample.

15. The method of claim 1, wherein said at least three disease markers comprise disease markers indicative a disease or diseases selected from the group of diseases consisting of Influenza A Matrix protein, Influenza H3N2, Influenza H1N1 seasonal, Influenza H1N1 novel, Influenza B, an Ebola virus, a Marburg virus, a Cueva virus, *Streptococcus pyogenes* (A), *Mycobacterium Tuberculosis*, *Staphylococcus aureus* (MR), *Staphylococcus aureus* (RS), *Bordetella pertussis* (whooping cough), *Streptococcus agalactiae* (B), Influenza H5N1, Influenza H7N9, Adenovirus B, Adenovirus C, Adenovirus E, Hepatitis b, Hepatitis c, Hepatitis delta, *Treponema pallidum*, HSV-1, HSV-2, HIV-1, HIV-2, Dengue 1, Dengue 2, Dengue 3, Dengue 4, Malaria, West Nile Virus, *Trypanosoma cruzi* (Chagas), *Klebsiella pneumoniae* (*Enterobacteriaceae* spp), *Klebsiella pneumoniae* carbapenemase (KPC), Epstein Barr Virus (mono), Rhinovirus, Parainfluenza virus (1), Parainfluenza virus (2), Parainfluenza virus (3), Parainfluenza virus (4a), Parainfluenza virus (4b), Respiratory syncytial virus (RSV) A, Respiratory syncytial virus (RSV) B, Coronavirus 229E, Coronavirus HKU1, Coronavirus OC43, Coronavirus NL63, Novel Coronavirus, Bocavirus, human metapneumovirus (HMPV), *Streptococcus pneumoniae* (penic R), *Streptococcus pneumoniae* (S), *Mycoplasma pneumoniae*, *Chlamydia pneumoniae*, *Bordetella parpertussis*, *Haemophilus influenzae* (ampic R), *Haemophilus influenzae* (ampic S), *Moraxella catarrhalis*, *Pseudomonas* spp (*aeruginosa*), *Haemophilus parainfluenzae*, *Enterobacter cloacae* (*Enterobacteriaceae* spp), *Enterobacter aerogenes* (*Enterobacteriaceae* spp), *Serratia marcescens* (*Enterobacteriaceae* spp), *Acinetobacter baumanii*, *Legionella* spp, *Escherichia coli*, *Candida*, *Chlamydia trachomatis*, Human Papilloma Virus, *Neisseria gonorrhoeae*, *plasmodium*, and *Trichomonas* (vagin).

16. The method of claim 1, wherein one of the at least three disease markers is a tuberculosis (Mycobacterium tuberculosis) marker.

17. The method of claim 1, wherein one of the at least three disease markers is a marker for a Staphylococcus bacterium or for a *Streptococcus* bacterium.

18. The method of claim 1, wherein one of the at least three disease markers is a marker for a virus selected from the group of viruses consisting of a filo virus, a Corona virus, West Nile Virus, Epstein-Barr Virus, and a Dengue Virus.

19. A method of detecting the presence of at least three disease markers comprising:
a) introducing a sample and a swab sample obtained by a swab into an automatic sample processing device, wherein said automatic sample processing device is configured to perform nucleic acid assays, immunoassays, and cytometric assays,
wherein said sample is contained in a cartridge containing all reagents required for the performance of said nucleic acid assays, immunoassays, and cytometric assays, said cartridge being configured to hold the sample and the swab sample,
wherein said automatic sample processing device comprises:
i) a sample handling system;
ii) at least one detector; and
iii) a cytometry station comprising an imaging device and a stage for receiving a microscopy cuvette;
b) transferring a portion of the sample to a nucleic acid assay unit, an immunoassay assay unit, and the microscopy cuvette with the aid of the sample handling system;
c) performing an assay selected from one of a nucleic acid assay and an immunoassay, for the detection of at least one disease marker in the sample, or an aliquot thereof;
d) obtaining an image of the sample, or an aliquot thereof, with said cytometry station for detecting the presence of at least one disease marker in the sample, or in an aliquot thereof; and
e) performing another assay selected from one of a nucleic acid assay and an immunoassay, for the detection of at least another disease marker in the swab sample, or an aliquot thereof, wherein said sample comprises a fingerstick blood sample.

20. A method of detecting the presence of at least three disease markers comprising:
a) introducing a sample and a swab sample obtained by a swab into an automatic sample processing device, wherein said automatic sample processing device is configured to perform nucleic acid assays, immunoassays, and cytometric assays,
wherein said sample is contained in a cartridge containing all reagents required for the performance of said nucleic acid assays, immunoassays, and cytometric assays, said cartridge being configured to hold the sample and the swab sample,
wherein said automatic sample processing device comprises:
i) a sample handling system;
ii) at least one detector; and
iii) a cytometry station comprising an imaging device and a stage for receiving a microscopy cuvette;
b) transferring a portion of the sample to a nucleic acid assay unit, an immunoassay assay unit, and the microscopy cuvette with the aid of the sample handling system;
c) performing an assay selected from one of a nucleic acid assay and an immunoassay, for the detection of at least one disease marker in the sample, or an aliquot thereof;
d) obtaining an image of the sample, or an aliquot thereof, with said cytometry station for detecting the presence of at least one disease marker in the sample, or in an aliquot thereof; and
e) performing another assay selected from one of a nucleic acid assay and an immunoassay, for the detection of at least another disease marker in the swab sample, or an aliquot thereof, wherein said sample has a volume of less than 250 microliters.

* * * * *